(12) United States Patent
McLean et al.

(10) Patent No.: US 8,758,366 B2
(45) Date of Patent: Jun. 24, 2014

(54) MULTI-ACTUATING TRIGGER ANCHOR DELIVERY SYSTEM

(75) Inventors: Matt McLean, San Francisco, CA (US); Floria Cheng, San Francisco, CA (US); Daniel Merrick, Dublin, CA (US); Mitchell C. Barham, San Mateo, CA (US); Andrew L. Johnston, Redwood City, CA (US); Joseph Catanese, III, San Leandro, CA (US); Theodore C. Lamson, Pleasanton, CA (US); Joshua Makower, Los Altos, CA (US)

(73) Assignee: Neotract, Inc., Pleasanton, CA (US)

( * ) Notice: Subject to any disclaimer, the term of this patent is extended or adjusted under 35 U.S.C. 154(b) by 1247 days.

(21) Appl. No.: 11/775,167

(22) Filed: Jul. 9, 2007

(65) Prior Publication Data

US 2009/0018553 A1    Jan. 15, 2009

(51) Int. Cl.
*A61B 17/10* (2006.01)

(52) U.S. Cl.
USPC ........................................... 606/139

(58) Field of Classification Search
USPC .......... 606/139, 213, 143, 232, 151, 153, 144
See application file for complete search history.

(56) References Cited

U.S. PATENT DOCUMENTS

| | | |
|---|---|---|
| 659,422 A | 10/1900 | Shidler |
| 780,392 A | 1/1905 | Wanamaker et al. |
| 789,467 A | 5/1905 | West |
| 2,579,192 A | 12/1951 | Kohl |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,713,680 A | 1/1973 | Pagano |
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |

(Continued)

FOREIGN PATENT DOCUMENTS

| | | |
|---|---|---|
| DE | 10159470 | 6/2003 |
| EP | 0246836 | 12/1991 |

(Continued)

OTHER PUBLICATIONS

Richard Berges et al., "Alternative Minimalinvasive Therapien Beim Benignen Prostatasyndrom", Medizin, Jg. 104, Heft 37, Sep. 14, 2007.

(Continued)

*Primary Examiner* — Gregory Anderson
*Assistant Examiner* — Christina Lauer
(74) *Attorney, Agent, or Firm* — Steptoe & Johnson LLP

(57) ABSTRACT

A single trigger system and associated method for manipulating tissues and anatomical or other structures in medical applications for the purpose of treating diseases or disorders or other purposes. In one aspect, the system includes a delivery device configured to deploy and implant anchor devices for such purposes.

18 Claims, 49 Drawing Sheets

(56) References Cited

U.S. PATENT DOCUMENTS

| | | | |
|---|---|---|---|
| 4,210,148 A | | 7/1980 | Stivala |
| 4,235,238 A | | 11/1980 | Ogiu et al. |
| 4,291,698 A | | 9/1981 | Fuchs et al. |
| 4,409,974 A | | 10/1983 | Freedland |
| 4,493,323 A | | 1/1985 | Albright et al. |
| 4,513,746 A | * | 4/1985 | Aranyi et al. ............... 606/220 |
| 4,621,640 A | | 11/1986 | Mulhollan et al. |
| 4,657,461 A | | 4/1987 | Smith |
| 4,669,473 A | | 6/1987 | Richards et al. |
| 4,705,040 A | | 11/1987 | Mueller et al. |
| 4,714,281 A | | 12/1987 | Peck |
| 4,738,255 A | | 4/1988 | Goble et al. |
| 4,741,330 A | | 5/1988 | Hayhurst |
| 4,744,364 A | | 5/1988 | Kensey |
| 4,750,492 A | | 6/1988 | Jacobs |
| 4,762,128 A | | 8/1988 | Rosenbluth |
| 4,823,794 A | | 4/1989 | Pierce |
| 4,899,743 A | | 2/1990 | Nicholson et al. |
| 4,926,860 A | | 5/1990 | Stice et al. |
| 4,946,468 A | | 8/1990 | Li |
| 4,955,913 A | | 9/1990 | Robinson |
| 4,968,315 A | | 11/1990 | Gatturna et al. |
| 5,002,550 A | | 3/1991 | Li |
| 5,041,129 A | | 8/1991 | Hayhurst et al. |
| 5,046,513 A | | 9/1991 | Gatturna et al. |
| 5,053,046 A | | 10/1991 | Janese |
| 5,100,421 A | | 3/1992 | Christoudias |
| 5,123,914 A | | 6/1992 | Cope |
| 5,129,912 A | | 7/1992 | Noda et al. |
| 5,192,303 A | | 3/1993 | Gatturna et al. |
| 5,203,787 A | | 4/1993 | Noblitt et al. |
| 5,217,470 A | | 6/1993 | Weston |
| 5,217,486 A | | 6/1993 | Rice et al. |
| 5,234,454 A | | 8/1993 | Bangs |
| 5,236,445 A | | 8/1993 | Hayhurst et al. |
| 5,258,015 A | | 11/1993 | Li et al. |
| 5,269,809 A | | 12/1993 | Hayhurst et al. |
| 5,330,488 A | | 7/1994 | Goldrath |
| 5,334,200 A | | 8/1994 | Johnson |
| 5,336,240 A | | 8/1994 | Metzler et al. |
| 5,354,271 A | | 10/1994 | Voda |
| 5,358,511 A | | 10/1994 | Gatturna et al. |
| 5,364,408 A | | 11/1994 | Gordon |
| 5,366,490 A | | 11/1994 | Edwards et al. |
| 5,368,599 A | | 11/1994 | Hirsch et al. |
| 5,370,646 A | | 12/1994 | Reese et al. |
| 5,380,334 A | | 1/1995 | Torrie et al. |
| 5,391,182 A | | 2/1995 | Chin |
| 5,403,348 A | | 4/1995 | Bonutti |
| 5,405,352 A | | 4/1995 | Weston |
| 5,411,520 A | | 5/1995 | Nash et al. |
| 5,417,691 A | | 5/1995 | Hayhurst |
| 5,435,805 A | | 7/1995 | Edwards et al. |
| 5,470,337 A | | 11/1995 | Moss |
| 5,472,446 A | | 12/1995 | de la Torre |
| 5,480,406 A | | 1/1996 | Nolan et al. |
| 5,501,690 A | | 3/1996 | Measamer et al. |
| 5,507,754 A | * | 4/1996 | Green et al. ............... 606/139 |
| 5,522,846 A | | 6/1996 | Bonutti |
| 5,531,763 A | | 7/1996 | Mastri et al. |
| 5,536,240 A | | 7/1996 | Edwards et al. |
| 5,540,704 A | | 7/1996 | Gordon et al. |
| 5,545,171 A | | 8/1996 | Sharkey et al. |
| 5,545,178 A | | 8/1996 | Kensey et al. |
| 5,550,172 A | | 8/1996 | Regula et al. |
| 5,554,162 A | | 9/1996 | DeLange |
| 5,554,171 A | | 9/1996 | Gatturna et al. |
| 5,562,689 A | | 10/1996 | Green et al. |
| 5,569,305 A | | 10/1996 | Bonutti |
| 5,571,104 A | | 11/1996 | Li |
| 5,573,540 A | | 11/1996 | Yoon |
| 5,578,044 A | | 11/1996 | Gordon et al. |
| 5,591,177 A | | 1/1997 | Lehrer |
| 5,593,421 A | | 1/1997 | Bauer |
| 5,611,515 A | | 3/1997 | Benderev et al. |
| 5,626,614 A | | 5/1997 | Hart |
| 5,630,824 A | | 5/1997 | Hart |
| 5,647,836 A | | 7/1997 | Blake, III et al. |
| 5,665,109 A | | 9/1997 | Yoon |
| 5,667,486 A | | 9/1997 | Mikulich et al. |
| 5,669,917 A | | 9/1997 | Sauer et al. |
| 5,690,649 A | | 11/1997 | Li |
| 5,690,677 A | | 11/1997 | Schmieding et al. |
| 5,697,950 A | | 12/1997 | Fucci et al. |
| 5,707,394 A | | 1/1998 | Miller et al. |
| 5,716,368 A | | 2/1998 | de la Torre et al. |
| 5,718,717 A | | 2/1998 | Bonutti |
| 5,725,556 A | | 3/1998 | Moser et al. |
| 5,725,557 A | | 3/1998 | Gatturna et al. |
| 5,733,306 A | | 3/1998 | Bonutti |
| 5,741,276 A | | 4/1998 | Poloyko et al. |
| 5,746,753 A | | 5/1998 | Sullivan et al. |
| 5,749,846 A | | 5/1998 | Edwards et al. |
| 5,752,963 A | | 5/1998 | Allard et al. |
| 5,782,862 A | | 7/1998 | Bonutti |
| 5,782,864 A | | 7/1998 | Lizardi |
| 5,800,445 A | | 9/1998 | Ratcliff et al. |
| 5,807,403 A | | 9/1998 | Beyar et al. |
| 5,810,848 A | | 9/1998 | Hayhurst |
| 5,814,072 A | | 9/1998 | Bonutti |
| 5,845,645 A | | 12/1998 | Bonutti |
| 5,846,254 A | | 12/1998 | Schulze et al. |
| 5,861,002 A | | 1/1999 | Desai |
| 5,868,762 A | | 2/1999 | Cragg et al. |
| 5,873,891 A | | 2/1999 | Sohn |
| 5,897,574 A | | 4/1999 | Bonutti |
| 5,899,911 A | | 5/1999 | Carter |
| 5,899,921 A | | 5/1999 | Caspari et al. |
| 5,904,696 A | | 5/1999 | Rosenman |
| 5,908,428 A | | 6/1999 | Scirica et al. |
| 5,919,198 A | | 7/1999 | Graves, Jr. et al. |
| 5,919,202 A | | 7/1999 | Yoon |
| 5,921,986 A | | 7/1999 | Bonutti |
| 5,928,252 A | | 7/1999 | Steadman et al. |
| 5,931,844 A | | 8/1999 | Thompson et al. |
| 5,944,739 A | | 8/1999 | Zlock et al. |
| 5,948,001 A | | 9/1999 | Larsen |
| 5,948,002 A | | 9/1999 | Bonutti |
| 5,954,057 A | | 9/1999 | Li |
| 5,954,747 A | | 9/1999 | Clark |
| 5,964,732 A | | 10/1999 | Willard |
| 5,971,447 A | | 10/1999 | Steck, III |
| 6,010,514 A | | 1/2000 | Burney et al. |
| 6,011,525 A | | 1/2000 | Piole |
| 6,030,393 A | | 2/2000 | Corlew |
| 6,033,430 A | | 3/2000 | Bonutti |
| 6,036,701 A | | 3/2000 | Rosenman |
| 6,048,351 A | | 4/2000 | Gordon et al. |
| 6,053,908 A | | 4/2000 | Crainich et al. |
| 6,056,722 A | | 5/2000 | Jayaraman |
| 6,056,772 A | | 5/2000 | Bonutti |
| 6,068,648 A | | 5/2000 | Cole et al. |
| 6,080,167 A | | 6/2000 | Lyell |
| 6,086,608 A | | 7/2000 | Ek et al. |
| 6,110,183 A | | 8/2000 | Cope |
| 6,117,160 A | | 9/2000 | Bonutti |
| 6,117,161 A | | 9/2000 | Li et al. |
| 6,120,539 A | | 9/2000 | Eldridge et al. |
| 6,139,555 A | | 10/2000 | Hart et al. |
| RE36,974 E | | 11/2000 | Bonutti |
| 6,143,006 A | | 11/2000 | Chan |
| 6,159,234 A | | 12/2000 | Bonutti et al. |
| 6,200,329 B1 | | 3/2001 | Fung et al. |
| 6,206,895 B1 | | 3/2001 | Levinson |
| 6,228,096 B1 | | 5/2001 | Marchand |
| 6,258,124 B1 | | 7/2001 | Darois et al. |
| 6,261,302 B1 | | 7/2001 | Voegele et al. |
| 6,270,530 B1 | | 8/2001 | Eldridge et al. |
| 6,280,460 B1 | | 8/2001 | Bolduc et al. |
| 6,290,711 B1 | | 9/2001 | Caspari et al. |
| 6,312,448 B1 | | 11/2001 | Bonutti |
| 6,319,263 B1 | | 11/2001 | Levinson |
| 6,322,112 B1 | | 11/2001 | Duncan |
| 6,332,889 B1 | | 12/2001 | Sancoff et al. |

(56) References Cited

U.S. PATENT DOCUMENTS

| | | |
|---|---|---|
| 6,398,795 B1 | 6/2002 | McAlister et al. |
| 6,425,900 B1 | 7/2002 | Knodel et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | St. Goar et al. |
| 6,641,592 B1 | 11/2003 | Sauer et al. |
| 6,656,182 B1 | 12/2003 | Hayhurst |
| 6,660,023 B2 | 12/2003 | McDevitt et al. |
| 6,663,589 B1 | 12/2003 | Halevy |
| 6,663,639 B1 | 12/2003 | Laufer et al. |
| 6,699,263 B2 | 3/2004 | Cope |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom, Jr. |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,011,688 B2 | 3/2006 | Gryska et al. |
| 7,015,253 B2 | 3/2006 | Escandon et al. |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | Dicesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas |
| 7,226,558 B2 | 6/2007 | Nieman et al. |
| 7,232,448 B2 | 6/2007 | Battles et al. |
| 7,288,063 B2 | 10/2007 | Petros et al. |
| 7,303,108 B2 | 12/2007 | Shelton, IV |
| 7,320,701 B2 | 1/2008 | Haut et al. |
| 7,322,974 B2 | 1/2008 | Swoyer et al. |
| 7,334,822 B1 | 2/2008 | Hines, Jr. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,553,317 B2 | 6/2009 | Weisenburgh, II et al. |
| 7,608,108 B2 | 10/2009 | Bhatnagar et al. |
| 7,658,311 B2 | 2/2010 | Boudreaux |
| 7,674,275 B2 | 3/2010 | Martin et al. |
| 7,727,248 B2 | 6/2010 | Smith et al. |
| 7,896,891 B2 * | 3/2011 | Catanese et al. ............... 606/139 |
| 7,905,889 B2 * | 3/2011 | Catanese et al. ............... 606/139 |
| 8,043,309 B2 * | 10/2011 | Catanese et al. ............... 606/151 |
| 2001/0044639 A1 | 11/2001 | Levinson |
| 2002/0095154 A1 | 7/2002 | Atkinson et al. |
| 2002/0128684 A1 | 9/2002 | Foerster |
| 2002/0161382 A1 | 10/2002 | Neisz et al. |
| 2003/0109769 A1 | 6/2003 | Lowery et al. |
| 2003/0191497 A1 | 10/2003 | Cope |
| 2003/0204195 A1 | 10/2003 | Keane et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0177181 A1 | 8/2005 | Kagan et al. |
| 2005/0203344 A1 | 9/2005 | Orban, III et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | Starksen et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 * | 4/2007 | Bonutti et al. ............... 606/99 |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 * | 3/2008 | Zannis et al. ............... 606/144 |
| 2008/0082113 A1 | 4/2008 | Bishop et al. |

(56) References Cited

U.S. PATENT DOCUMENTS

| | | |
|---|---|---|
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2010/0010631 A1 | 1/2010 | Otte et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 133886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO 92/10142 | 6/1992 |
| WO | WO 93/04727 | 3/1993 |
| WO | WO 93/15664 | 8/1993 |
| WO | WO0230335 | 4/2002 |
| WO | WO03/039334 | 5/2003 |
| WO | WO 03/077772 | 9/2003 |
| WO | WO2004019787 | 3/2004 |
| WO | WO2004017845 | 4/2004 |
| WO | WO2004030569 | 4/2004 |
| WO | WO 2004103189 | 12/2004 |
| WO | WO2007064906 | 6/2007 |
| WO | WO2007053516 | 10/2007 |
| WO | WO2008006084 | 1/2008 |
| WO | WO 2008006084 | 1/2008 |
| WO | WO2008043044 | 4/2008 |
| WO | WO2008043917 | 4/2008 |
| WO | WO 2008043917 | 4/2008 |
| WO | WO2009009617 | 1/2009 |
| WO | WO2010011832 | 1/2010 |

OTHER PUBLICATIONS

Rudolf Hartung, et al., "Instrumentelle Therapie der benignen Prostatahyperplasie", Medizin, Deutsches Ärzteblatt 97, Heft 15, Apr. 14, 2000.

Klaus Hofner, et al., "Operative Therapie des benignen Prostatasyndroms", Medizin, Dtsch Arztebl 2007; 104(36):A 2424-9.

R. Hubmann, "Geschichte der transurethralen Prostataeingriffe", Geschichte der Medizin, Urologe [B] 2000 40:152-160.

U. Jonas, et al., "Benigne Prostatahyperplasie", Der Urologe 2006 [Sonderheft] 45:134-144.

O.A. Bacharova, et al., "The Effect of Rhodiolae Rosea Extract on Incidence Rate of Superficial Bladder Carcinoma Relapses", Kozin 1995.

S. Kruck, et al., "Aktuelle Therapiemöglichkeiten des Benignen Prostata-Syndroms", J Urol Urogynakol 2009; 16 (1):19-22.

Osamu Miyake, "Medical Examination and Treatment for BPH", Pharma Med vol. 22, No. 3, 2004, pp. 97-103.

Ohashi Teruhisa, "Urinary Dysfunction by Lower Urinary Tract Obstruction in Male", Pharma Medica vol. 8, No. 8, pp. 35-39.

O. Reich, et al., "Benignes Prostatasyndrom (BPS)", Der Urologe a Issue vol. 45, No. 6, Jun. 2006, pp. 769-782.

Daito Takashi, "Low-Invasive Treatment for BPH", Medico vol. 34, No. 10, pp. 366-369.

Trapeznikov et al., "New Technologies in the Treatment of Benign Prostatic Hyperplasia", Urologia Nefrol (Mosk) 1996, Jul-Aug (4):41-47.

Koyanagi Tomohiko, et al., "Surgery View of 21st Century", Urological Surgery, vol. 84, No. 1, pp. 47-53.

Borzhievski, et al., "Tactics of the Surgical Treatment of Patients With Prostatic Adenoma and Acute Urinary Retention", Urologia Nefrol (Mosk), 1987, Jan-Feb (1):39-43.

Sharp, Howard T., M.D., et al., "Instruments and Methods—the 4-S Modification of the Roeder Knot: How to Tie It", Obstetrics & Gynecology, pp. 1004-1006, vol. 90, No. 6, Dec. 1997.

P. Schauer et al., "New applications for endoscopy: the emerging field of endoluminal and transgastric bariatric surgery," Surgical Endoscopy, Received Apr. 24, 2006/Accepted Jun. 7, 2006.

Yeung, Jeff, "Treating Urinary Stress Incontinence Without Incision with Endoscopic Suture Anchor & Approximating Device," Aleeva Medical Inc., 2007.

\* cited by examiner

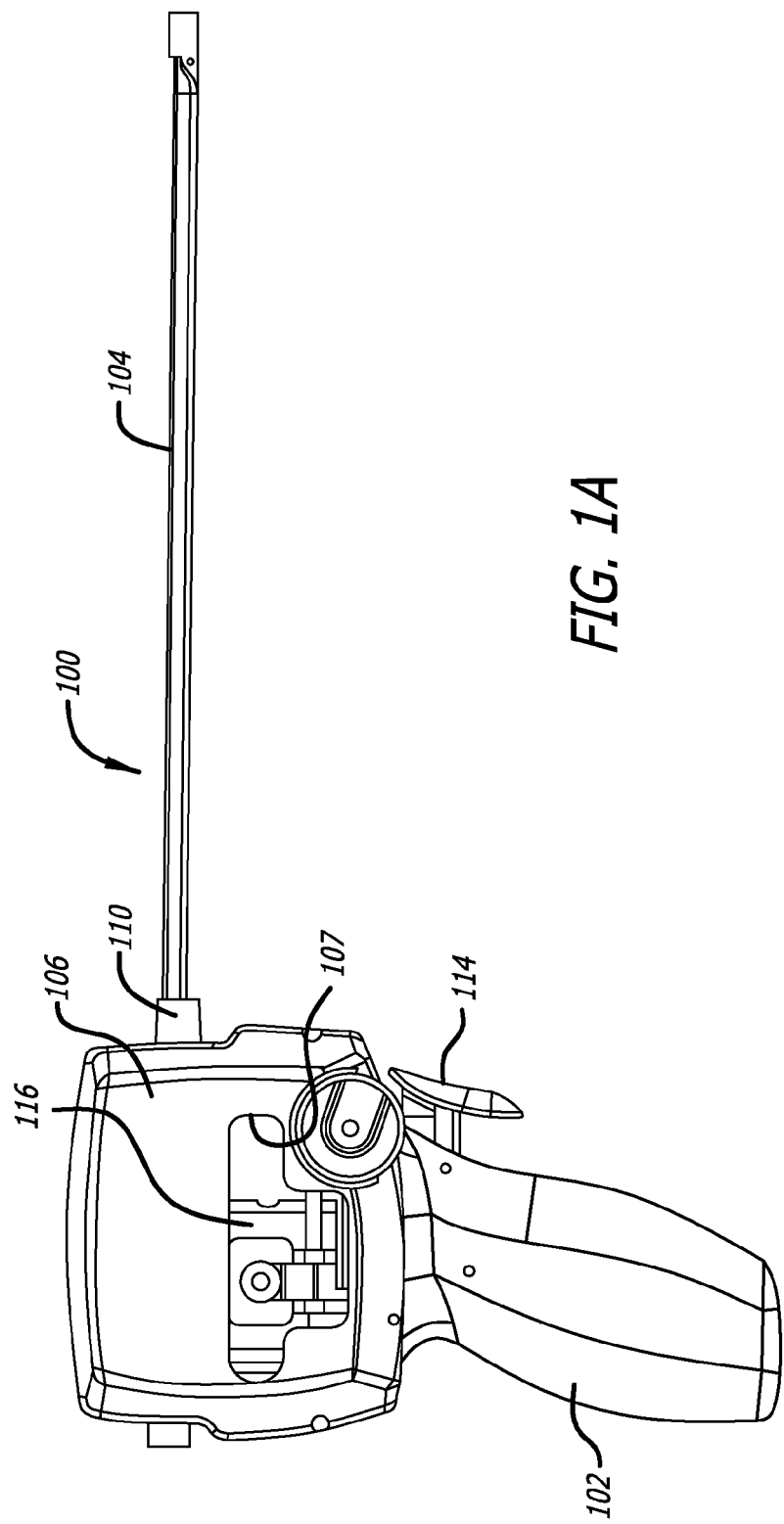

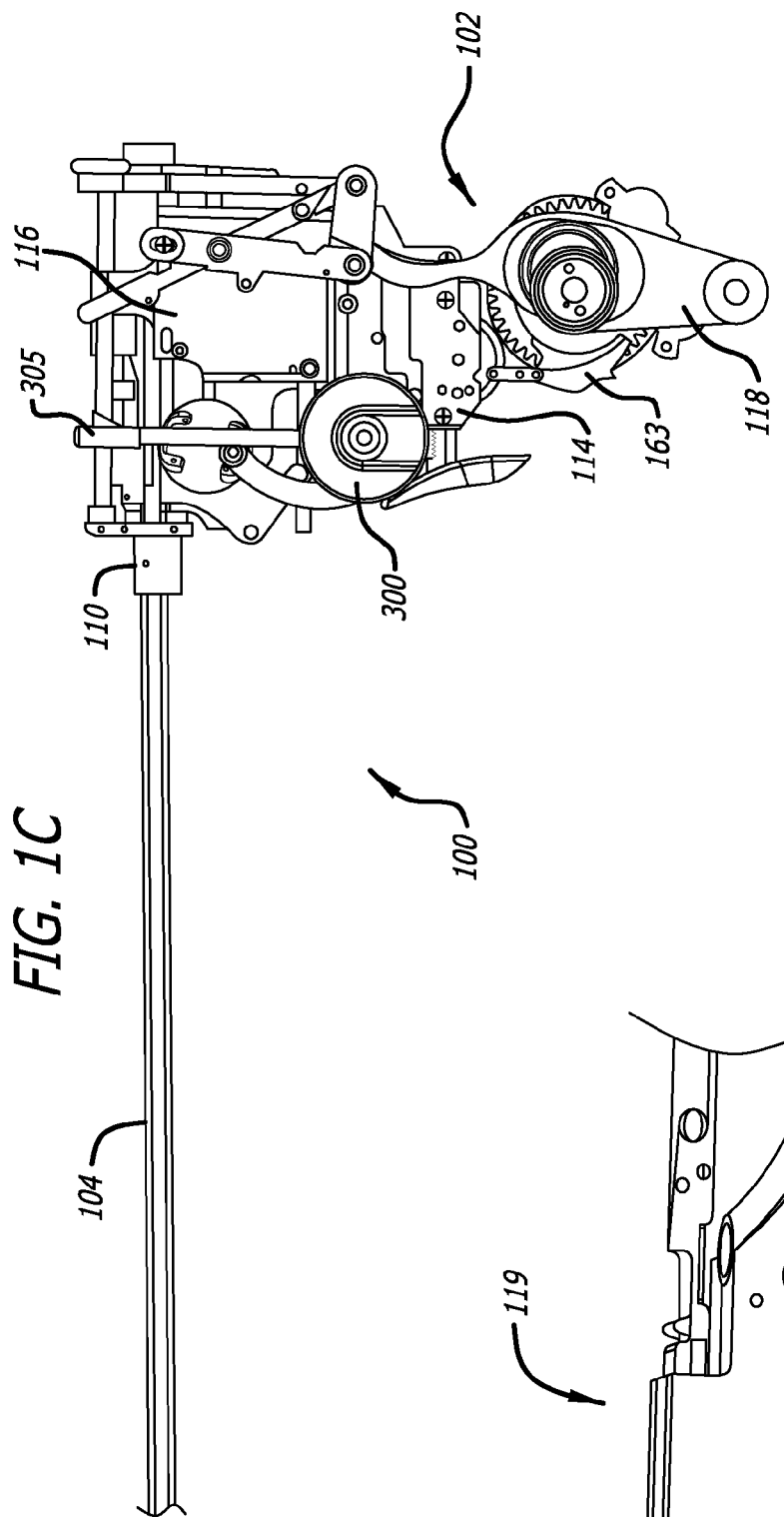
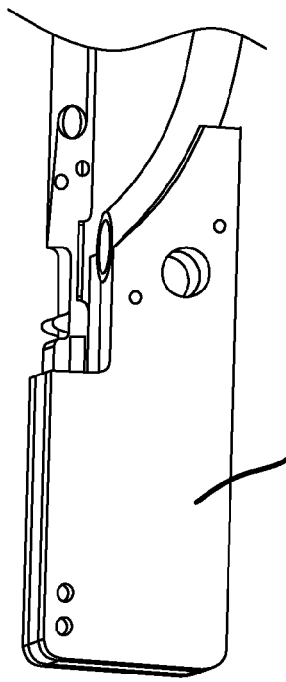
FIG. 1C
FIG. 1D

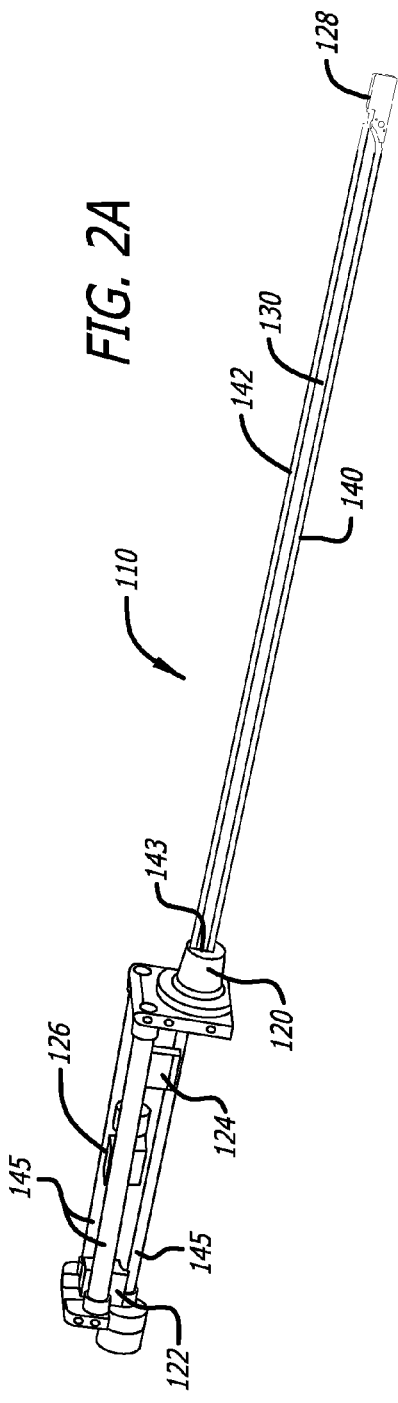

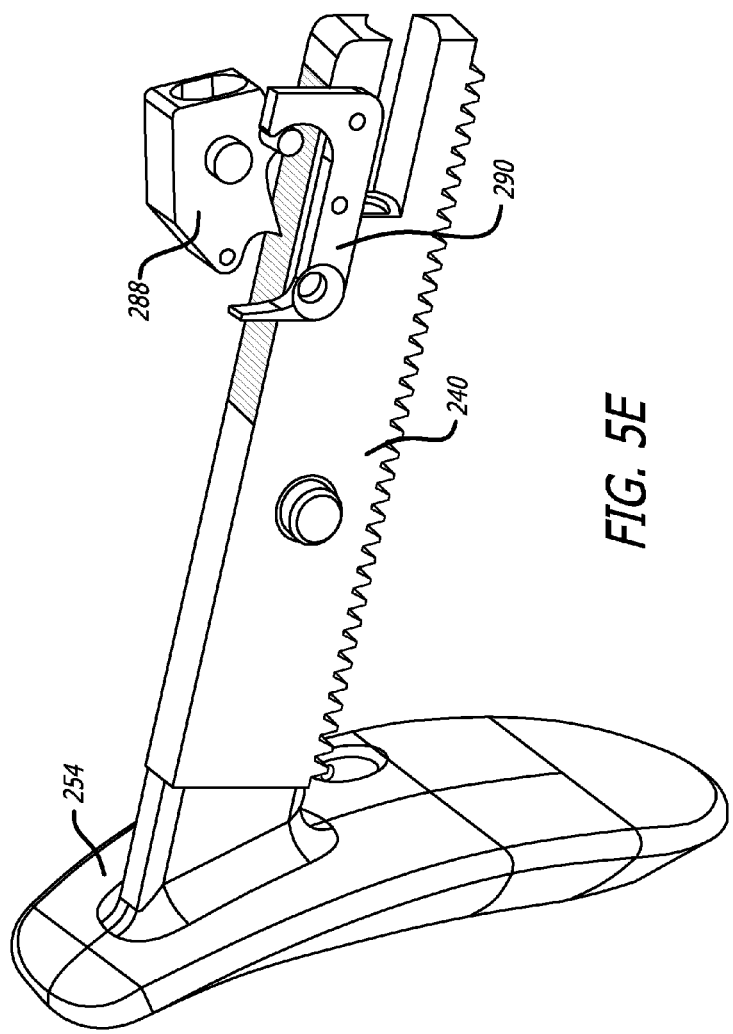

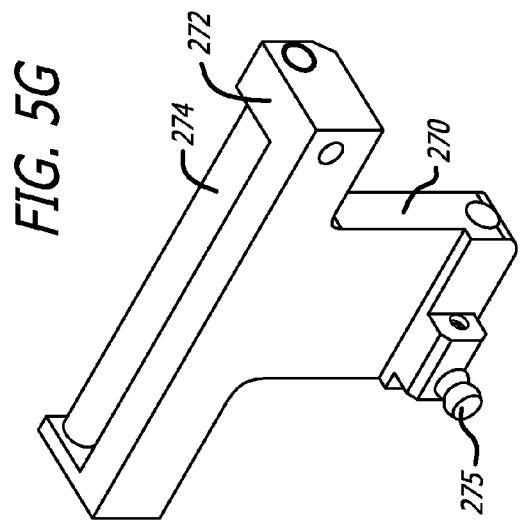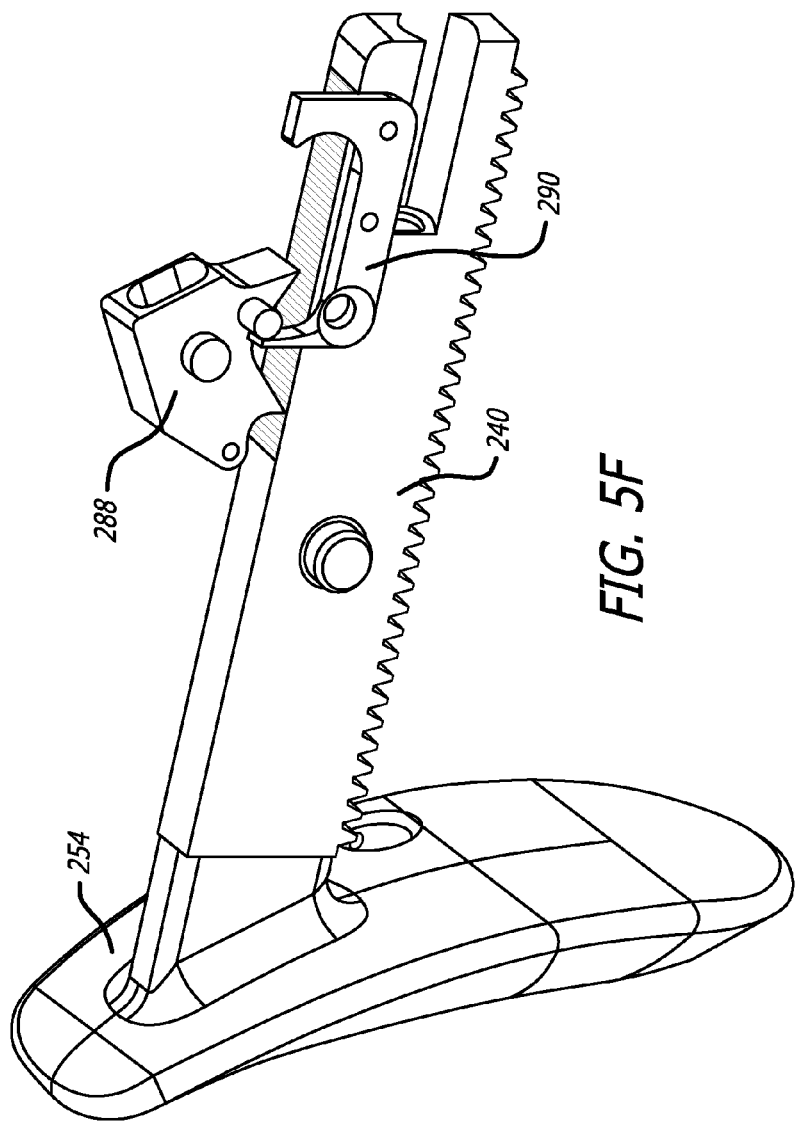

MULTI-ACTUATING TRIGGER ANCHOR DELIVERY SYSTEM

CROSS-REFERENCES TO RELATED APPLICATIONS

This application is a continuation-in-part of copending U.S. patent application Ser. No. 11/671,914, filed Feb. 6, 2007, a continuation-in-part of copending U.S. patent application Ser. No. 11/492,690, filed on Jul. 24, 2006, a continuation-in-part of copending U.S. patent application Ser. No. 11/833,660, filed on Aug. 3, 2007, and a continuation-in-part of copending U.S. patent application Ser. No. 11/134,870, filed on May 20, 2005, the entire disclosures of which are expressly incorporated herein by reference.

FIELD OF THE INVENTION

The present invention relates generally to medical devices and methods, and more particularly to systems and associated methods for manipulating or retracting tissues and anatomical or other structures within the body of human or animal subjects for the purpose of treating diseases or disorders and/or for cosmetic or reconstructive or other purposes.

BACKGROUND OF THE INVENTION

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions). In many of these procedures, surgical incisions are made in the body and laborious surgical dissection is performed to access and expose the affected tissues or anatomical structures. Thereafter, in some cases, the affected tissues or anatomical structures are removed or excised. In other cases, various natural or man made materials are used to lift, sling, reposition or compress the affected tissues.

Benign Prostatic Hyperplasia (BPH)

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1a-adrenergic receptors blockers and 5-alpha-reductase inhibitors. Alpha-1a-adrenergic receptors blockers block that activity of alpha-1a-adrenergic receptors that are responsible for causing constriction of smooth muscle cells in the prostate. Thus, blocking the activity of alpha-1a-adrenergic receptors causes prostatic smooth muscle relaxation. This in turn reduces urethral resistance thereby reducing the severity of the symptoms. 5-alpha-reductase inhibitors block the conversion of testosterone to dihydrotestosterone. Dihydrotestosterone causes growth of epithelial cells in the prostate gland. Thus 5-alpha-reductase inhibitors cause regression of epithelial cells in the prostate gland and hence reduce the volume of the prostate gland which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus the region of urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases are deep enough to cut the surrounding prostate gland tissue including the prostatic capsule. This releases any compression on the bladder neck and causes the bladder neck to spring apart. The incisions can be made using a resectoscope, laser beam etc.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium:yttrium-aluminum-garnet (Nd:YAG) laser is used to ablate tissue by causing coagulation necrosis. The procedure is performed under visual guidance. In HoLEP, a holmium:Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and hence is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland thus reducing the severity of BPH symptoms.

Another example of a minimally invasive procedure for treating BPH symptoms is Transurethral Needle Ablation (TUNA). In this procedure, heat induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland and laser energy is delivered through the distal tip for a desired time. This heats the middle lobe and causes laser induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which in turn causes the prostate gland to shrink. Shrinkage of the prostate gland reduces the degree of squeezing of the urethra by the prostate thus reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra, need for a repeat surgery etc. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%) Typical recovery from TURP involves several days of inpatient hospital treatment with an indwelling urethral catheter, followed by several weeks in which obstructive symptoms are relieved but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries have made their removal quite difficult and invasive.

Thus the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Urinary Incontinence (UI)

Many women experience loss of bladder control following childbirth or in old age. This condition is broadly referred to as urinary incontinence (UI). The severity of UI varies and, in severe cases, the disorder can be totally debilitating, keeping the patient largely homebound. It is usually associated with a cystocele, which results from sagging of the neck of the urinary bladder into or even outside the vagina The treatments for UI include behavioral therapy, muscle strengthening exercises (e.g., Kegel exercises), drug therapy, electrical stimulation of the pelvic nerves, use of intravaginal devices and surgery.

In severe cases of UI, surgery is generally the best treatment option. In general, the surgical procedures used to treat UI attempt to lift and support the bladder so that the bladder and urethra are returned to their normal positions within the pelvic cavity. The two most common ways of performing these surgeries is through incisions formed in the abdominal wall or though the wall of the vagina.

A number of different surgical procedures have been used to treat UI. The names for these procedures include the Birch Procedure, Marshall-Marchetti Operation, MMK, Pubo-Vaginal Sling, Trans-Vaginal Tape Procedure, Urethral Suspension, Vesicourethral Suspension. These procedures generally fall into two categories, namely a) retropubic suspension procedures and b) sling procedures.

In retropubic suspension procedures, an incision is typically made in the abdominal wall a few inches below the navel and a network of connectors are placed to support the bladder neck. The connectors are anchored to the pubic bone and to other structures within the pelvis, essentially forming a cradle which supports the urinary bladder.

In sling procedures, an incision is typically made in the wall of the vagina and a sling is crafted of either natural tissue or synthetic (man-made) material to support the bladder neck. Both ends of the sling may be attached to the pubic bone or tied in front of the abdomen just above the pubic bone. In some sling procedures a synthetic tape is used to form the sling and the ends of the synthetic tape are not tied but rather pulled up above the pubic bone.

The surgeries used to treat UI are generally associated with significant discomfort as the incisions heal and may require a Foley or supra-pubic urinary catheter to remain in place for at least several days following the surgery. Thus, there exists a need in the art for the development of minimally invasive (e.g., non-incisional) procedures for the treatment of UI with less postoperative discomfort and less requirement for post-surgical urinary catheterization.

Cosmetic or Reconstructive Tissue Lifting and Repositioning

Many cosmetic or reconstructive surgical procedures involve lifting, compressing or repositioning of natural tissue, natural tissue or artificial grafts or aberrant tissue. For example, surgical procedures such as face lifts, brow lifts, neck lifts, tummy tucks, etc. have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin and then attaching the repositioned tissues to underlying or nearby structures (e.g., bone, periostium, other muscles) to hold the repositioned tissues in their new (e.g., lifted) position. In some cases excess skin may also be removed during the procedure.

There have been attempts to develop minimally invasive devices and methods for cosmetic lifting and repositioning if tissues. For example, connector suspension lifts have been developed where one end of a standard or modified connector thread is attached to muscle and the other end is anchored to bone, periosteum or another structure to lift and reposition the tissues as desire. Some of these connector suspension techniques have been performed through cannulas or needles inserted through relatively small incisions of puncture wounds.

There remains a need for the development of new devices and methods that may be used for various procedures where it is desired to lift, compress, support or reposition tissues or organs within the body with less intraoperative trauma, less post-operative discomfort and/or shorter recovery times. Further, there is a need for an apparatus and related method which is easy and convenient to employ in an interventional procedure. In particular, there is a need for a substantially automated apparatus which can accomplish accessing an interventional site as well as the assembly and delivery of an interventional device at the site.

The present invention addresses these and other needs.

SUMMARY OF THE INVENTION

Briefly and in general terms, the present invention is directed towards an apparatus and method for deploying an anchor assembly within a patient's body. The apparatus of the present invention includes various subassemblies which are mobilized via a multi-actuating trigger. The operation of the subassemblies is coordinated and synchronized to minimize operator steps and to ensure accurate and precise implantation of a single or multiple anchor assemblies.

In one embodiment, the multi-actuating trigger anchor delivery system of the present invention includes a handle assembly operatively connected to a core assembly. The handle assembly can be permanently connected to the core assembly or the core assembly can be attachable to the handle assembly such that the handle can be used with multiple core assemblies over time. The core assembly houses a plurality of components for constructing anchor assemblies. The handle assembly further includes a rocker arm assembly, a spool or rotary assembly and a trigger assembly which cooperate to accomplish the various functions of the delivery system. In particular, in one aspect the spool assembly includes one or more spring assemblies loaded with sufficient energy to advance and deploy components for multiple anchor assemblies. The spool assembly is particularly advantageous in that it allows several anchor assemblies of at least 6 cm of length each to be stored in a relatively small device that fits in a user's hand. It is further advantageous in that it allows the physician to insert the device only once into the patient to deliver multiple anchor assemblies at different locations before having to withdraw the device. In another aspect the rocker arm assembly includes one or more spring assemblies loaded with sufficient energy to advance and retract the core assembly a plurality of times. The delivery system further includes a reset assembly that may recharge one or more springs within the handle and core assemblies. It can be appreciated that rocker arm and spool housing actuation can be accomplished by manual advancement, elastomers, compressed gas, or motor.

In one particular aspect, the present invention is directed towards a delivery device which accomplishes the delivery of a first or distal anchor assembly component at a first location within a patient's body and the delivery of a second or proximal anchor assembly component at a second location within the patient. The device also accomplishes imparting a tension during delivery and a tension between implanted anchor components as well as cutting the anchor assembly to a desired length and assembling the proximal anchor in situ. The procedure can be viewed employing a scope incorporated into the device. Also, the delivery device can be sized and shaped to be compatible with a sheath in the range of 18 to 24F, preferably a 19F sheath.

Additionally, in a contemplated embodiment of a multi-actuating trigger anchor delivery system, a first trigger pull results in a needle assembly being advanced within a patient to an interventional site. A second trigger pull accomplishes the deployment of a first anchor component of an anchor assembly at the interventional site and a third trigger pull facilitates withdrawing the needle assembly. A fourth trigger depression facilitates the assembly and release of a second component of an anchor assembly at the interventional site. A reset assembly is further provided to reset aspects of the delivery system.

The present invention also contemplates a reversible procedure as well as an anchor assembly with sufficient visibility when viewed ultrasonically, by xray, MRI or other imaging modalities. In one aspect, the implant procedure is reversible by severing a connector of an anchor assembly and removing an anchor of the anchor assembly such as by so removing a proximally placed anchor previously implanted in an urethra. Moreover, the anchor assemblies can be formed of structures facilitating ultrasound viewing or other imaging modalities.

The anchor assembly can be configured to accomplish retracting, lifting, compressing, supporting or repositioning tissue within the body of a human or animal subject. Moreover, the apparatus configured to deploy the anchor assembly as well as the anchor assembly itself are configured to complement and cooperate with body anatomy. Further, the anchor assembly may be coated or imbedded with therapeutic or diagnostic substances, in particular Botulinum toxin, or such substances can be introduced into or near an interventional site by the anchor deployment device or other structure.

In another aspect, structure of the anchor assembly is designed to invaginate within or complement tissue anatomy to thereby facilitate healing and minimize infection risk or risk of calculus formation. Moreover, the anchor delivery device includes structure to form desired angles between an extended position of the needle assembly relative to the device. Additionally, it is contemplated that a distal end portion of the anchor delivery device be configured to facilitate the testing of the effectiveness of positioning of an anchor assembly. In this regard, the distal end portion is configured in a manner to allow the device operator to mimic the effect a second anchor member will have prior to anchor delivery.

In one embodiment, the anchor delivery device includes a handle assembly with a trigger attached thereto. The trigger is associated with a body of the handle assembly and is operatively attached to the needle assembly and structure that advances the first anchor member. The trigger is also operatively associated with structure that accomplishes assembling first and second parts of the second anchor member to each other and to the connector member or by forming a single-piece second anchor member around the connector member. Additionally, the handle assembly is equipped with structure that is configured in one contemplated embodiment, to effect the cutting of the anchor assembly to a desired length and deployment of the structure at an interventional site.

In a specific embodiment, the anchor delivery device includes a generally elongate tubular housing assembly member extending distally from a handle assembly including a trigger. The proximal end of the handle assembly is equipped with mounting structure configured to receive a telescope or other endoscopic viewing instrument. A bore sized to receive the telescope extends distally through a body of the handle assembly and continues through an outer tubular cover member forming the generally elongate member. Housed within the tubular housing assembly are a telescope tube having an interior defining a distal section of the bore sized to receive the telescope, an upper tubular member assembly sized to receive a plurality of first components of the second anchor member and a needle housing configured to receive the needle assembly. Moreover, the generally elongate tubular housing includes a terminal end portion defined by a nose assembly which retains a plurality of second components of the second anchor members.

Additionally, in a preferred embodiment the first anchor member includes a tubular portion, a mid-section and a tail portion. The tail portion of the member further includes a connector section which acts as a spring. A terminal end portion of the tail is further contemplated to have a surface area larger than the connector section to provide a platform for engaging tissue.

Further, in the preferred embodiment, one component of the second anchor member is embodied in a pin having a first distal end equipped with a pair of spaced arms and a second proximal end including grooves facilitating pushability.

Moreover, various alternative methods of use are also contemplated. That is, in some applications of the invention, the invention may be used to facilitate volitional or non-volitional flow of a body fluid through a body lumen, modify the size or shape of a body lumen or cavity, treat prostate enlargement, treat urinary incontinence, support or maintain positioning of a tissue, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires retracting, lifting, repositioning, compression or support.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1A is an elevation view, depicting a multi-actuating trigger anchor delivery system of the present invention;

FIG. 1C is a rotated elevation view, depicting the system of FIG. 1B without the handle case;

FIG. 1D is a detail view, depicting a distal end portion of the device of FIG. 1C;

FIG. 2A is a perspective view, depicting a core assembly of the multi-actuating trigger anchor delivery system of FIG. 1B;

FIG. 2B is a perspective view, depicting a shaft assembly of the core assembly of FIG. 2A;

FIG. 5E is an enlarged view, depicting the double pawl in a default position;

FIG. 5F is an enlarged view, depicting the double pawl after trigger depression;

FIG. 5G is an enlarged view, depicting the bell crank frame including a bell crank follower;

DETAILED DESCRIPTION OF THE PREFERRED EMBODIMENTS

Figure 1B:
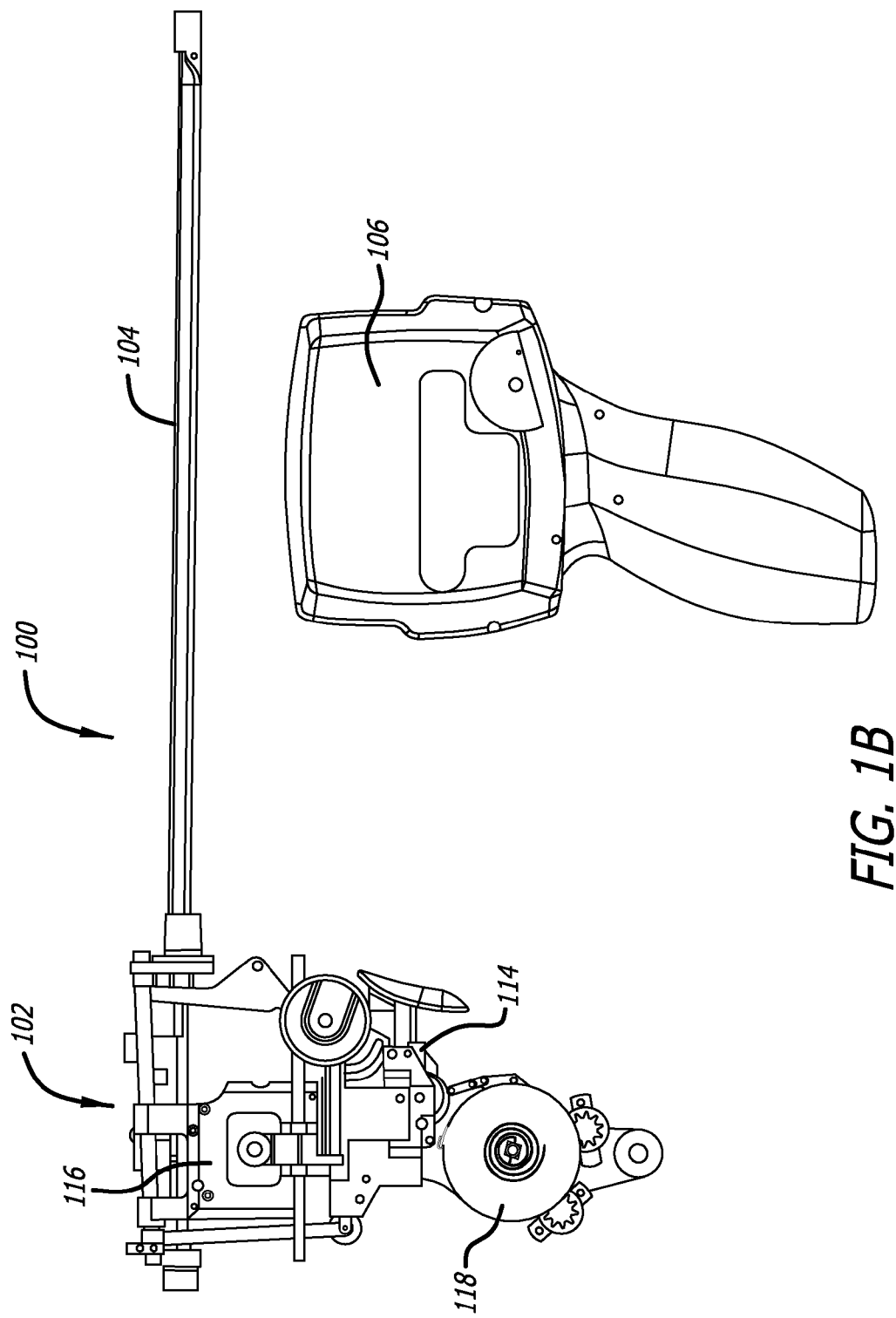
FIG. 1B is an elevation view, depicting the system of FIG. 1A with the handle case removed.

Turning now to the figures, which are provided by way of example and not limitation, the present invention is embodied in a device configured to deliver anchor assemblies within a patient's body. As stated, the present invention can be employed for various medical purposes including but not limited to retracting, lifting, compressing, supporting or repositioning tissues, organs, anatomical structures, grafts or other material found within a patient's body. Such tissue manipulation is intended to facilitate the treatment of diseases or disorders. Moreover, the disclosed invention has applications in cosmetic or reconstruction purposes or in areas relating the development or research of medical treatments.

In one particular aspect, the anchor assembly of the present invention is contemplated to be formed of a structure which is visible by ultrasound. Accordingly, the anchor assembly can be viewed during ultrasonic body scans such as during normal trans-rectal ultrasound when a medical professional is conducting diagnoses or treatment associated with conditions like prostate cancer.

In such applications, one portion of an anchor assembly is positioned and implanted against a first section of anatomy. A second portion of the anchor assembly is then positioned and implanted adjacent a second section of anatomy for the purpose of retracting, lifting, compressing, supporting or repositioning the second section of anatomy with respect to the first section of anatomy as well as for the purpose of retracting, lifting, compressing, supporting or repositioning the first section of anatomy with respect to the second section of anatomy. It is also to be recognized that both a first and second portion of the anchor assembly can be configured to accomplish the desired retracting, lifting, compressing, supporting or repositioning of anatomy due to tension supplied thereto via a connector assembly affixed to the first and second portions of the anchor assembly.

Referring now to FIGS. 1A-D, there is shown one embodiment of a multi-actuating trigger anchor delivery system 100 of the present invention. This device is configured to include structure that is capable of both gaining access to an interventional site as well as assembling and implanting one or more anchor assemblies within a patient's body. In one aspect, the device 100 is configured to assemble and implant four anchor assemblies. The device is further contemplated to be compatible for use with a 19F sheath. The device additionally includes structure configured to receive a conventional remote viewing device (e.g., an endoscope) so that the steps being performed at the interventional site can be observed.

The multi-actuating trigger anchor delivery device 100 includes a handle assembly 102 connected to an elongate tissue access assembly 104. The elongate tissue access assembly 104 houses components employed to construct a plurality of anchor assemblies.

The anchor delivery system 100 further includes a number of subassemblies. A handle case assembly 106 including mating handle halves which encase the handle assembly 102. The handle assembly 102 is sized and shaped to fit comfortably within an operator's hand and can be formed from conventional materials. Windows 107 can be formed in the handle case assembly 106 to provide access to internal mechanism of the device so that a manual override is available to the operator in the event the interventional procedure needs to be abandoned. A core assembly 110 extends through the handle assembly 102, and includes the components defining the elongate tissue access assembly 104.

The handle assembly 102 further includes a trigger system assembly 114, a spool assembly 116 and a rocker arm assembly 118. These assemblies cooperate to accomplish gaining access to an interventional site as well as the assembly and implantation of an anchor assembly at the interventional site.

Moreover, a terminal end portion 119 of the anchor delivery system includes a distal tip assembly 128 shaped to provide an atraumatic surface as well as one which facilitates desired positioning of components of an anchor assembly (See FIG. 1D). That is, by including structure that can mimic the ultimate position of a proximally oriented component of an anchor assembly, an operator can test the effect of the anchor assembly prior to implantation. Once the operator confirms that the subject anchor component will be positioned as desired, the implantation of the anchor is then undertaken and accomplished.

Figure 2C:
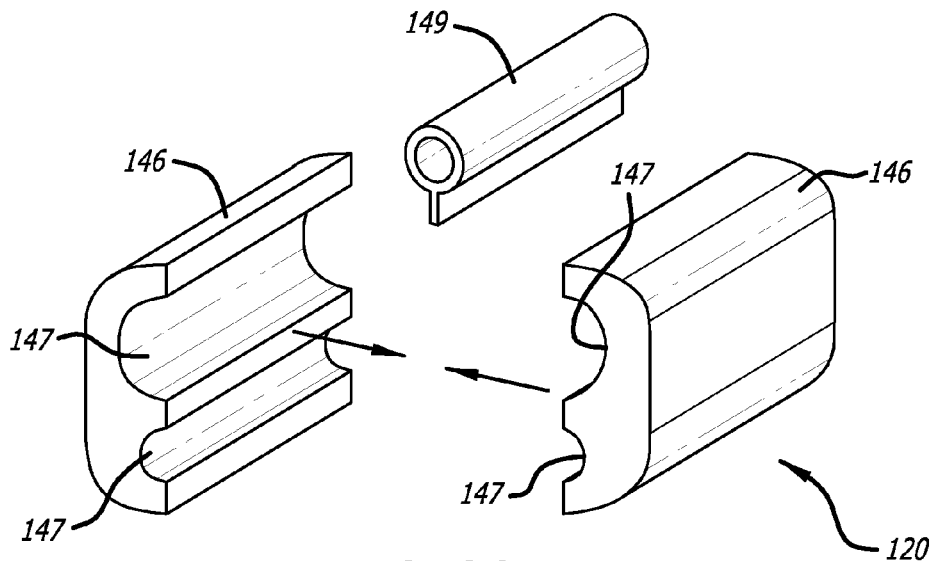
FIG. 2C is a perspective view, depicting another approach to forming sections of a shaft assembly.

Turning now to FIGS. 2A-2B, there is shown a core assembly 110. As stated, the core assembly 110 retains the components necessary to assembling a plurality of anchor assemblies. The core assembly 110 includes a shaft assembly 120, a ratchet block assembly 122, an outer cover block assembly 124, a stop assembly 126 and a distal tip assembly 128. In one embodiment, the core assembly 110 is permanently attached to the handle assembly 102. In an alternative embodiment, the core assembly is temporarily attached to the handle assembly to allow for reuse of the handle assembly and disposal of the core assembly.

With specific reference to FIG. 2B, the shaft assembly 120 further includes an elongate endoscope tube 130 which extends from a scope rear mount 132 through a front plate assembly 134 and distally to a terminal end 136 of the shaft assembly 120. The endoscope tube accommodates a removable endoscope. Additionally, extending distally from the front plate assembly 134 and arranged generally parallel to the endoscope tube 130 is a pusher tube assembly 138 including an anchor alignment tube for maintaining alignment of anchor components within the tube. Another elongate tubular housing 140 configured to receive a needle assembly also extends longitudinally from the front plate assembly 134. The front plate assembly further includes a sheath sealing plate 143 which is configured to create a seal between and amongst the elongate components extending therethrough (See FIG. 2A).

Figure 2D:
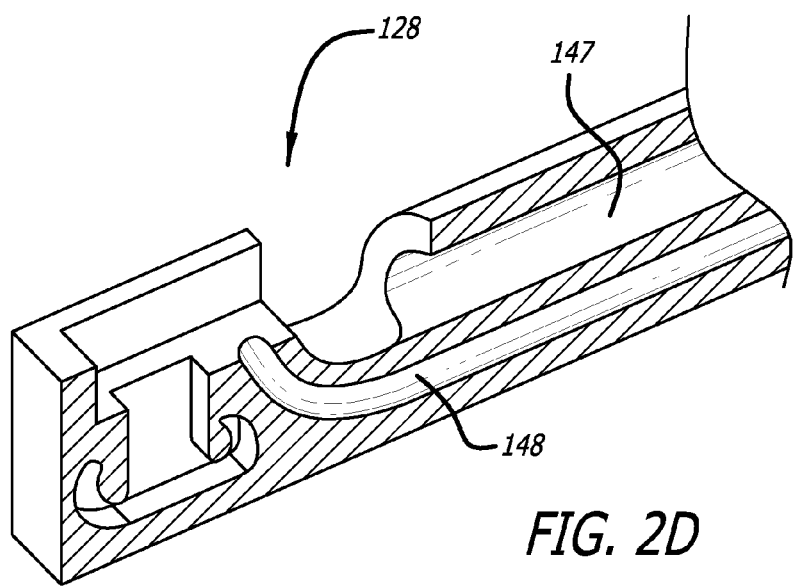
FIG. 2D is a perspective view, depicting an alternate approach to structure of a distal end portion of the system.
Figure 2E:
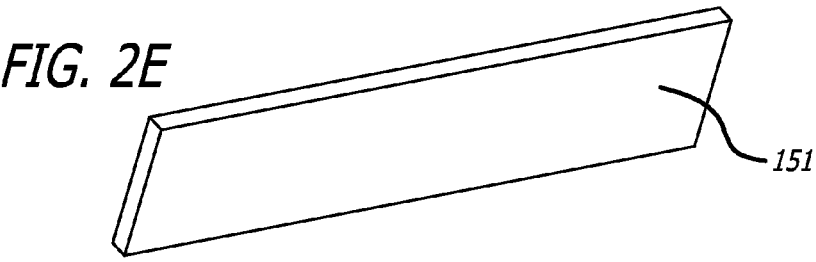
FIG. 2E is a perspective view, depicting a first step in forming an alternative approach to a shaft assembly.
Figure 2F:
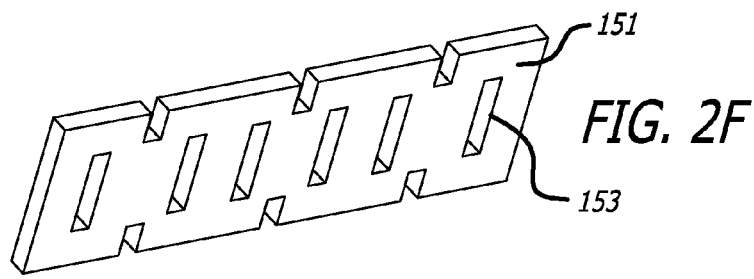
FIG. 2F is a perspective view, depicting a second step in forming an alternative approach to a shaft assembly.
Figure 2H:
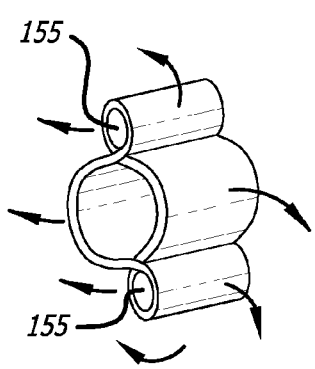
FIG. 2H is a perspective view, depicting a fourth step in forming an alternative approach to a shaft assembly.
Figure 2G:
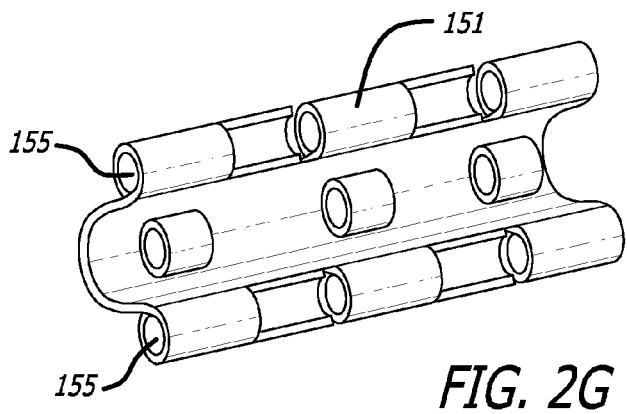
FIG. 2G is a perspective view, depicting a third step in forming an alternative approach to a shaft assembly.

In an alternate approach (See FIGS. 2C-D), it may be possible to have the shaft assembly 120 constructed with mating extruded halves 146 to function equivalent to the current trilumen shaft assembly.

Further, the distal tip assembly 128 may be integral to one half of the elongate shaft. One or both of the halves 196 will have elongate channels 147 that may be semi-circular or even square shared, but would functionally constrain and house both the telescope and needle assembly in their unique channels. In a simple construction the second half may merely close off the open channels 147 to constrain the telescope and needle assembly.

The distal curved needle housing 148 that vectors the needle tip through the urethral wall (or other body lumen) is integral to one or both of the halves where if biased to one half the guiding surface may provide more intimacy and improved performance.

The pin storage tube 149 may be a Nitinol or stainless steel tube that is either or both laser cut or laser welded with assembly features. Such assembly features may be folded over tabs or points that may be captured between the shaft extrusion assembly, thus integrating the parts to functionally act like the current invention at a lower complexity or cost.

Figure 2I:
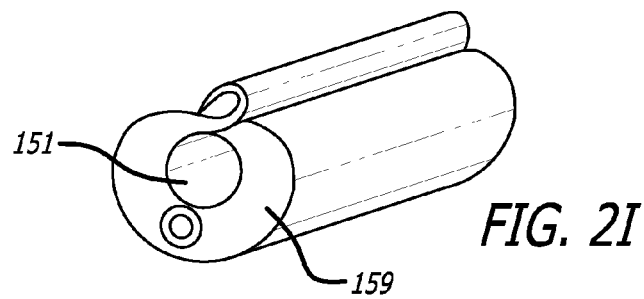
FIG. 2I is a perspective view, depicting a fifth step in forming an alternative approach to a shaft assembly.

In a yet further approach, an alternative construction of the shaft assembly 120 may incorporate a stamped metal element that is a single elongate strip 151 of thin wall stainless steel (See FIGS. 2E-I). Fenetrations, castellations or tabs 153 (FIG. 2F) may be stamped around the edges so as to be formed 155 (FIGS. 2G and H) to retain hypotubes adjacent to each other at distinct points that may later be insert molded over or inserted into a simple plastic injected molded shell 159 (FIG. 2I). The metal formed insert would provide more structural stiffness and accuracy in assembly in contrast to singular plastic shaft assembly. Thus, the formed strip may appear as a wave pattern with intermittent tabs formed in the opposite direction of the locally formed strip resulting in a plurality of concentric paths that hypotubes may be assembled through and fixed into position.

In one particular aspect, the core assembly 120 is further equipped with guide rails 145 which both lend structural support to the assembly as well as guides along which various of the subassemblies are translated with the actuation of the trigger assembly. Also, the core assembly 120 includes a longitudinally translatable outer tube assembly 142 (See FIG. 2A), a distal end of which is received within the distal tip assembly 128 (See also FIG. 1D). As described in more detail below the distal tip assembly houses a plurality of rings or cylinders and a spring biased feeder.

With reference to FIGS. 3A-E, the rocker arm assembly 118 of the handle assembly is described as is its interaction with the trigger system assembly 114. The rocker arm assembly interacts with the multi-actuating trigger assembly to convert each single trigger pull into four different actions of the anchor delivery system 100.

Figure 3A:
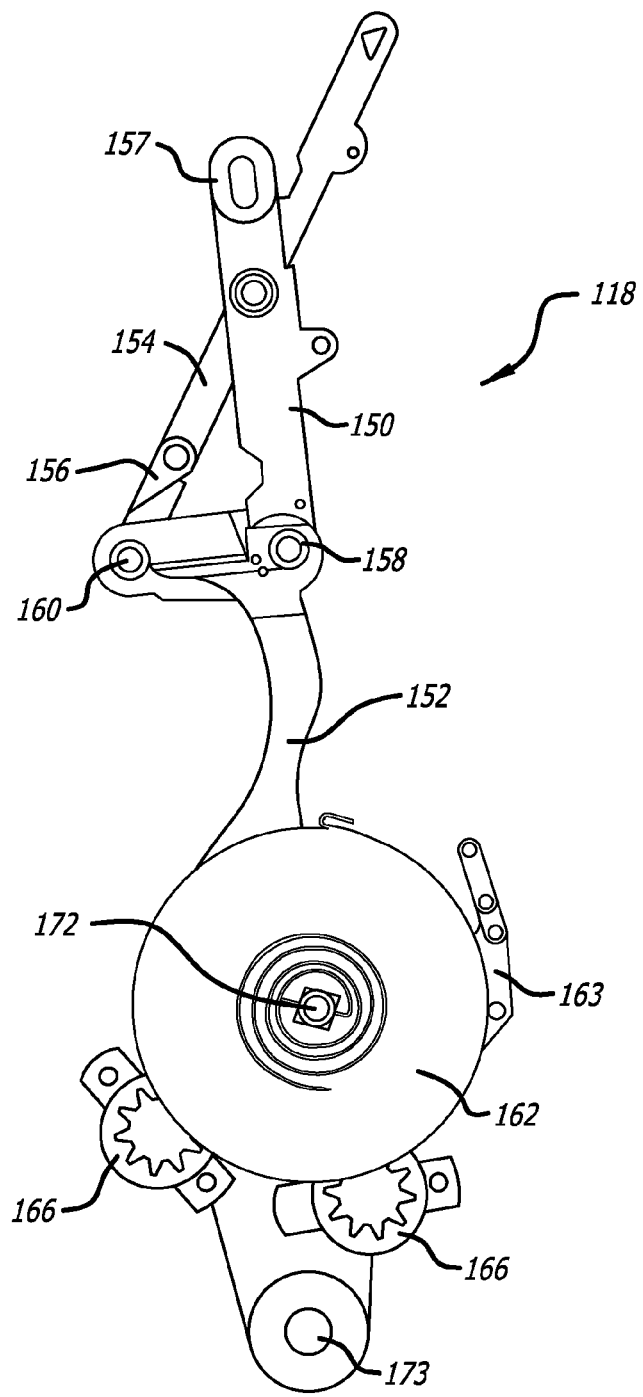
FIG. 3A is an elevation view, depicting a rocker arm assembly of the multi-actuating trigger anchor delivery system of FIG. 1B.
Figure 3B:
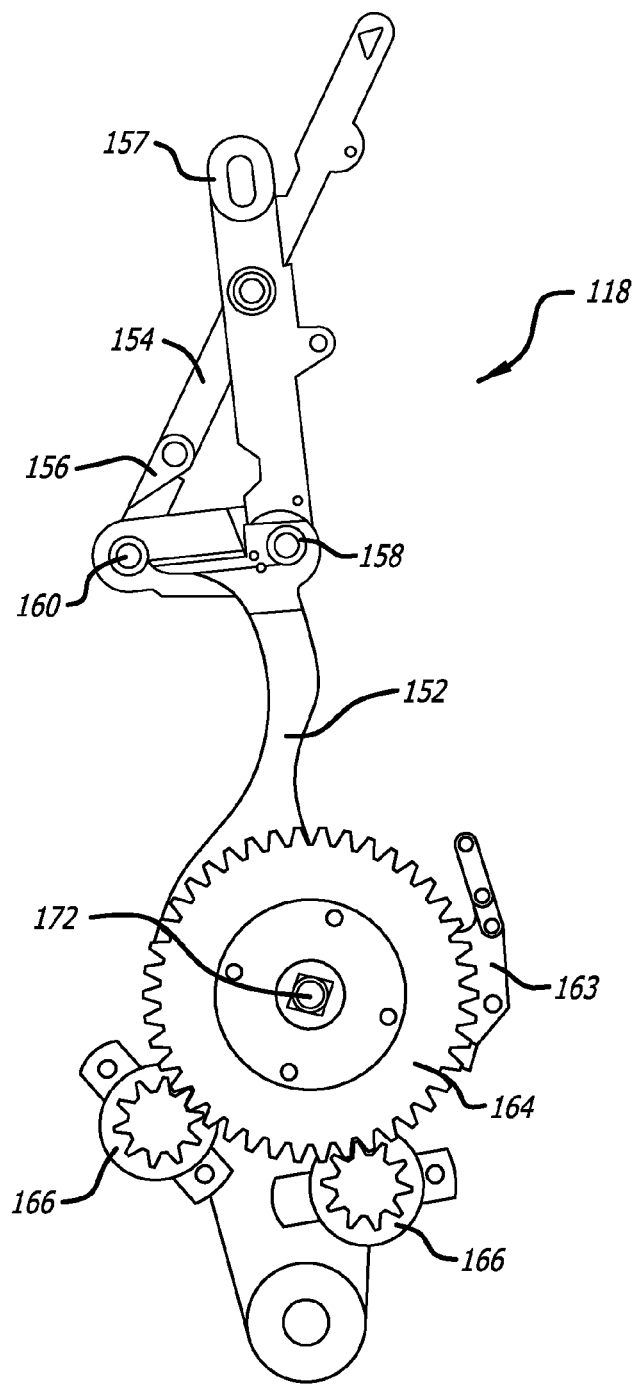
FIG. 3B is an elevation view, depicting the rocker arm assembly of FIG. 3A with a crank spring assembly removed.
Figure 3C:
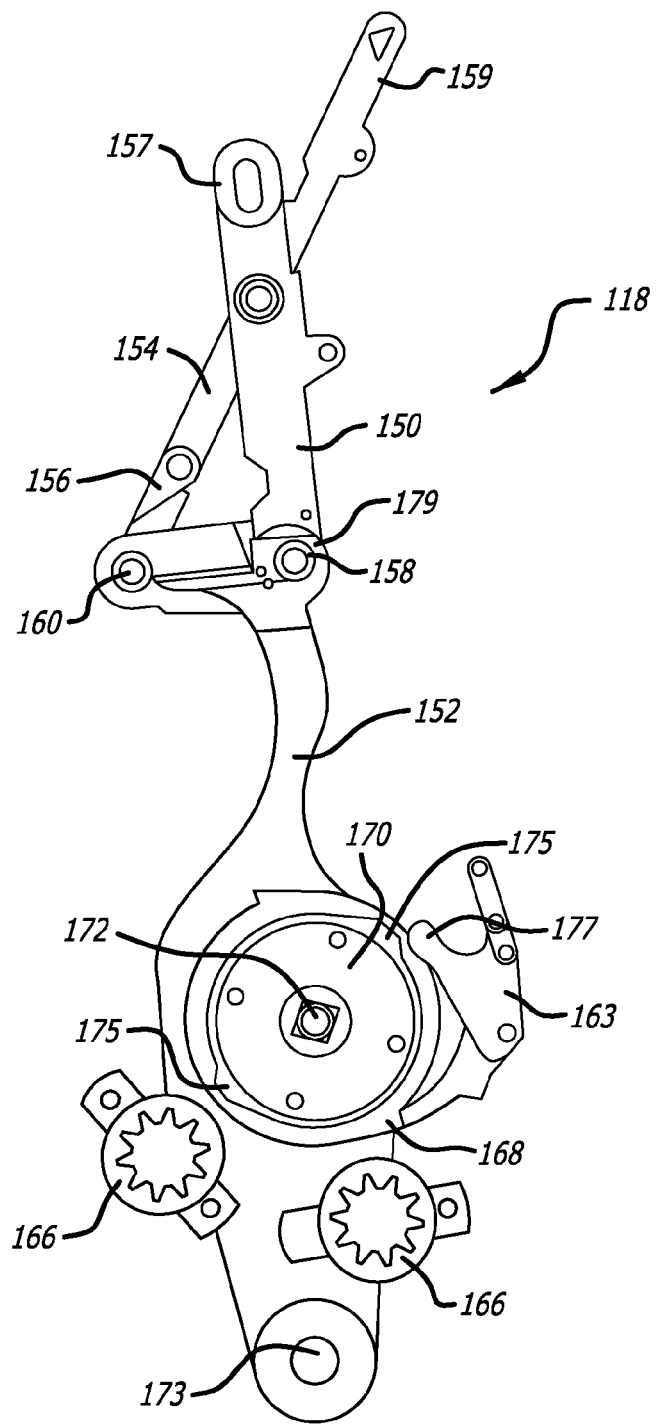
FIG. 3C is an elevation view, depicting the rocker arm assembly of FIG. 3B with a large crank gear removed.
Figure 3D:
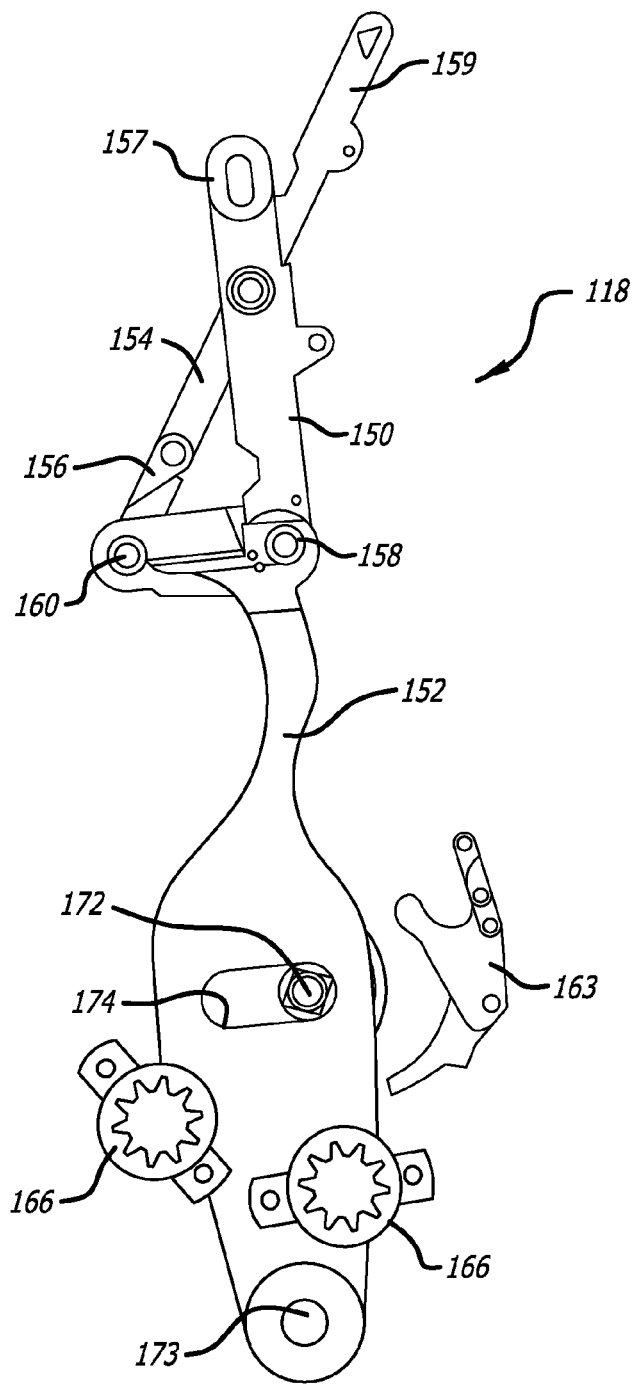
FIG. 3D is an elevation view, depicting the rocker arm assembly of FIG. 3C with a rocker arm ratchet removed.
Figure 3E:
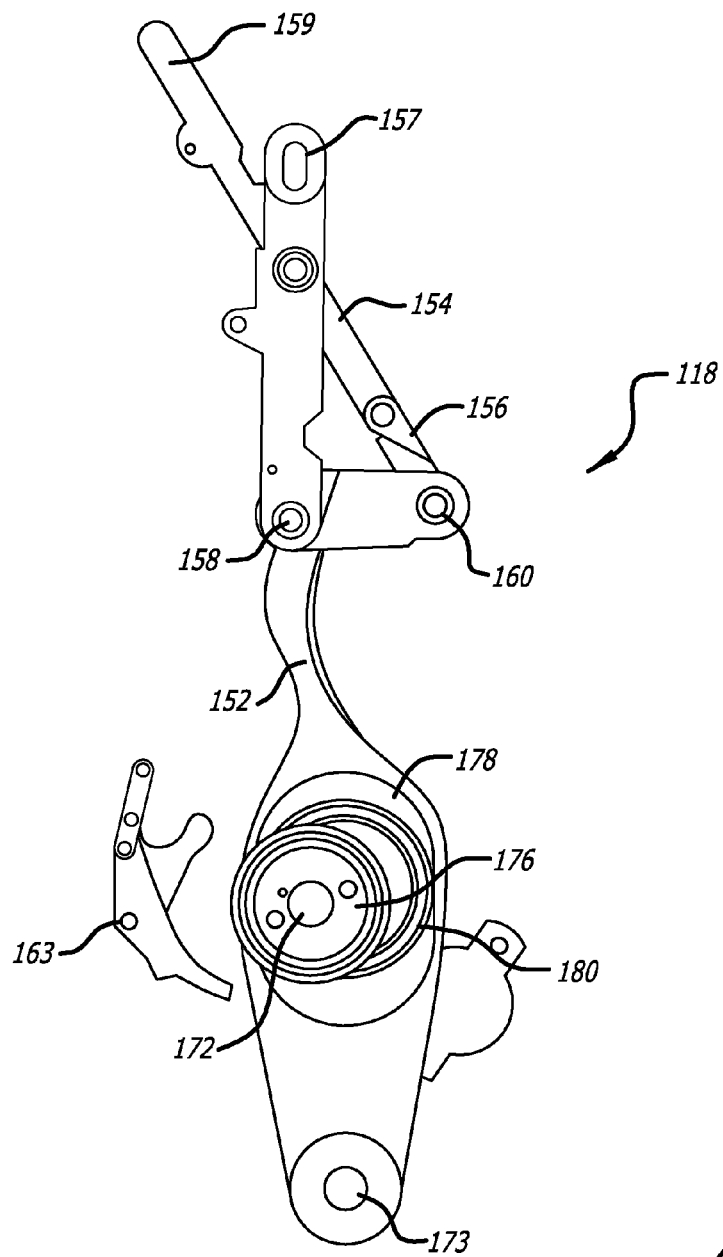
FIG. 3E is a rotated elevation view, depicting the rocker arm assembly of FIG. 3D.

With particular reference now to FIGS. 3D and 3E, it is to be appreciated that the rocker arm assembly 118 is grounded at two points, at a rocker arm pivot point 173 and at a crank shaft 172. Both of these elements are free to rotate, but not translate. A mid-section of the assembly 118 is characterized by a scotch yoke structure. As is conventionally known, the scotch yoke can be employed to convert rotational motion into linear motion. Here, the rocker arm assembly 118 is powered by a spring assembly 162 and through interaction between the trigger assembly 114 and a rocker pawl 163, this spring assembly 162 is selectively activated to effect rotation of a crank bearing assembly 176 which is attached in an off-center position to a cam bearing assembly 180. This in turn causes the cam bearing 180 to be guided along barriers defined by an oval recess 178 formed in a lower rocker arm portion 152 of the rocker arm assembly 118. Such action results in the rocker arm assembly 118 to pivot at its lower end about the rocker pivot point 173 and at its top end, linear motion results. This linear motion is employed to selectively translate the spool assembly 116 longitudinally.

In one particular aspect, the rocker arm assembly 118 includes an upper rocker arm assembly 150, a lower rocker arm assembly 152 and upper 154 and lower 156 break away links. A terminal end 157 of the upper rocker arm 150 is provided with a slot which slideably engages complementary structure on the spool assembly 116, the interconnection of which facilitates the transition of articulating movement of the rocker arm assembly into longitudinal motion of the spool assembly 116. Further, a spring (not shown) connects the upper rocker arm assembly 150 to the upper break away link 154. The damper assemblies 166 function as a mode of speed modulation which governs the action of the large gear 164 and thus the action of the rocker arm assembly 118 in response to the trigger assembly 114. The damper assemblies 166 are filled with a selected amount of fluid having a known viscosity. The amount and viscosity of the fluid can be varied to achieve the desired dampening effect. In the approach contemplated, the lower rocker arm assembly 152 includes a pair of spaced pivot points 158, 160 to which the upper rocker arm 150 and the lower break away link 156 are pivotably connected. Further, a pivoting connection exists between the upper 154 and lower 156 break away links. The rocker arm assembly further includes a crank spring assembly 162 mounted on the lower rocker arm assembly 152.

With the crank spring assembly 162 removed (See FIG. 3B), the engagement between a large gear 164 and a pair of spaced damper assemblies 166 can be better appreciated. Configured on the same side of the lower rocker arm assembly 152 and adjacent to the large gear 164 is a rocker arm ratchet 168 (See FIG. 3C). A crank arbor 170 is positioned on an outside surface of the rocker arm ratchet 168. It is to be recognized that as a result of the actuation of the trigger assembly the crank spring assembly 162 drives the crank 170 counter clockwise and thereby moves the rocker arm assembly 118 forward and backwards about rocker arm pivot point 173.

Figure 3F:
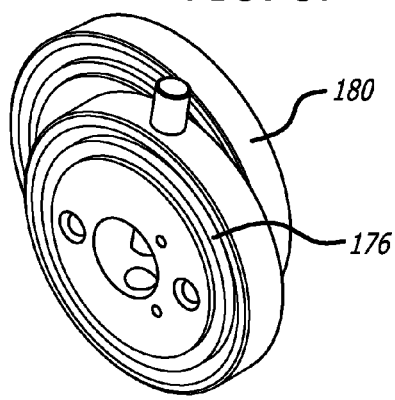
FIG. 3F is an isometric view, depicting the juxtaposition of the crank bearing assembly and the cam bearing assembly.

Each of the rocker arm ratchet 168 and crank arbor 170 (See FIG. 3C) are configured upon a centrally configured crank shaft 172, the crank shaft passing through a curved slot 174 formed in the lower rocker arm 152 (See FIG. 3D). On the opposite side of the lower rocker arm assembly 52 and also mounted on the crank shaft 172 is an eccentrically arranged crank bearing assembly 176 (See FIG. 3E). See also FIG. 3F which depicts the juxtapositioning of the crank bearing assembly 176 and the cam bearing assembly 180.

Moreover, as stated, configured on a portion of the crank bearing 176 and within an oval recess 178 formed in the lower rocker arm 152 is a cam bearing 180. The crank bearing 176 is rotationally coupled to the crank shaft 172 and thereby converts the rotational motion to linear motion at the terminal end 157 of the upper rocker arm 150 as in a scotch yoke. Additionally, in operation the crank spring assembly 162 is kept from unloading by a spring-loaded, rocker pawl 163 (See FIG. 3C), the rocker pawl being tripped during certain stages of trigger activations. In this regard, the assembly is equipped with a no-skip feature. That is, as best seen in FIG. 3C, the rocker arm ratchet 168 is equipped with a no-skip cam surface 175. As the trigger assembly causes one end of the rocker pawl 163 to disengage from the rocker arm ratchet 168 and the rocker arm ratchet 168 rotates in response to the energy provided by the crank spring assembly, a no skip link cam follower 177 engages the no skip cam surface 175. This action results in properly positioning the components to prevent pawl skipping and double needle deployment due to high crank speed and low reaction speed of the pawl 163 after tripping. A torsion spring 179 is provided at the vertically positioned pivot point 158 to prevent high speeds in the lower rocker arm 152 to help control the speed of rotation of the rocker arm ratchet 168. As can be seen in the FIGS., the rocker arm ratchet 168 includes only two teeth which are alternatively engaged by the rocker arm pawl assembly 163. These teeth are spaced such that an advance stroke occurs on one pawl trip and a retract stroke occurs on the next pawl trip.

Additionally, during the stage of activation of the trigger assembly when the terminal end 159 hits the stop assembly 126 and there is rotation of the lower rocker arm assembly 152, the upper 154 and lower 156 break away links break in that the pivot joint between the two members translates inwardly toward the upper rocker arm assembly 150. This breakaway action allows the lower rocker arm 152 to continue through an entire stroke while the upper breakaway link rocker arm 154 rotates in an opposite direction such that no further translation is imparted upon the terminal end 157, the spool assembly 116 and the needle assembly connected thereto stop at a depth set by the stop assembly 126. Accordingly, this mechanism controls the movement of the spool assembly as more fully described below.

Finally, the windows 107 formed in the handle 106 can be used to also access portions of the rocker assembly 118 or the handle housing 106 itself can be removed to do so. Thus, the crank bearing assembly 176 can be manually turned to accomplish desired movement of components turning the rocker arm assembly. A bailout feature is thus provided to, for example, retract the needle assembly.

Figure 4A:
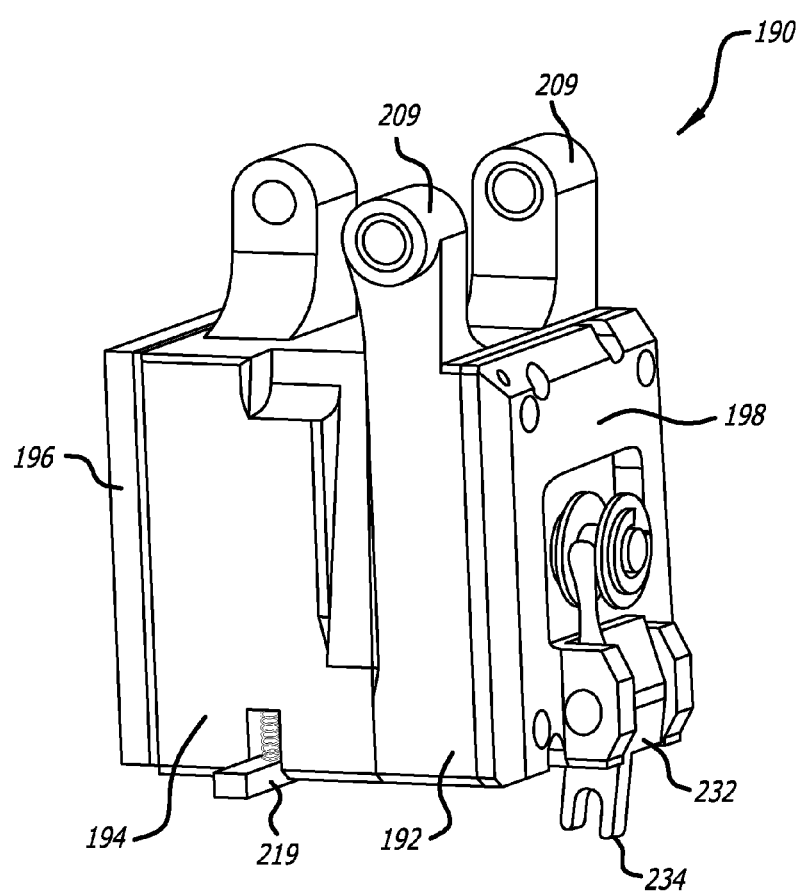
FIG. 4A is a rotated perspective view, depicting the spool assembly of the multi-actuating trigger anchor delivery system of FIG. 1B.
Figure 4B:
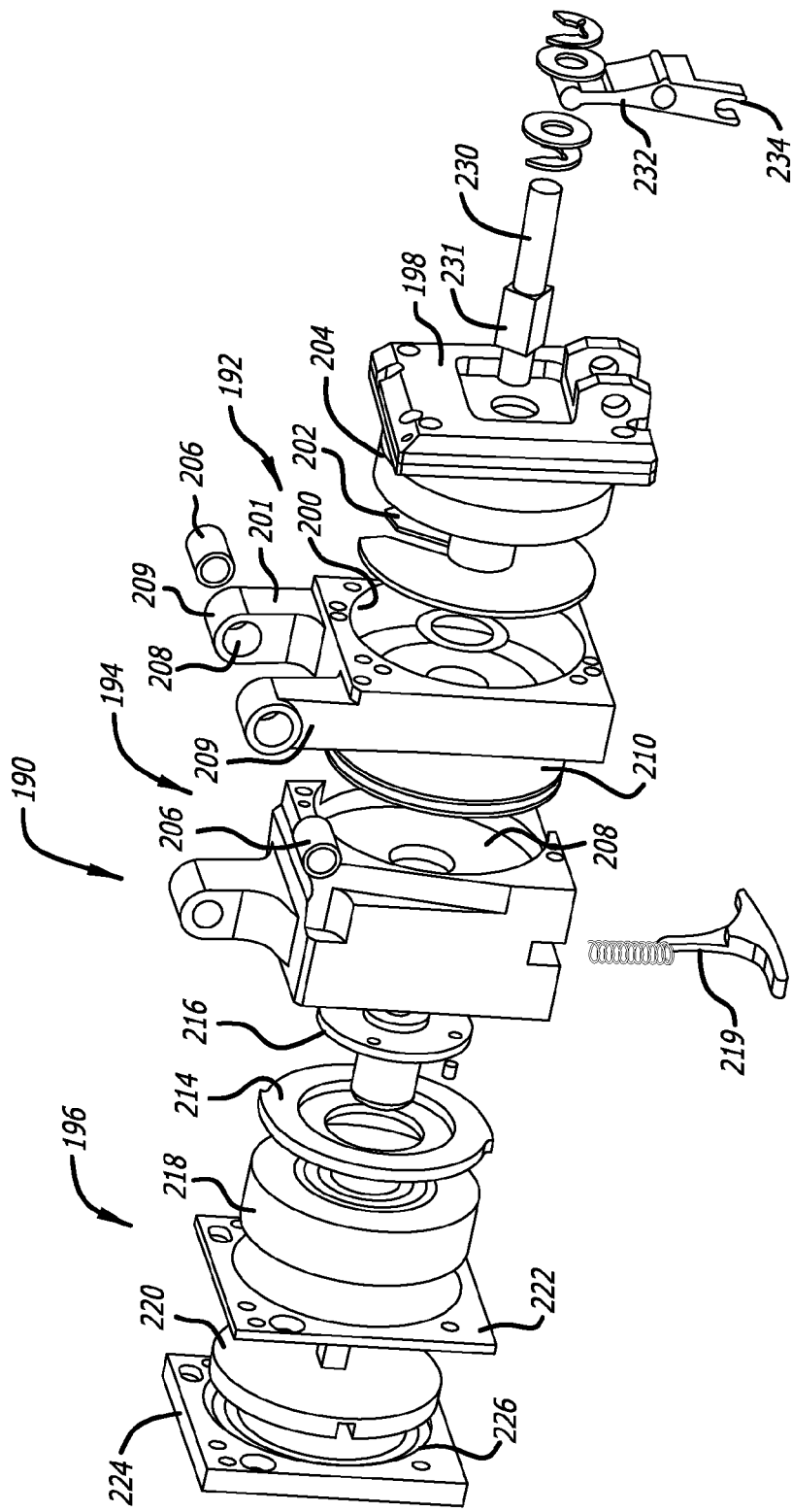
FIG. 4B is an exploded view, depicting the spool assembly of FIG. 4A.

Turning now to FIGS. 4A and 4B, there is shown a spool assembly 190. The spool assembly is used to push anchor components from the distal end of the anchor delivery device. The rotary mechanism is particularly advantageous in that it allows several anchor assemblies (e.g. four) with approximately 6 cm (corresponds to ½ of circumference of spool) of connector material such as monofilament PET, 0.015 inch diameter between anchors to be stored in a relatively small device that fits in a user's hand. The spool assembly 190 further includes a tension housing assembly 192, a deploy housing assembly 194, and a damper assembly 196.

The tension housing assembly 192 is configured between a housing cap 198 and the deploy housing assembly 194. The spool assembly 190 further includes a circular recess 200 in the tension housing 201 that is sized and shaped to receive a tension arbor with tension spring. In one approach, the tension spring applies one pound of tension to an implant component once the component has been deployed, but less and more tension can be provided as desired. Further, the assembly is configured so that no tension is applied prior to implantation. Also, the tension spring 204 is loaded up to ½ turn as the needle is retracted, thereby tensioning the suture, and then it unloads, thereby retracting the capsular anchor assembly after the urethral anchor is delivered and the suture is cut. The housing cap 198 retains the tension arbor 202 and tension spring 204 within the circular recess 200. Moreover, the spool housing 190 may further include bushings 206 which fit within holes 208 formed through a pair of spaced arms 209 extending from a top of the tension housing assembly 192. The bushings 206 provide a surface for smooth movement along rails 140 of the core assembly 110 (See FIG. 2A).

As shown in FIG. 4B, the deploy housing assembly 194 is configured with a first circular recess 208 facing the tension housing assembly 192. The first recess 208 is sized and shaped to receive a spool assembly with a central shaft 230. The adjacently arranged tension housing assembly 192 retains the spool assembly 210 within the first recess 208. It is to be recognized that a wire (not shown) is wound around the spool assembly 210. This wire is bonded to an implant (anchor) assembly and transmits the driving force and tensioning torque from the spool assembly 190 to the implant components during the deployment of an anchor assembly. A second recess (not shown) is formed in an opposite side of the deploy housing assembly 194 which faces the damper assembly 196. This second circular recess is sized and shaped to receive a spool ratchet disc 214 sandwiched between a deployment arbor with central shaft 216 and a suture deploy spring 218 which is initially fully loaded with enough energy to drive four distal anchor members out of the needle. The damper assembly 196 retains the spool ratchet disc 214, deployment arbor 216 and suture deploy spring 218 within the second recess of the deploy housing assembly 194. The deploy housing assembly 190 is further equipped with a spring loaded suture deploy pawl assembly 219 received within a recess formed in a bottom lateral surface of the housing 194. It is to be noted that the spool ratchet disc 214 is coupled to the deployment arbor 216 in a manner such that the deployment spring (not shown) is refrained from unloading until the deploy pawl 219 is tripped. The no-skip mechanism again here prevents double deployments if the primary mechanism moves faster than the pawl's 219 response times.

The damper assembly 196 includes a damper body 224 and a damper rotor 220 which have multiple interleaved circular surfaces such that the damper rotor 220 can rotate within the damper body 224. The gaps between the interleaved surfaces are filled with viscous dampening fluid (not shown). The damper rotor 220 has a square peg which positively and permanently engages into the square port of the deploy arbor 216, thereby providing speed modulation to the deploy spring 218 as it is unloaded to deploy the distal anchor member out of the needle.

A central shaft 230 is configured through the tension housing assembly 192 and extends to within the deploy housing assembly 194. A square section 231 of the shaft 230 is always engaged in the spool assembly 190 with either the deployment arbor 216 or the tension arbor 202. Thus, when the deployment pawl 219 is released, the square section of the central shaft 230 is engaged with the deployment arbor 216 and is disengaged from the tension arbor 202. This allows the deployment spring to drive the spool 210 180 degrees. A throwout arm assembly 232 is retained on the central shaft 230 and includes a forked substructure 234 configured to engage complementing structure of the trigger assembly 114. The throwout arm assembly is activated by the trigger assembly to translate the shaft 230 between the deployment arbor 216 and the tension arbor 202 at desired time points in the delivery process.

The window 107 formed in the handle case assembly 106 (See FIG. 1A) can be configured to provide convenient direct access to components of the spool assembly 190 in the event any of the components become stuck. For example, force can be directly applied to the throwout arm 232 so that the shuttle action of the assembly can be facilitated.

With reference now to FIGS. 5A-E, the components of the trigger system assembly 114 are described. The trigger assembly 114 includes a trigger rack assembly 240, a trigger cam assembly 242, a lower cam assembly 244 and a bell crank assembly 246, each of which are attached or separately associated with a mounting block assembly 248. A pawl assembly 249 is further provided to alternatively engage the lower cam assembly. A pin drive rear link 250 is also provided and which is pivotably attached to the lower cam assembly 244. For ease of understanding of the relative positioning of the various components, the mounting block assembly 248 has been removed from the structure depicted in FIGS. 5B and 5C and the bell crank assembly 246 has been removed from FIG. 5C.

The trigger rack assembly 240 includes a mechanical rack 252 extending from a trigger 254 sized and shaped to receive a portion of an operator's hand. Also extending from the trigger 254 is a phasing dowel 256 which is configured to limit the depression of the trigger 254. The trigger rack assembly 240 further includes a spring 258 for biasing the assembly away from the mounting block assembly 248.

The rack 252 of the trigger rack assembly 240 engages the trigger cam assembly 242. The trigger cam assembly 242 further includes a trigger pinion 259 (See FIG. 5D) with teeth which mate with the teeth of the rack 252. The trigger pinion 259 is placed adjacent to a cam subassembly 260, each of which are positioned on a central trigger shaft 262.

Figure 6A:
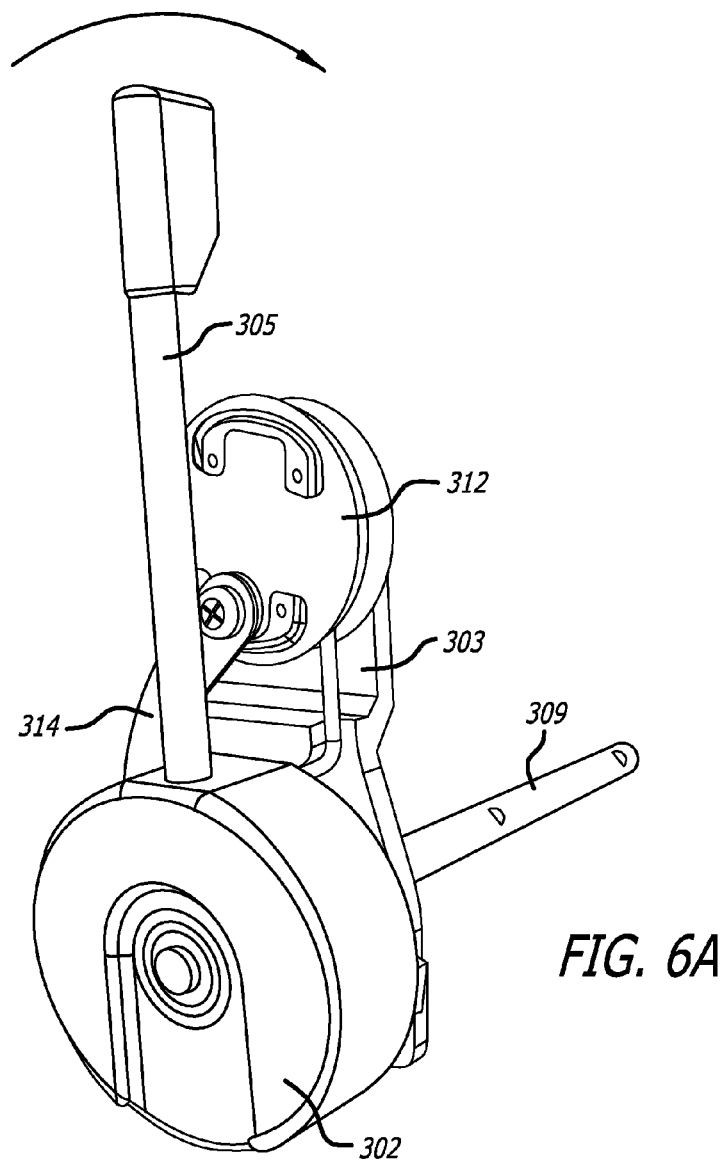
FIG. 6A is an enlarged perspective view, depicting a reset assembly of the multi-actuating trigger anchor delivery system of FIG. 1C.
Figure 6B:
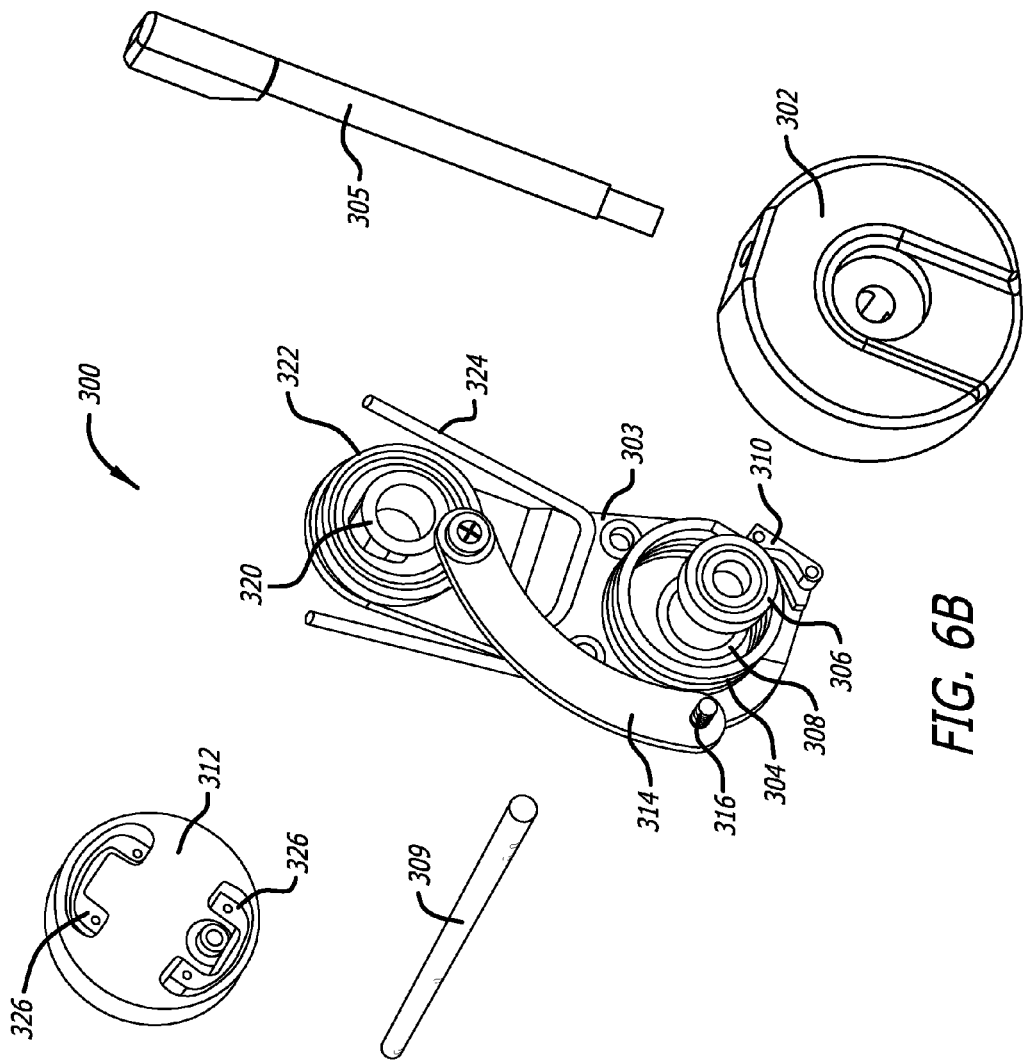
FIG. 6B is a perspective view, depicting the assembly of FIG. 6A with a reset knob and reset one way wheel removed.

The lower cam assembly 244 includes a link 264, one end of which travels through an open V-shaped slot formed in the lower cam plate 266. Also formed in the lower cam plate 266 is a through hole 267 for receiving a shaft of a reset assembly (described below in connection with FIGS. 6A and 6B). The opposite end of the link 264 is configured to slide within a slot 269 formed within the pin drive rear link 250. A top end 268 of the pin drive rear link 250 is operatively associated with structure for advancing components of the anchor assembly through the core assembly 120.

Figure 5A:
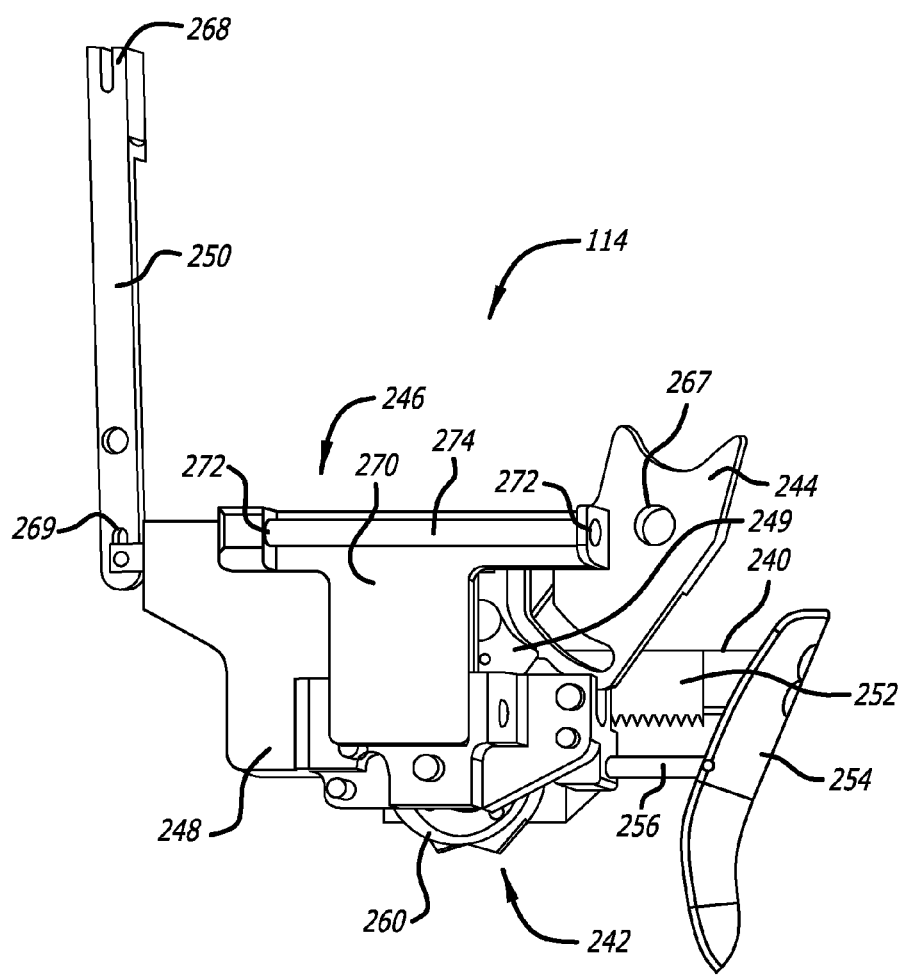
FIG. 5A is an enlarged elevation view, depicting a trigger assembly of the multi-actuating trigger anchor delivery system of FIG. 1B.
Figure 5B:
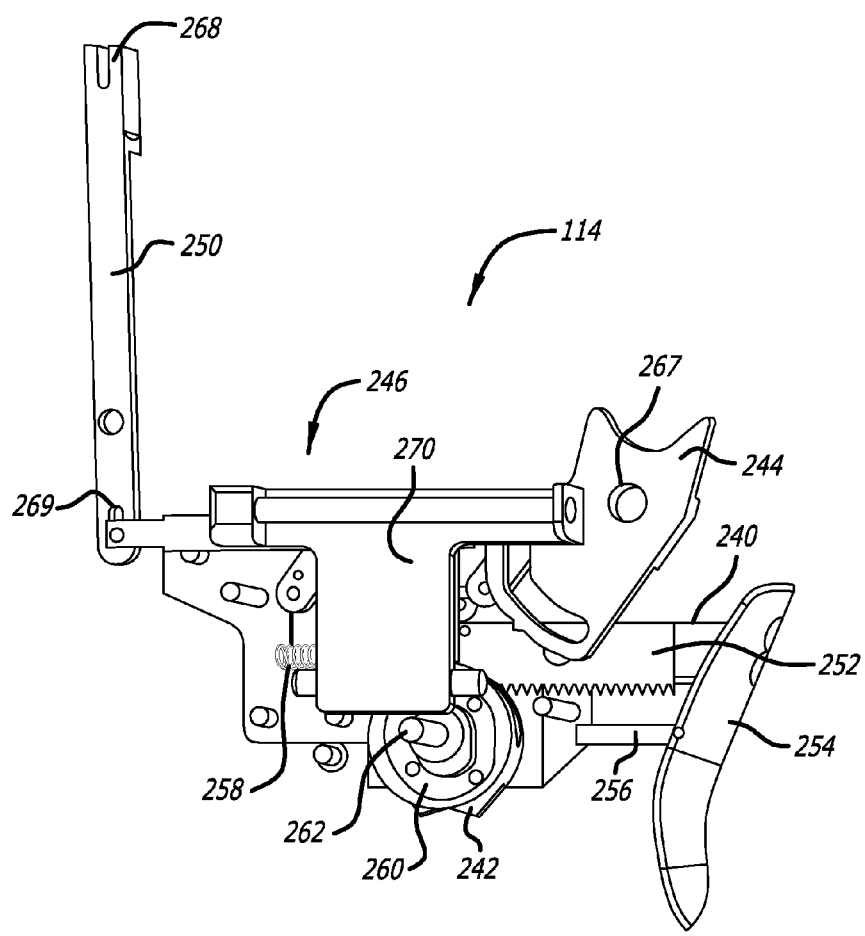
FIG. 5B is an elevation view, depicting the trigger assembly of FIG. 5A with a mounting block removed.
Figure 5C:
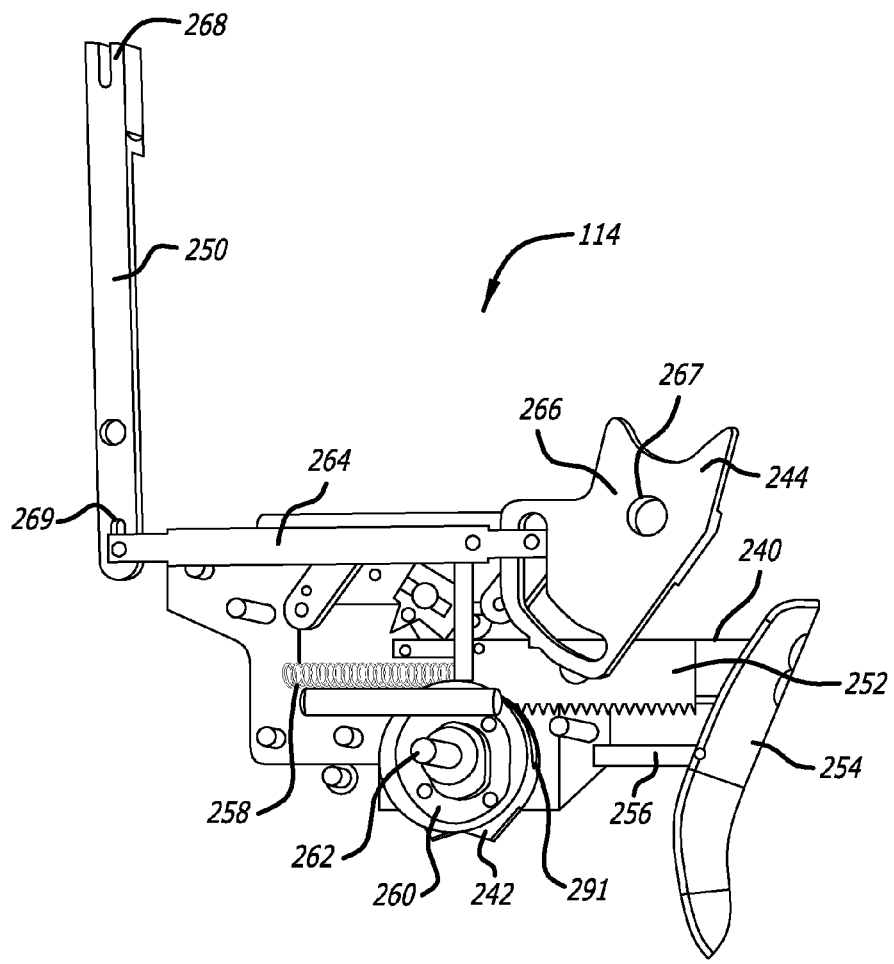
FIG. 5C is an elevation view, depicting the trigger assembly of FIG. 5B with a bell crank assembly removed.

The bell crank assembly 246 includes a T-shaped frame 270 at the top of which are a pair of spaced arms 272 (FIG. 5A). Configured between the arms is a bell crank rail 274. On a back side of the structure is configured a bell crank follower 275 (See FIG. 5G).

Figure 5D:
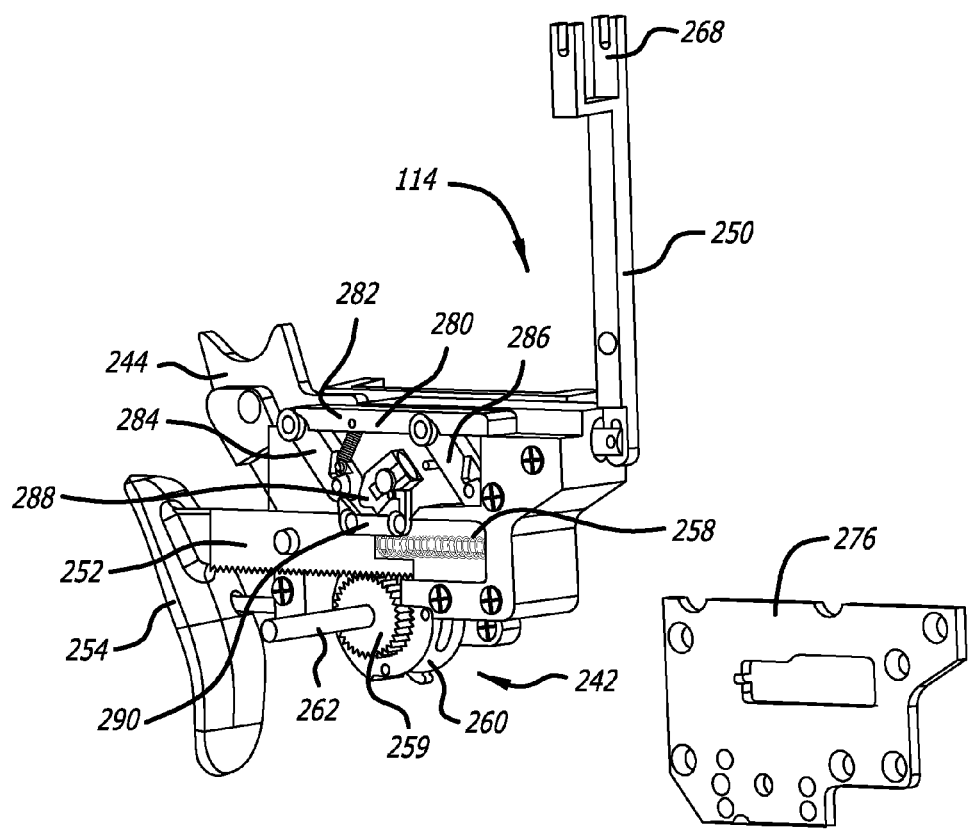
FIG. 5D is a rotated perspective view, depicting the trigger assembly of FIG. 5C with a mounting block cap removed.

As best seen in FIG. 5D where the mounting block cover 276 is removed, the trigger assembly 114 further includes a deploy plate assembly 280. This assembly includes a deployment plate 282 to which are pivotably attached a first link 284 and a second link 286. A double pawl assembly 288 is further provided, the operation of which is controlled by a sprag actuator 290 which is mounted to the trigger rack 242.

The double pawl assembly 288 is configured to act as a trigger control mechanism. In a first default position, the double pawl assembly 288 engages the rack assembly 240 in a manner which permits the trigger 254 to be depressed while allowing for and holding partial depression and preventing incomplete depression (See FIG. 5E). Once the trigger 254 is completely depressed, the sprag actuator 290 engages the double pawl assembly causing it to rotate such that the default engagement between the rack assembly 240 and the double pawl assembly 288 is eliminated (See FIG. 5F). Thereafter, the rack assembly 240 can return via the bias spring 258 to its original position (See FIG. 5D). As the default engagement of the rack assembly 240 and double pawl assembly 288 is eliminated, a second alternative engagement is created. In the second engagement, the double pawl assembly permits the trigger 254 and rack assembly 240 to return to the original position and prevents an incomplete return to the original position. That is, the double pawl assembly controls the trigger stroke bi-directionally. Thus, the engagement between the double pawl assembly 288 and the sprag actuator 290 then limits the degree to which the trigger can be depressed as well as facilitates the return of the trigger 254 to its default or un-depressed position.

Accordingly, the single trigger 254 actuates all steps of deployment through operative association with the rocker pawl assembly 163 and the throwout arm assembly 232. That is, activation of the trigger 254 causes the bell crank assembly 270 to pivot laterally taking with it the throwout arm assembly 232. By way of its connection to the central shaft 230, the throwout arm accomplishes the shuttling of the shaft 230 between functions performed by the spool assembly 190. Moreover, actuation of the trigger 254 further accomplishes the alternative engagement and disengagement between the rocker pawl 163 and the crank arbor 170. This engagement and disengagement permits the longitudinal movement of the spool assembly 190 between rear and forward positions. As a needle assembly and pusher assemblies are operatively linked to this mount, this longitudinal movement is likewise controlled by the trigger 254 actuation.

Further trigger control is provided by the interaction between the phasing dowel 256 and the trigger cam subassembly 260. That is, the trigger cam 260 includes a plurality of slots 291 formed in a periphery thereof. These slots 291 receive a terminal end of the phasing dowel 256 so that continued rotation of the trigger cam 260 in response to trigger depression is inhibited by the engagement between these parts. A roller clutch (not shown) configured within the trigger cam 260 provides yet further control by inhibiting the cam 260 from moving except during an inward trigger stroke.

The window 107 in the handle case 106 (FIG. 1A) can further be configured to provide access to components of the trigger assembly 114. That is, the double pawl assembly 388 can be manually engaged, for example, to thereby override a jam. Likewise, other components of the assembly 114 can be so engaged to facilitate proper function.

The handle assembly 102 further includes a reset assembly 300 (See FIGS. 1C and 6A-B) for resetting the delivery system after deploying and implanting an anchor assembly to be ready to deploy another anchor assembly. The reset assembly 300 includes a reset knob 302 rotatably mounted to a reset plate 303 and having an interior configured to receive an engagement spring 304. A lever 305 is further provided for easy manipulation of the assembly. Also, a pair of bearings 306, 308 are provided to mate with the reset knob 302 and to provide a surface for engaging a shaft 309 extending laterally through hole 267 of the trigger assembly 114. A knob latch 310 is configured to releasably engage the knob 302.

The reset assembly 300 also includes a one way reset wheel assembly 312 mounted to the reset plate 303 to which a reset link 314 is rotatably connected. The reset wheel assembly 312 prevents backwards motion of the shaft until the reset action is complete. The reset action recharges the spring 304 which powers the urethral cam 244 (FIG. 5D). Near an opposite terminal end of the reset link 314 is a threaded projector 316 adapted to engage complementary structure of the knob 302 (See FIG. 6B). The reset assembly 300 also includes a one way reset clutch 320 configured concentrically within a reset bearing 322. Also contained within the reset assembly is a U-shaped reset wire form 324. Bumpers 326 are provided to deflect the U-shaped wire form 324 which acts on the bumpers 326 to push the one way reset wheel 312 out of the top dead center and bottom dead center positions where the link 314 cannot rotate the wheel 312.

In the above description springs have been described as the mechanism for actuating the various assemblies when the trigger is pulled, however, it is also within the scope of the invention to use other mechanisms such as motor, compressed gas, elastomers and the like.

One preferred embodiment of an anchor assembly of the present invention is depicted in FIGS. 7A-D. In its unconstrained configuration, the first or distal anchor component 370 includes a first tubular portion 372 which is generally orthogonal to a second tail portion 374. It is to be noted, however, that while housed in a delivery assembly and prior to deployment at a target area, the first anchor component 370 is constrained to define a generally straight configuration, only subsequently assuming the unconstrained configuration upon deployment from the delivery device.

Figure 7A:
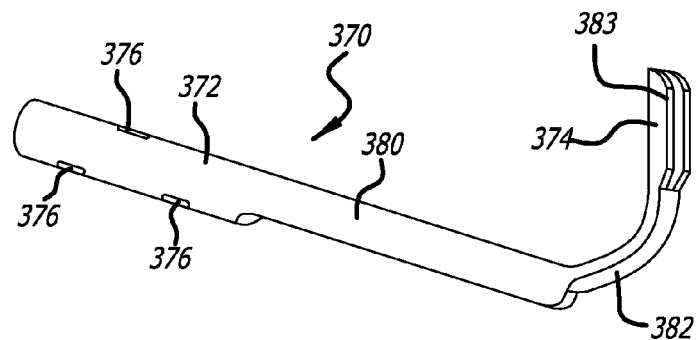
FIG. 7A is a perspective view, depicting one preferred embodiment of a first anchor member of an anchor assembly of the present matter.
Figure 7B:
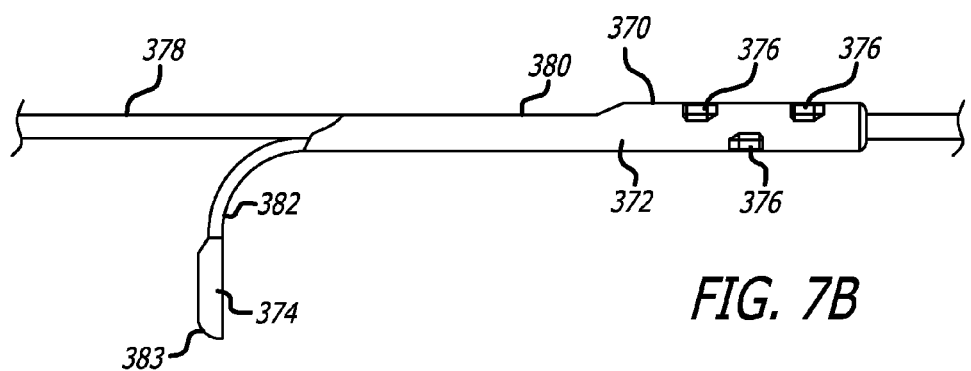
FIG. 7B is a side view, depicting the first anchor member of FIG. 7A attached to a connecting member.

The tubular portion 372 of the first anchor component 370 includes a plurality of tabs 376 which can be deformed or deflected to accomplish affixing the component 370 to a connector assembly 378 (See FIG. 7B). It has been found that three such tabs 376, two on one side of the tubular portion 372 and one on an opposite side provide a sufficient connecting force and a desired balance between the connector 378 and first anchor component 370 and to move the first anchor component 370 by applying a force either in the proximal or distal direction.

It is contemplated that the first anchor component 370 can be laser cut from a tube formed of nitinol or other appropriate material. A mid-section 380 of the component 370 provides a structural transition from the tubular portion 372 to the tail portion 374. As such, a portion of a side wall is removed in the mid-section area 380. A further portion of the side wall is removed to define a connecting section 382 of the tail 374 which extends from the mid-section 380. This connector section 382 acts as a spring to accomplish the relative unconstrained angle assumed between the tail 374 and tubular portion 372. A terminal end portion 383 of the tail 374 embodies structure having a surface area which is larger than that of the connector section 382 to thereby provide a substantial platform for engaging tissue at a target site.

Figure 7C:
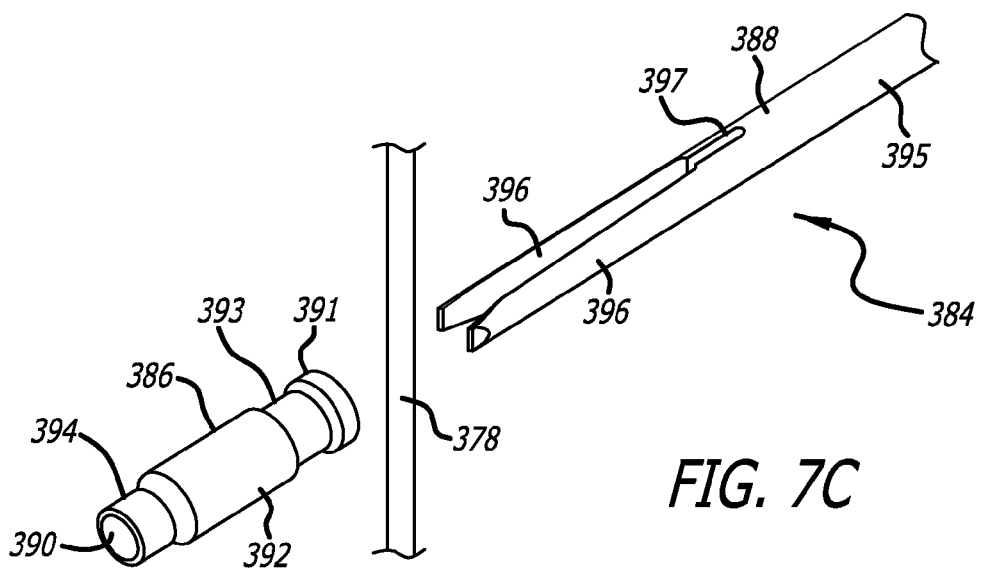
FIG. 7C is a perspective view, depicting components of one of the preferred embodiments of the second anchor member in a configuration prior to assembly.
Figure 7D:
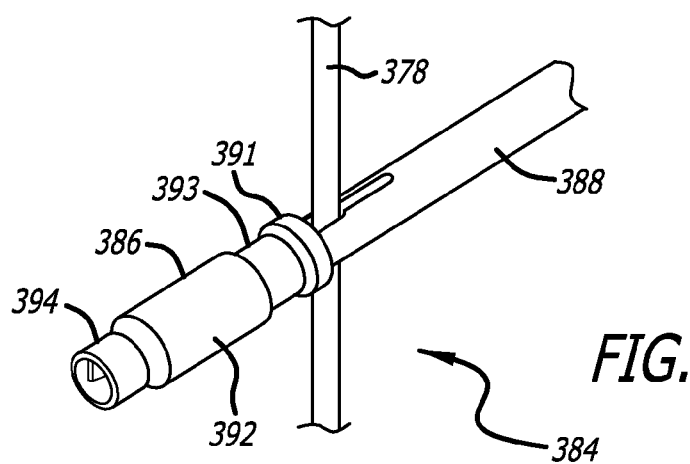
FIG. 7D is a perspective view, depicting an assembled second anchor member of the present invention attached to a connecting member.

As shown in FIGS. 7C and D, the second anchor component 384 includes a first part 386 and a second part 388. Once the first anchor component 370 is positioned at a target site by employing a delivery device such as that disclosed below (or previously), the second anchor component 384 is assembled in situ.

The first part 386 of the second anchor component 384 includes an internal bore 390 sized to receive a portion of the second part 388 of the second anchor component 384 in a locking engagement. An external surface of the first part 386 is sized and shaped to include a proximal collar 391 spaced from a mid-section 392, each of which have generally cylindrical profiles. A smaller diameter, outer cylindrical portion 393 is configured between the proximal collar 391 and mid-section 392 of the component and a distal cylindrical portion 394 having yet a smaller cylindrical profile defines a distal end thereof.

The second part 388 of the second anchor component 384 includes a solid generally cylindrical back end 395, extending from which are a pair of spaced prongs 396. Terminal ends of the prongs 396 can be tapered to both facilitate the insertion of the prongs 396 within the internal bore 390 of the first part 386 as well as to receive a section of the connector assembly 378. Notably, the prong structure commences at a narrowed slot 397 which steps outwardly to a wider dimension to thereby define the space between the prongs 396. This narrow slot 397 provides the second part 388 with desired structural rigidity to receive the connector assembly 378 and to facilitate lockingly engaging the connection between the first 386 and second 388 parts. The space between the prongs 396, in one embodiment can be dimensional relative to the diameter of the connector 378 such that is has sufficient clamping force such that the first part 386 is not needed and therefore is optional for providing additional security.

Thus, in its pre-implanted form, the anchor assembly can include one anchor member (e.g., first anchor) whose initial engagement with a connector is generally coaxial and another anchor member (e.g., second anchor) with an initial engagement being generally perpendicular with the connector.

These assemblies can further be employed to deliver therapeutic or diagnostic substances to the interventional site. For example, in a procedure to treat a prostate gland, substances that cause the prostate to decrease in size such as 5-alpha-reductase inhibitors can be introduced at the treatment site. A particular advantageous procedure is to use the needle of the anchor delivery device to inject 100 to 200 units of botulinum toxin (such as available from Allergan, Inc.) dissolved in 4 mL of saline either before, during or after deploying the anchor assembly. Preferably, 2 mL are injected in each lobe of the prostate. Another advantageous procedure is to use the needle of the anchor delivery device to inject 100 to 300 units of botulinum toxin dissolved in 10 to 30 mL of saline into the base of the bladder, bladder lateral walls and/or trigone. Preferably, 0.5 to 1.0 mL are injected into about 20 to 30 sites in the bladder for treating over-active bladder. Other substances but not limited thereto, which may be introduced at the site include various scarring agents, rapamycin and its analogues and derivatives, paclitaxel and its analogues and derivatives, phytochemicals, alpha-1a-adrenergic receptor blocking agents, smooth muscle relaxants and other agents that inhibit the conversion of testosterone to dihydrotestosterone.

Figure 8:
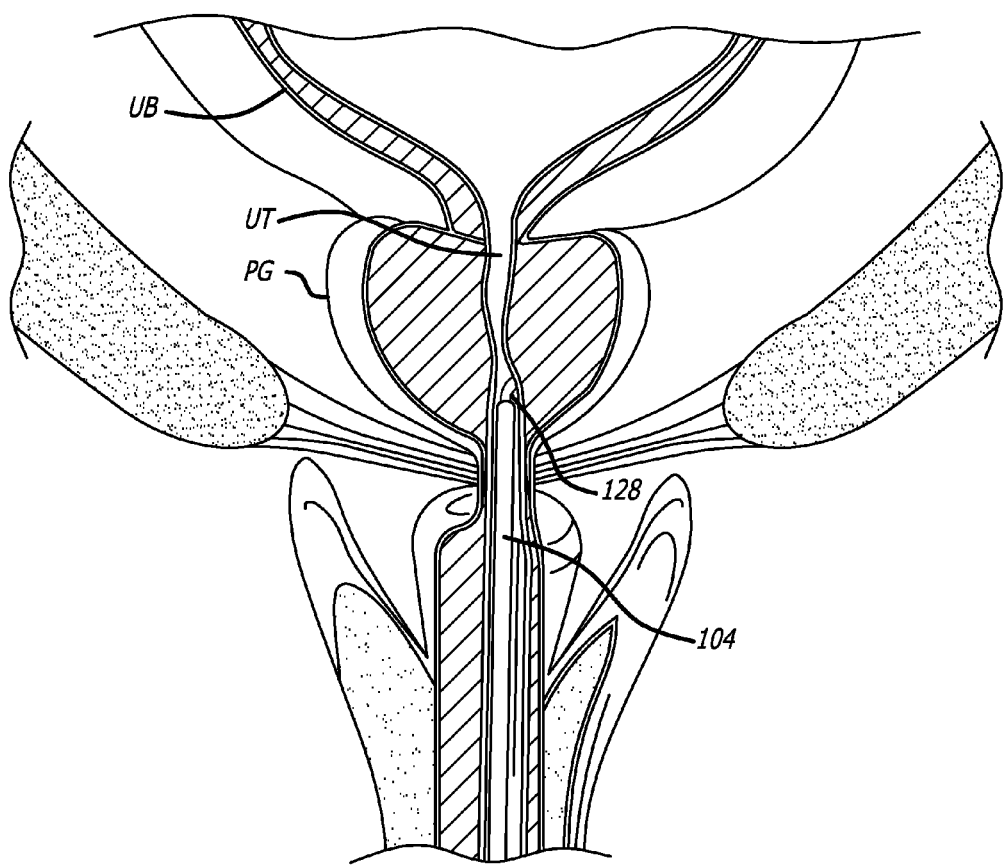
FIG. 8 is a cross-sectional view, depicting a first step of treating a prostate gland using the present invention.

In a first step to deliver and deploy an anchor assembly for the purpose of manipulating tissue or other anatomical structures, the endoscope device is employed to view the positioning of a multi-actuating trigger anchor delivery device 100 at the interventional site, for example, the elongate tissue access assembly 104 of the device is inserted into the penis of a patient and advanced until the distal end 128 is adjacent an interventional site in the urethra (UT) adjacent the bladder (UB; See FIG. 8). It has been found that a mechanical solution to the treatment of BPH such as that of the present invention, can be more compatible with patients recovering from prostate cancer compared to energy-based solutions. Furthermore, the present invention also contemplates steps for sizing the anatomy. As it relates to BPH treatment, the present invention also involves the placement of an ultrasonic or other device in the patient's body, such as in the rectum, to measure the necessary depth of insertion of the distal end of the needle assembly within the patient's body. This information can be used to set or create a depth stop for the needle assembly by the operator using a knob (not shown) on the outside of the handle connected to the stop assembly 126 so that during deployment the distal end of the needle assembly extends all the way through the prostate from inside the urethra to outside of the prostate capsule.

Figure 9A:
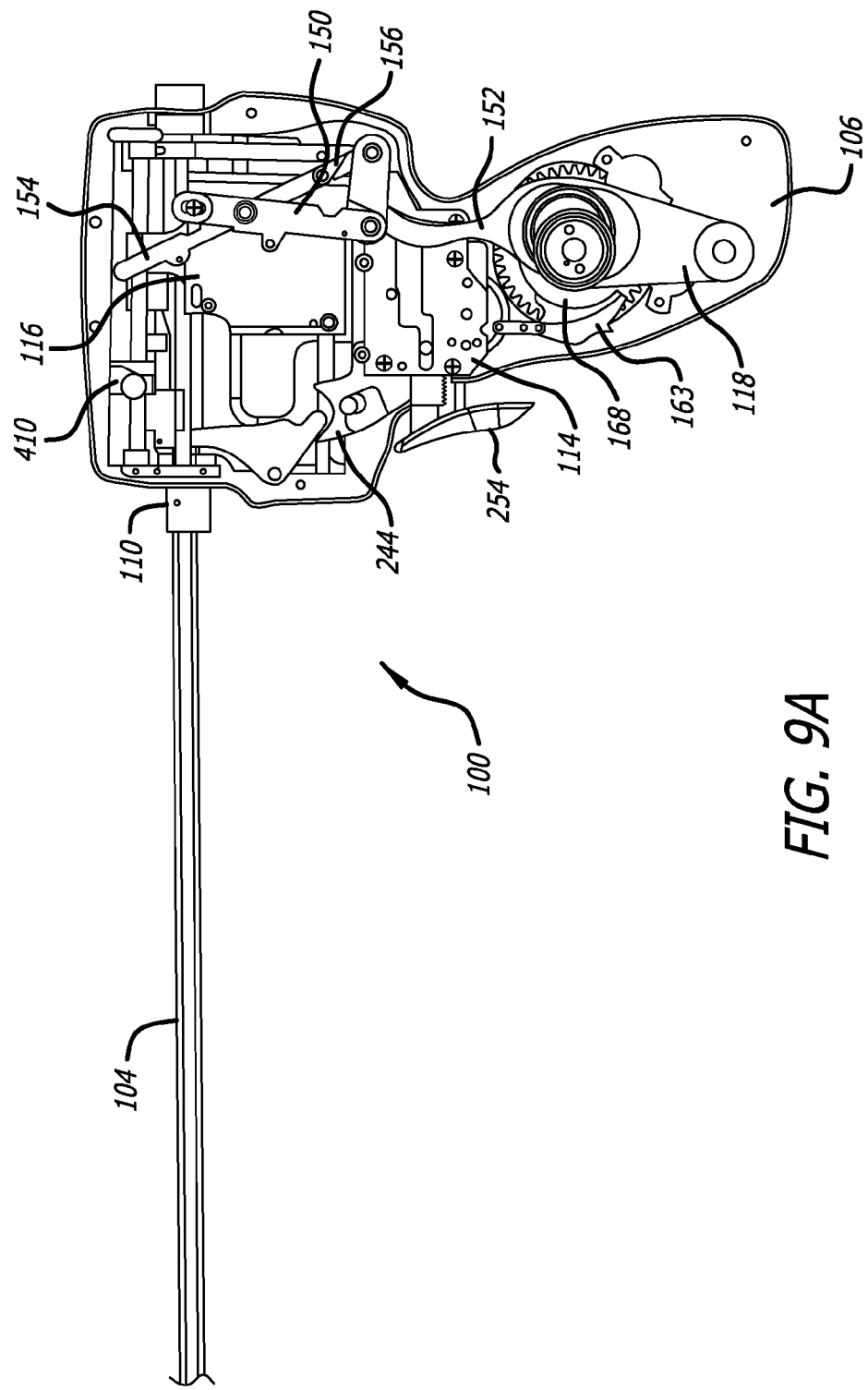
FIG. 9A is a left side view, depicting the multi-actuating trigger anchor delivery system of FIG. 1A with the left handle half and reset assembly removed.
Figure 9B:
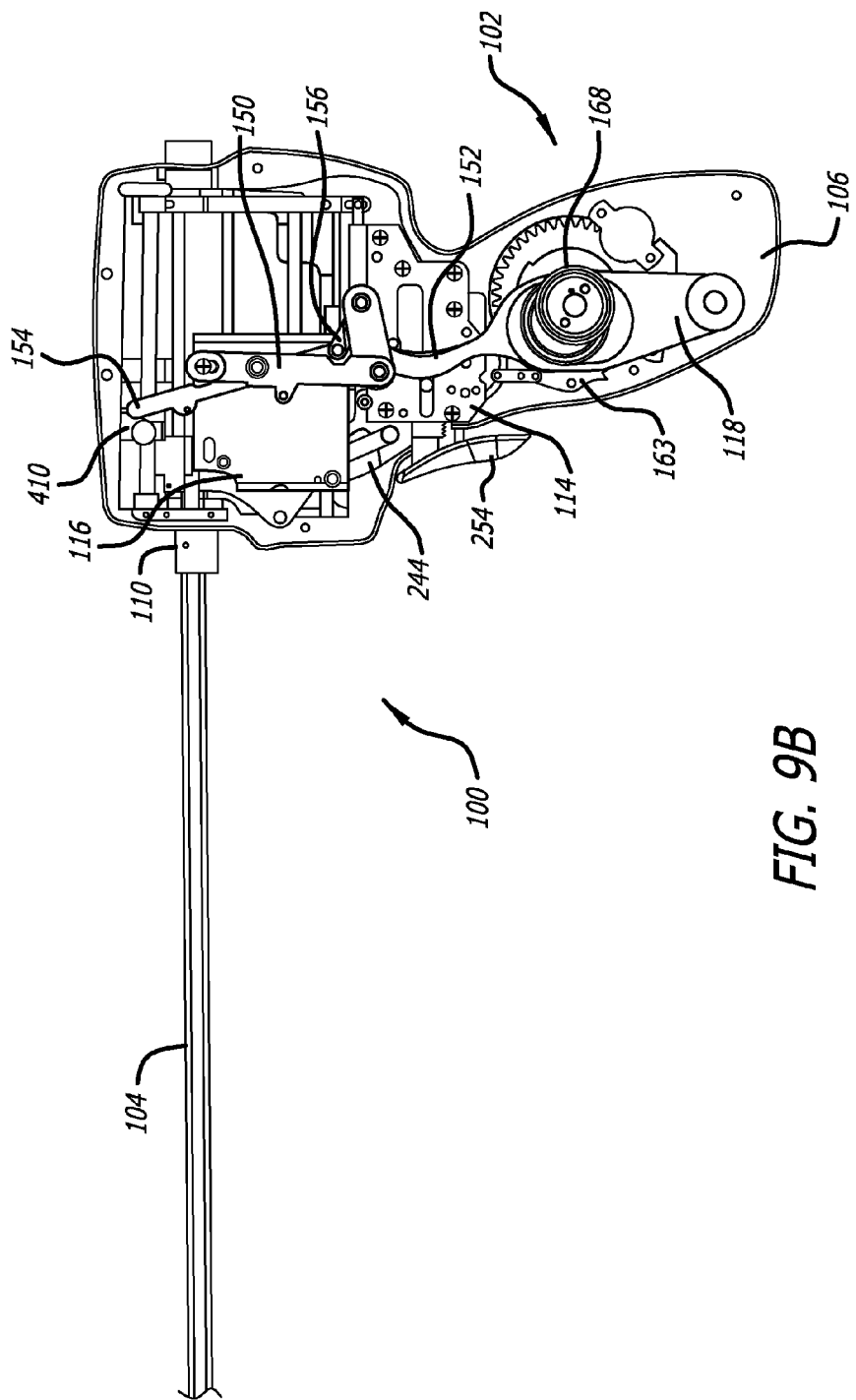
FIG. 9B is a left side view, depicting the assembly of FIG. 9A with the trigger depressed.

After so positioning the deployment device within the patient, the multi-actuating trigger anchor delivery device 100 is employed to assemble and implant an anchor assembly at an interventional site. In a first step, the trigger 254 of the trigger assembly 114 is depressed until through its interconnection with the rocker arm assembly 118 via the trigger cam subassembly 260, the rocker pawl follower 163 is released from a locking engagement with the rocker arm ratchet 168 (See FIG. 9A). Releasing the rocker arm ratchet 168 results in the unloading of the crank spring assembly 162 thereby causing rotation of the eccentric crank 176 and thereby the rocker arm assembly 118 and the forward translation of the upper portion of the rocker arm assembly 118 and the spool assembly 116 (See FIG. 9B). This is permitted through the interaction of the upper rocker arm assembly 150, the lower rocker arm assembly 152, and upper 154 and lower 156 break away links and a depth stop assembly 410 (See also FIGS. 2A and 3A). That is, the depth stop assembly 410 engages the upper break away link 154 so that it breaks (or rotates) with respect to the lower link 156 to limit the forward motion of the spool assembly. Such action accomplishes the advancement of a needle assembly 400 within the elongate tubular housing 140 via its connection with the spool assembly 116 (See FIG. 9D). Moreover, the depth stop assembly 410 can be positioned as desired to control the depth to which the needle assembly 400 is projected. The selected position may be based on anatomical measurements made by various imaging techniques such as ultrasound.

Figure 9C:
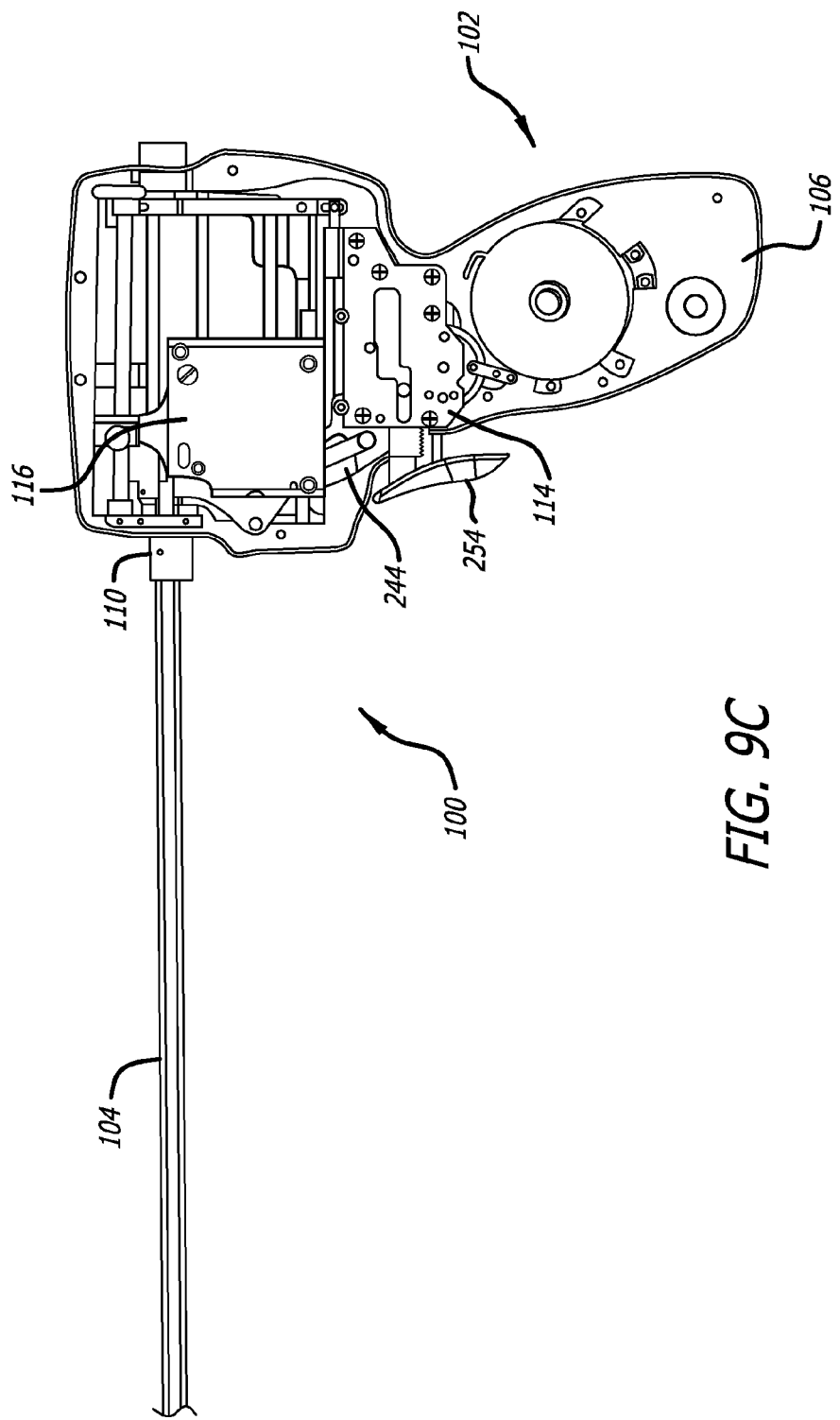
FIG. 9C is a left side view, depicting the assembly of FIG. 9A with the trigger partially returned and the rocker arm assembly removed.
Figure 9D:
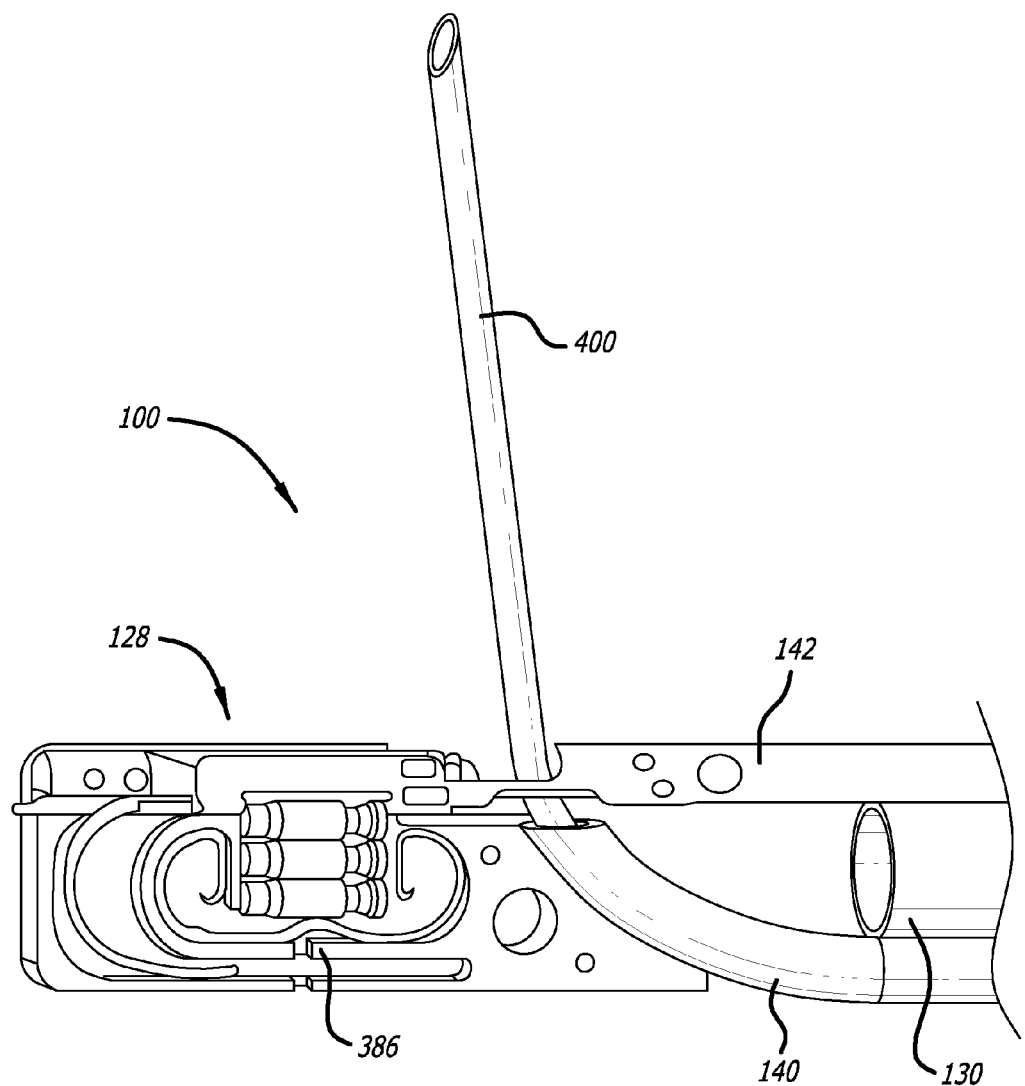
FIG. 9D is a partial cross-sectional view, depicting the distal end portion of the anchor deployment device and the lateral advancement of a needle assembly.
Figure 9E:
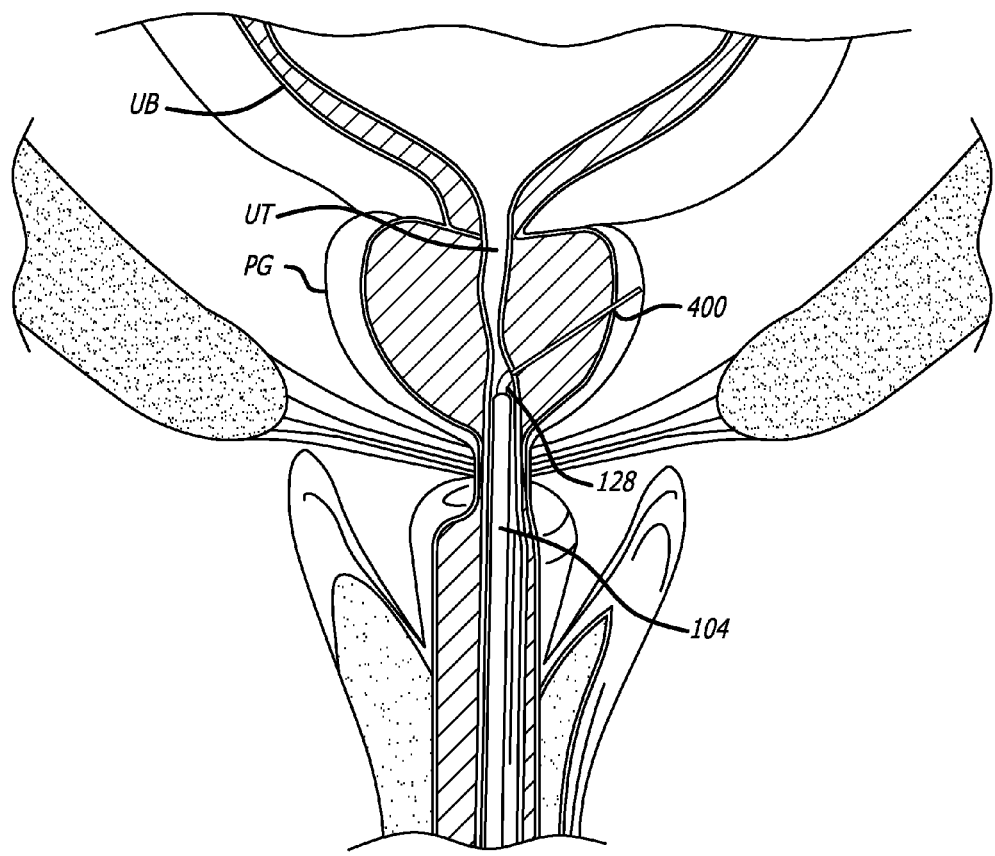
FIG. 9E is a cross-sectional view, depicting a second step of treating a prostate gland using the present invention.

Release of the trigger 254 permits the trigger 114 to return to a ready position, leaving the spool assembly 116 in its forward position (See FIG. 9C). The articulation of the double pawl assembly 288 from its default position (See also FIG. 5D) facilitates this return of the trigger assembly 114 to the ready position. Within the patient's anatomy, the advancement of the needle assembly 400 consequently results in the needle passing through the prostate gland (PG) (See FIG. 9E). In one contemplated approach, a terminal end of the needle 400 is positioned to extend beyond the prostate gland (PG) but it is to be recognized that the degree of needle insertion can be modified for a particular purpose.

Figure 10A:
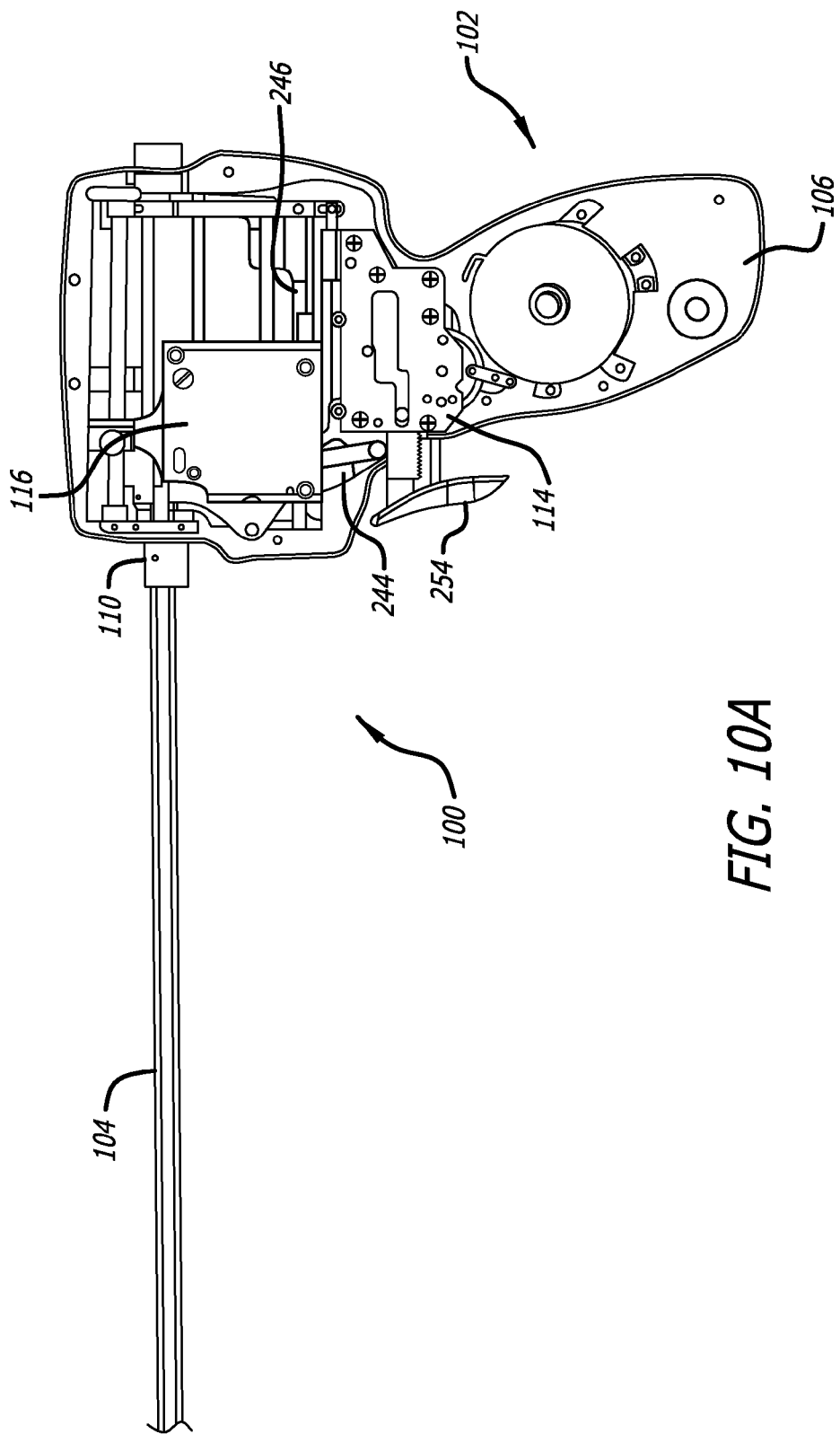
FIG. 10A is a left side view, depicting the assembly of FIG. 9C with the trigger being activated for a second time.
Figure 10B:
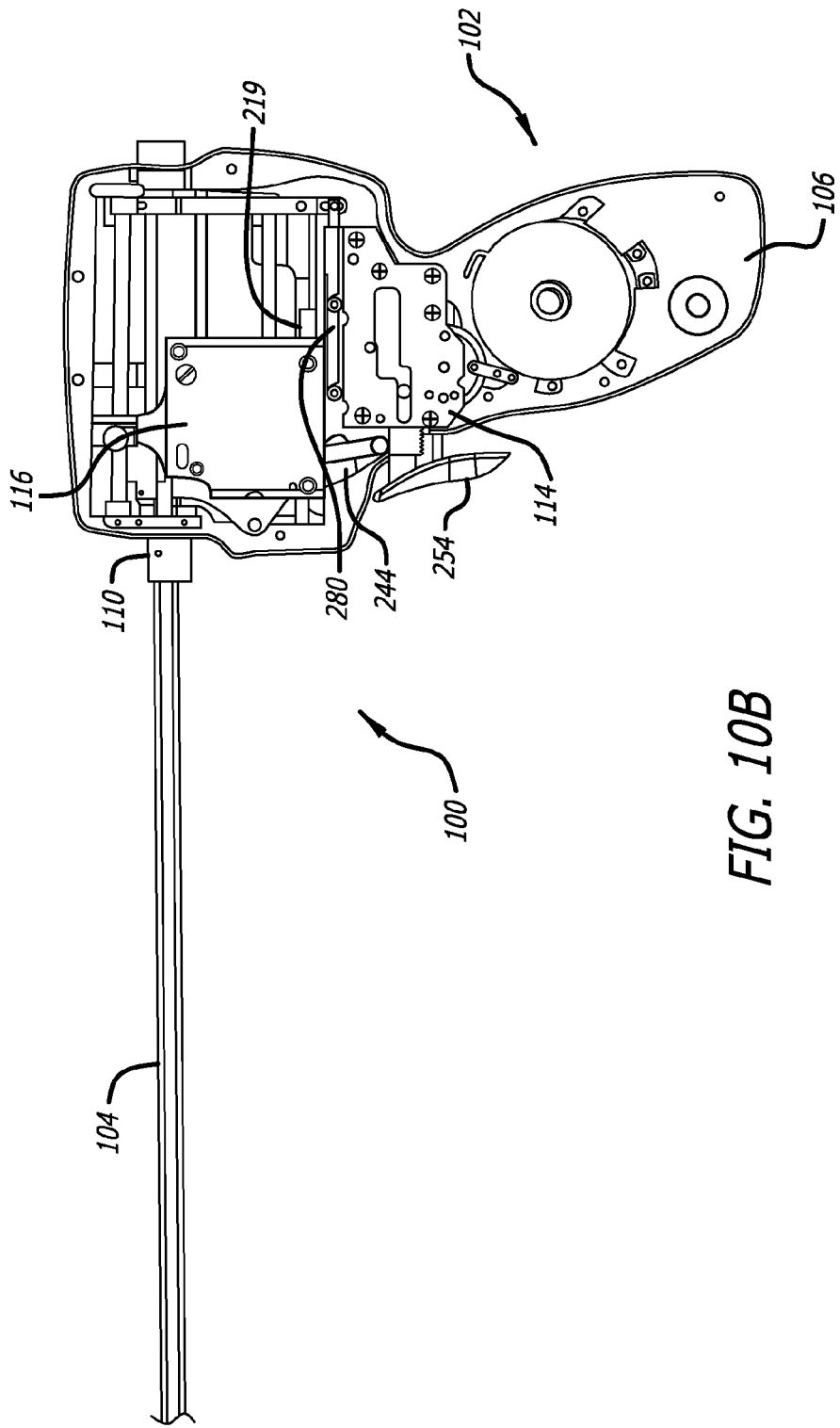
FIG. 10B is a left side view, depicting the assembly of FIG. 10A with the trigger further depressed.

Next, the trigger assembly 114 is employed again to effect the deployment of the distal anchor component 370 (See FIGS. 10A-F). With the spool assembly housing 116 in a forward position, a first half of a trigger 254 pull (FIG. 10A) causes the spool shaft 230 to move to the deploy side 194 of the spool assembly 190 (FIGS. 10A and 4A-B). This is accomplished via cooperation with the bell crank assembly 246 (See also FIG. 5A) which drives the throw out arm assembly 232 (See also FIGS. 4A-B). More specifically, with the depression of the trigger 254, the trigger cam 260 rotates. The bell crank follower 275 (See FIG. 5G) connected to the bell crank frame 270 rides along a variable surface formed on a side of the rotating trigger cam 260, the variability of the surface causing the bell crank frame 270 to pivot away from the spool assembly housing 116 at a desired juncture. This causes the bell crank frame 270 to pivot the throw out arm assembly 232 which in turn advances the spool shaft 230 to the deploy side of the spool assembly 190.

Figure 10C:
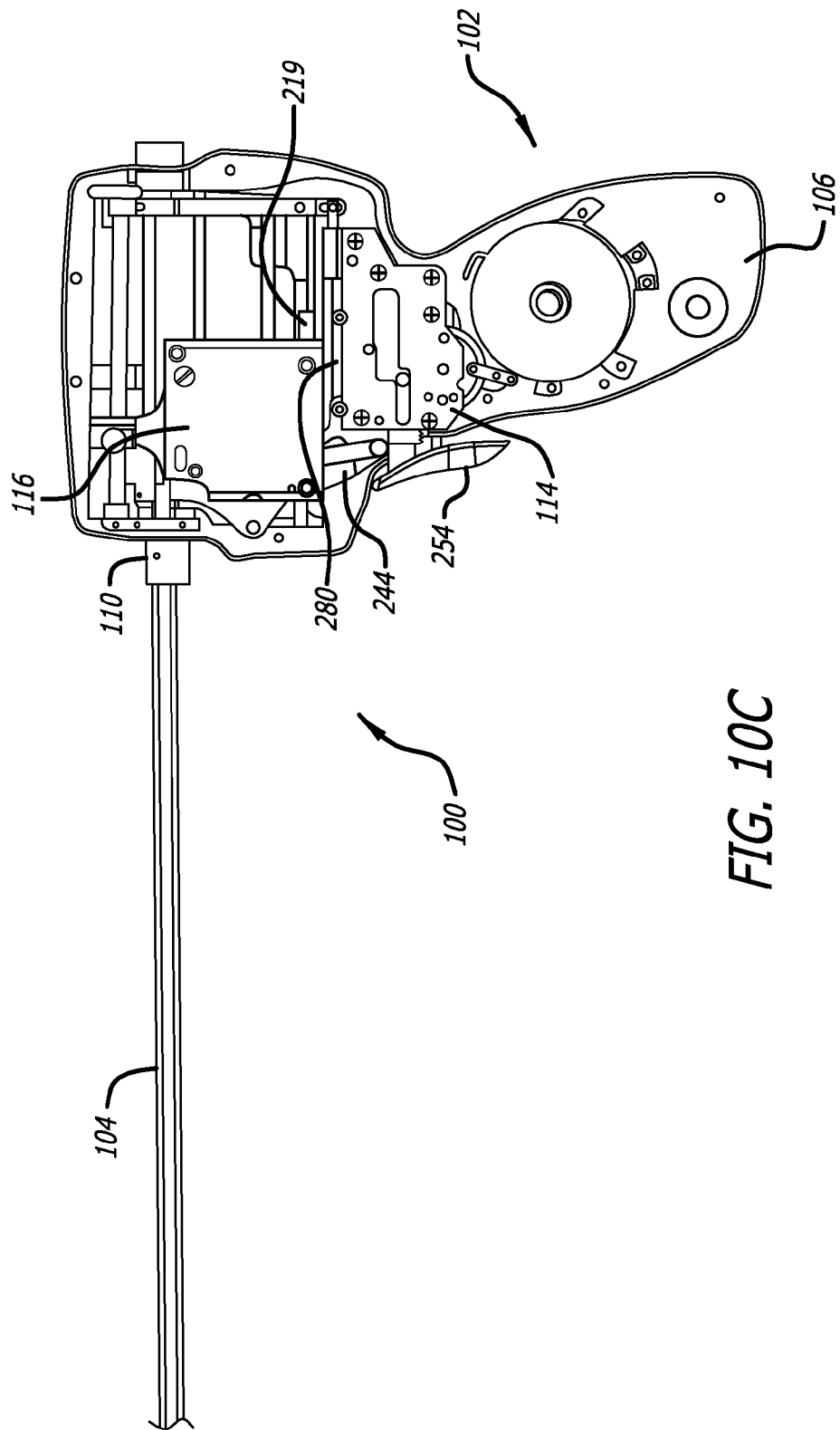
FIG. 10C is a left side view, depicting the assembly of FIG. 10B with the trigger completely depressed.

As the trigger 254 is continued to be depressed (FIG. 10B), the deploy plate 280 of the trigger assembly 114 (See also FIG. 5D) is positioned in a raised configuration. This raised position results from the vertical movement of a deploy plate push rod (not shown) which at one end rides along a periphery of the trigger cam 260 and at another end engages the deploy plate 280. As the push rod engages upon raised sections of the periphery of the trigger cam 260, the rod is translated vertically which causes the deploy plate 280 to rise. Being so positioned, the deploy plate assembly 280 actuates the suture deploy pawl assembly 219 (See also FIGS. 4A-B), which in turn, permits the release of the deploy spring 218 and coupled rotation, via the spool shaft 230, of the deploy spring 218 and the spool assembly 210 thereby advancing the suture from the delivery system 100. The two-toothed spool deploy ratchet 214 permits one half-turn of the spool assembly 210 before reengaging with the suture deploy pawl assembly 219 and arresting the suture advancement. At the finish of this second trigger 254 pull the deploy plate assembly 280 and the deploy pawl assembly 219 are back in their default positions (FIG. 10C).

Figure 10D:
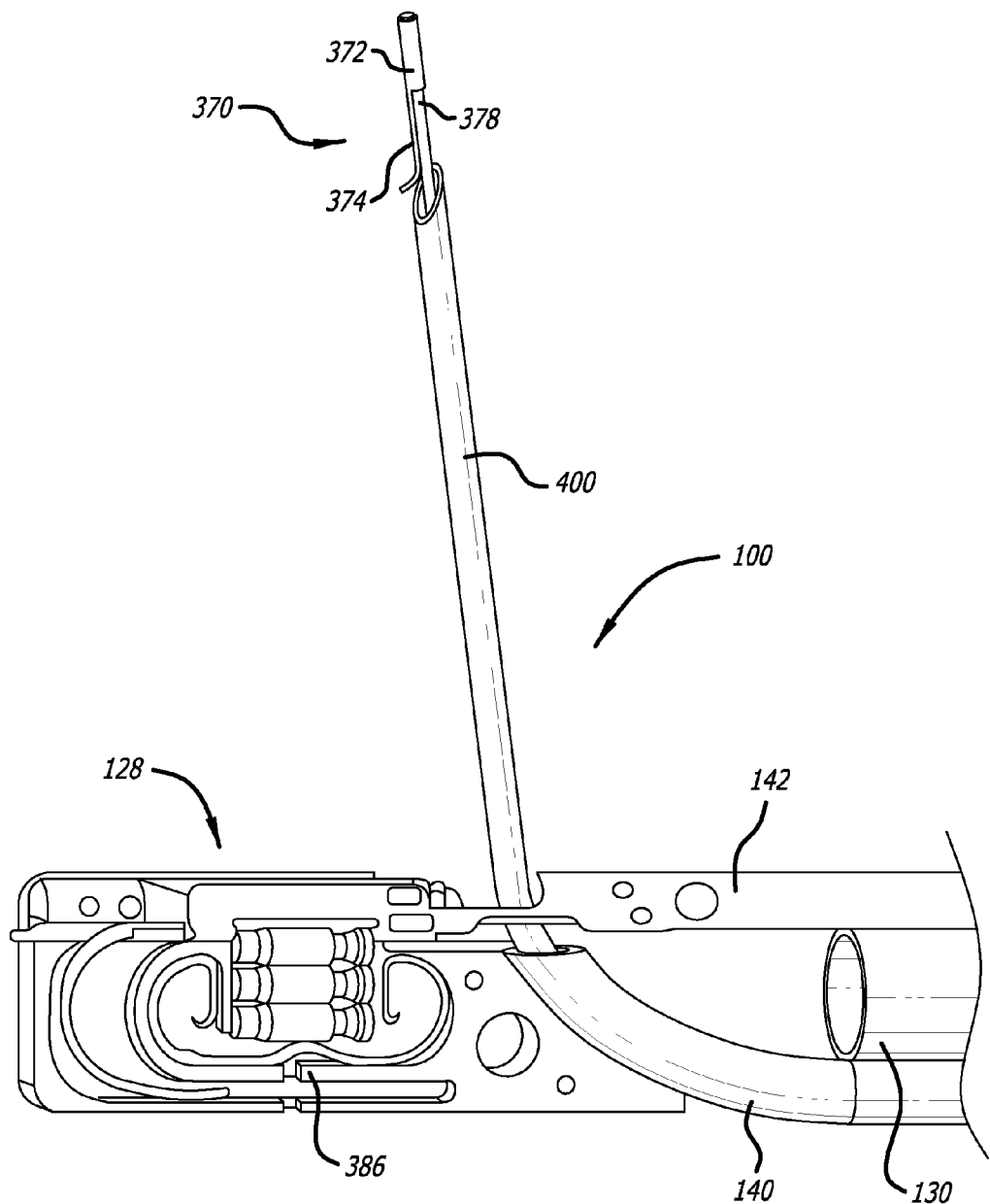
FIG. 10D is a perspective view, depicting a distal end portion of the anchor deployment device of FIG. 9D after deployment of the first anchor.
Figure 10E:
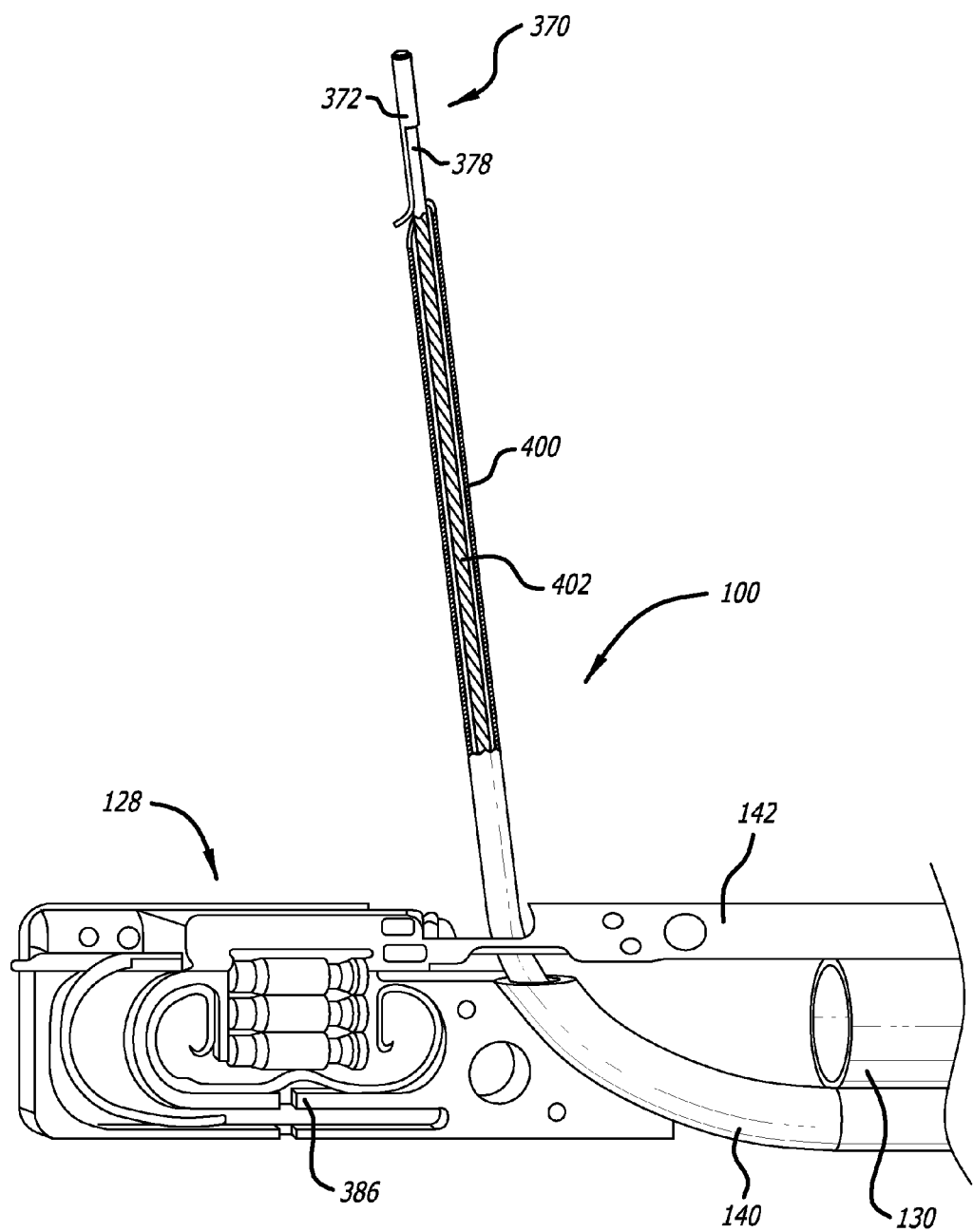
FIG. 10E is a cross-sectional view of the extendable tip, depicting the assembly of FIG. 10D.

At the distal end 128 of the multi-actuating trigger anchor delivery system 100, such action facilitates the advancement of the first or distal anchor component 370 attached to the connector 378 out of the needle assembly 400 (See FIG. 10D). As shown in FIG. 10E, a wire assembly 402 engages the connector 378 through a permanent connection such as a polyimide tube with adhesive. By way of its interconnection with the spool assembly 210 of the tension housing assembly 192 (See also FIGS. 4A-B), the desired length of the connector 378 is paid out. It is to be recognized that the wire assembly 402 has been shown in FIG. 10E for demonstrative purposes as its actual position may be further within the needle assembly 400 at this stage of device use. A connector diameter of approximately 40% of the inside diameter of the needle assembly 400 or greater is beneficial to pay out the connector 378 to prevent kinking of the connector material. The connector is preferably about 0.015 inch diameter PET monofilament. Moreover, at this stage no tension is supplied to the connector 378 and first anchor component 370 by the tension housing assembly 192.

Figure 10F:
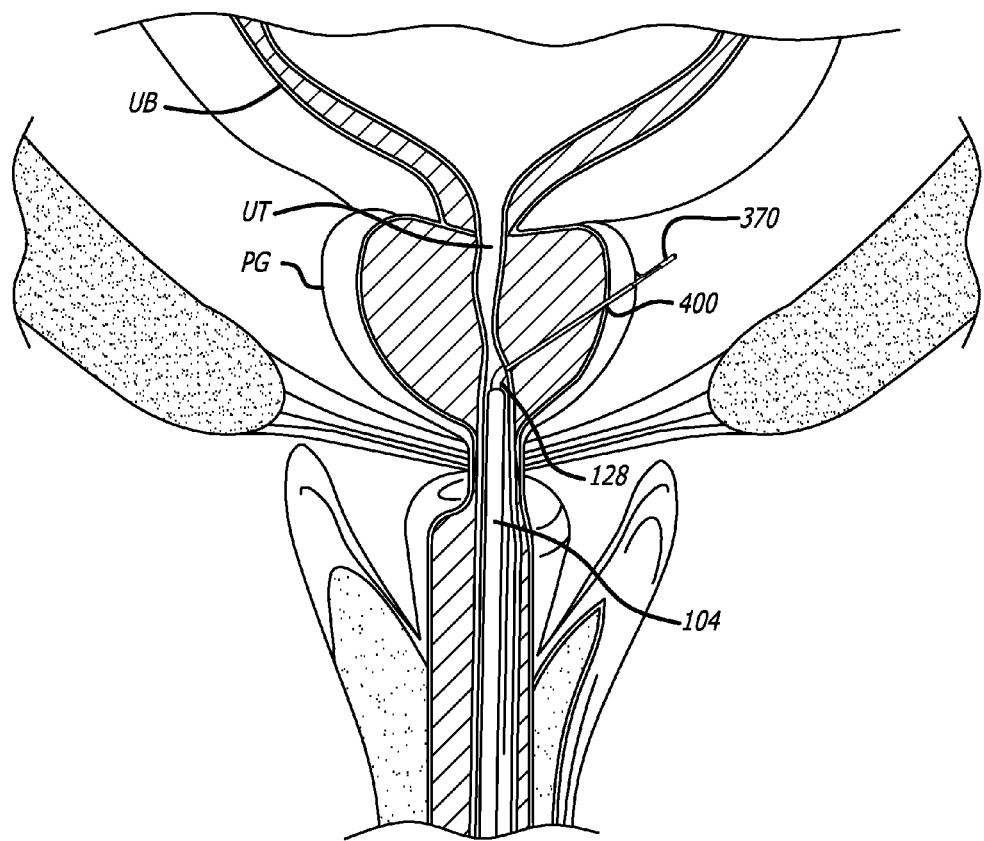
FIG. 10F is a cross-sectional view, depicting a further step of a method of treating a prostate gland using the present invention.

Accordingly, as shown in FIG. 10F, the first anchor component 370 is ejected from the needle housing beyond an outer surface of a prostate gland (PG). Of course, when desirable, the first anchor component 370 can surgically be placed within the prostate gland (PG) or in other procedures at any position within a patient.

Figure 11A:
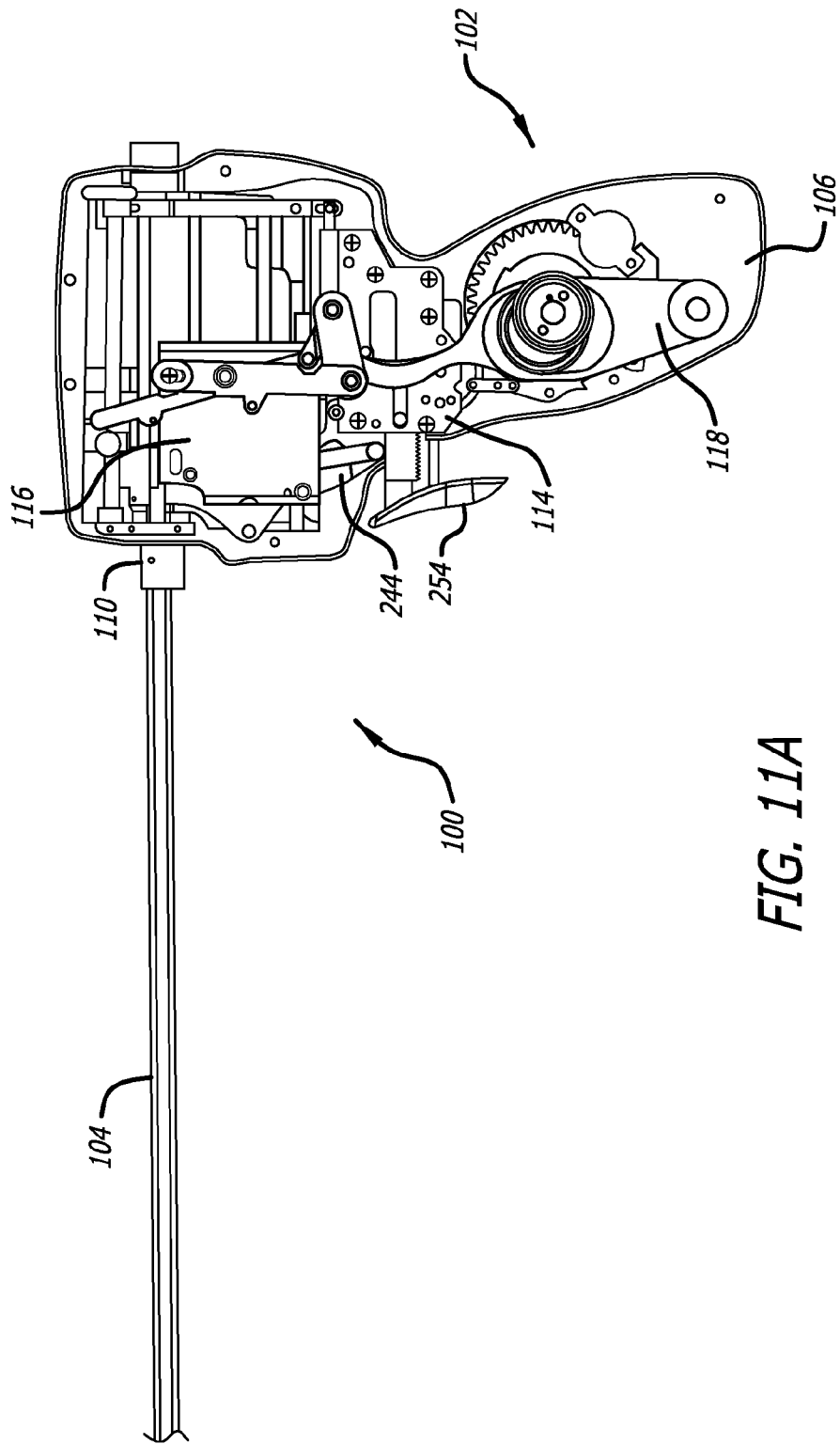
FIG. 11A is a left side view, depicting the assembly of FIG. 9A in a ready position for a third actuation.
Figure 11B:
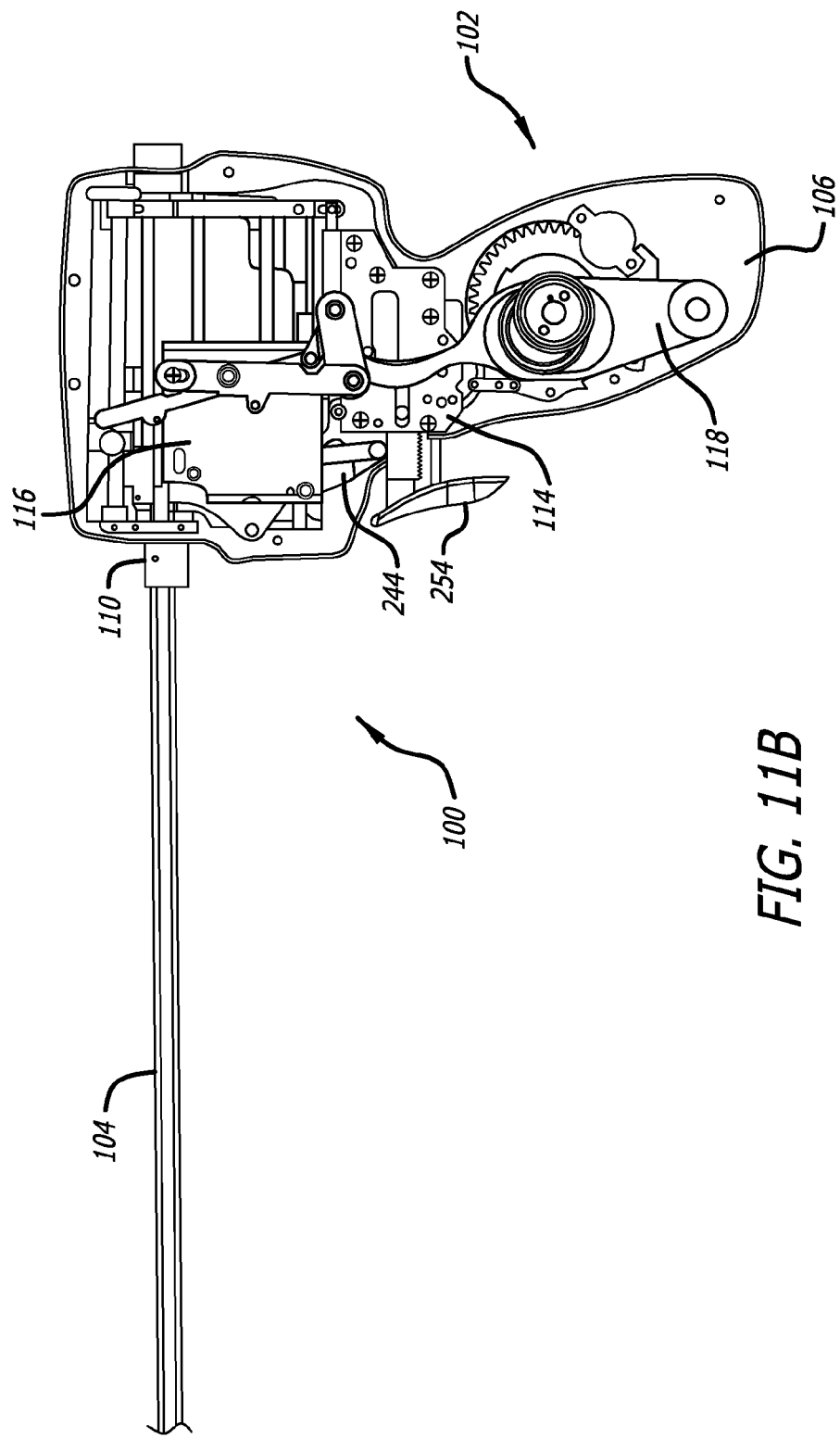
FIG. 11B is a left side view, depicting the assembly of FIG. 11A with the trigger partially depressed.
Figure 11C:
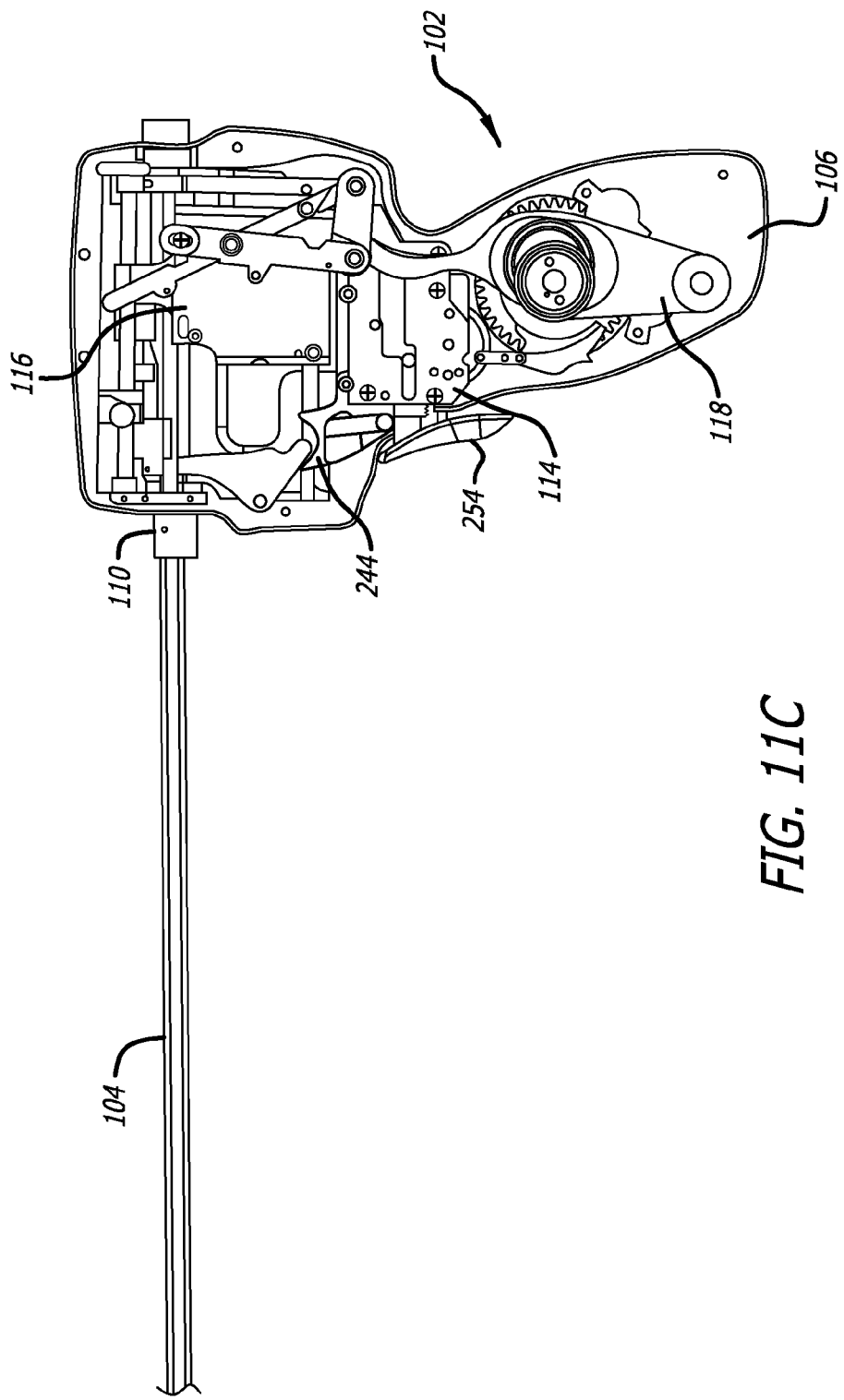
FIG. 11C is a left side view, depicting the assembly of FIG. 11B with the trigger completely depressed.
Figure 11D:
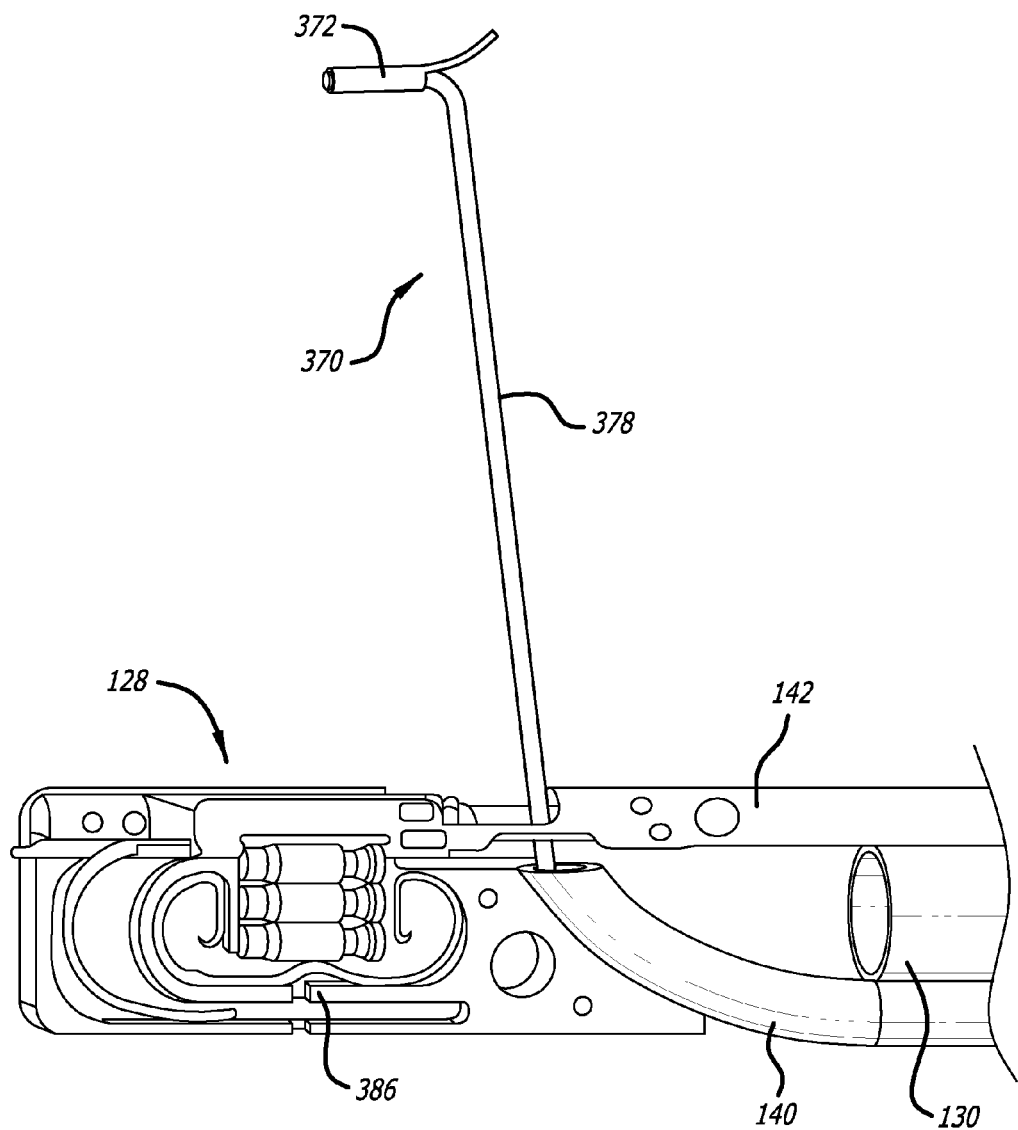
FIG. 11D is a perspective view, depicting the assembly of FIG. 9D after the complete retraction of the needle assembly.
Figure 11E:
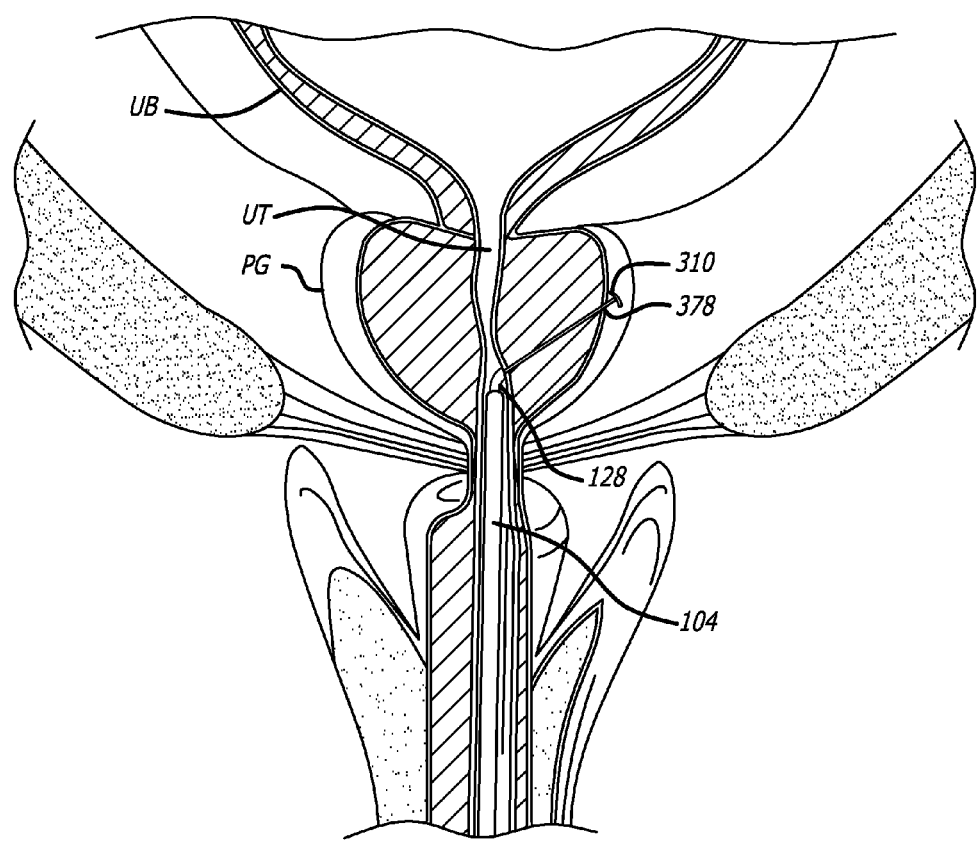
FIG. 11E is a cross-sectional view, depicting yet another step of a method of treating a prostate gland using the present invention.

Referring now to FIGS. 11A-E, the multi-actuating trigger anchor delivery system 100 is manipulated to withdraw the needle assembly 400 from the interventional site. As shown in FIG. 11A after the first anchor component is ejected from the needle assembly 400, the trigger 254 is again returned to a ready position. With the commencement of the third trigger 254 pull (FIG. 11B), the central shaft 230 is shuttled back to the tension side 192 of the spool assembly 116 (See also FIGS. 4A-B). Again, it is the cooperation of the bell crank assembly 246 and the throw out arm assembly 232 that facilitates the shuttling of the central shaft 230. Further depression of the trigger 254 results in the spool assembly 116 and rocker arm assembly 118 returning to a default position, again by lifting the rocker pawl 163 and releasing the crank spring assembly 162. Consequently, the needle assembly (not shown) which is attached to the spool assembly 116, is withdrawn completely within the needle tubular housing 140 (See FIG. 11D). Thus, the first anchor component 370 is left at the intervention site with the connector assembly 378 extending proximally within the elongate tissue access assembly 104 (FIG. 11E). During this juncture, a desired tension is placed upon the connector 378 and first anchor component 370 by tension housing assembly 192 of the spool assembly housing 116. Moreover, the tension assembly 192 permits additional suture to be paid out relative to the retracting spool assembly 116. It is this combination of suture pay-out and the function of the tension spring which facilitates the delivery of a custom-length, fixed-load implant.

Figure 12A:
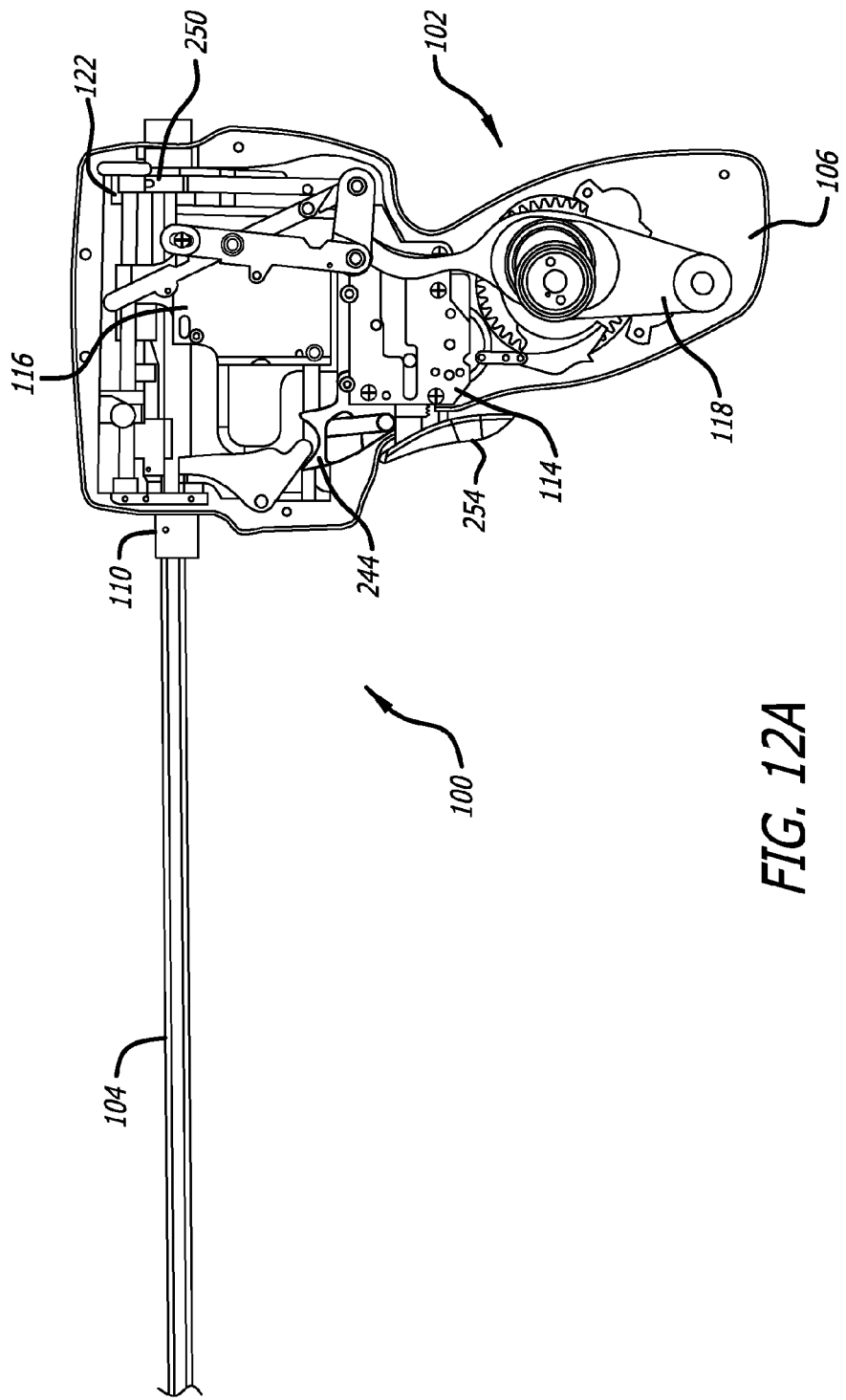
FIG. 12A is a left side view, depicting the assembly of FIG. 9A in a ready position for a fourth actuation.
Figure 12B:
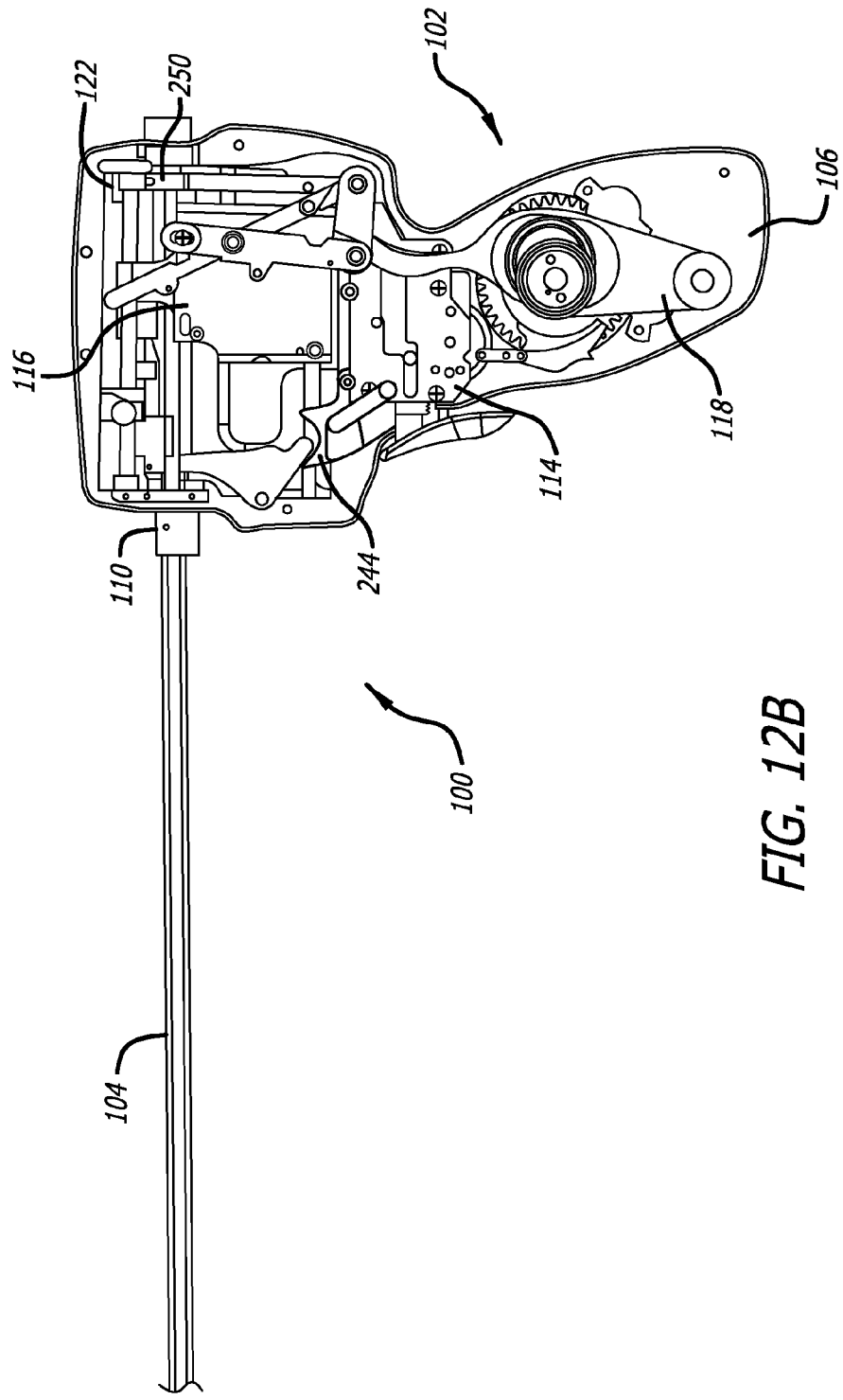
FIG. 12B is a left side view, depicting an intermediate stage of the depression of the trigger of the assembly of FIG. 12A.
Figure 12C:
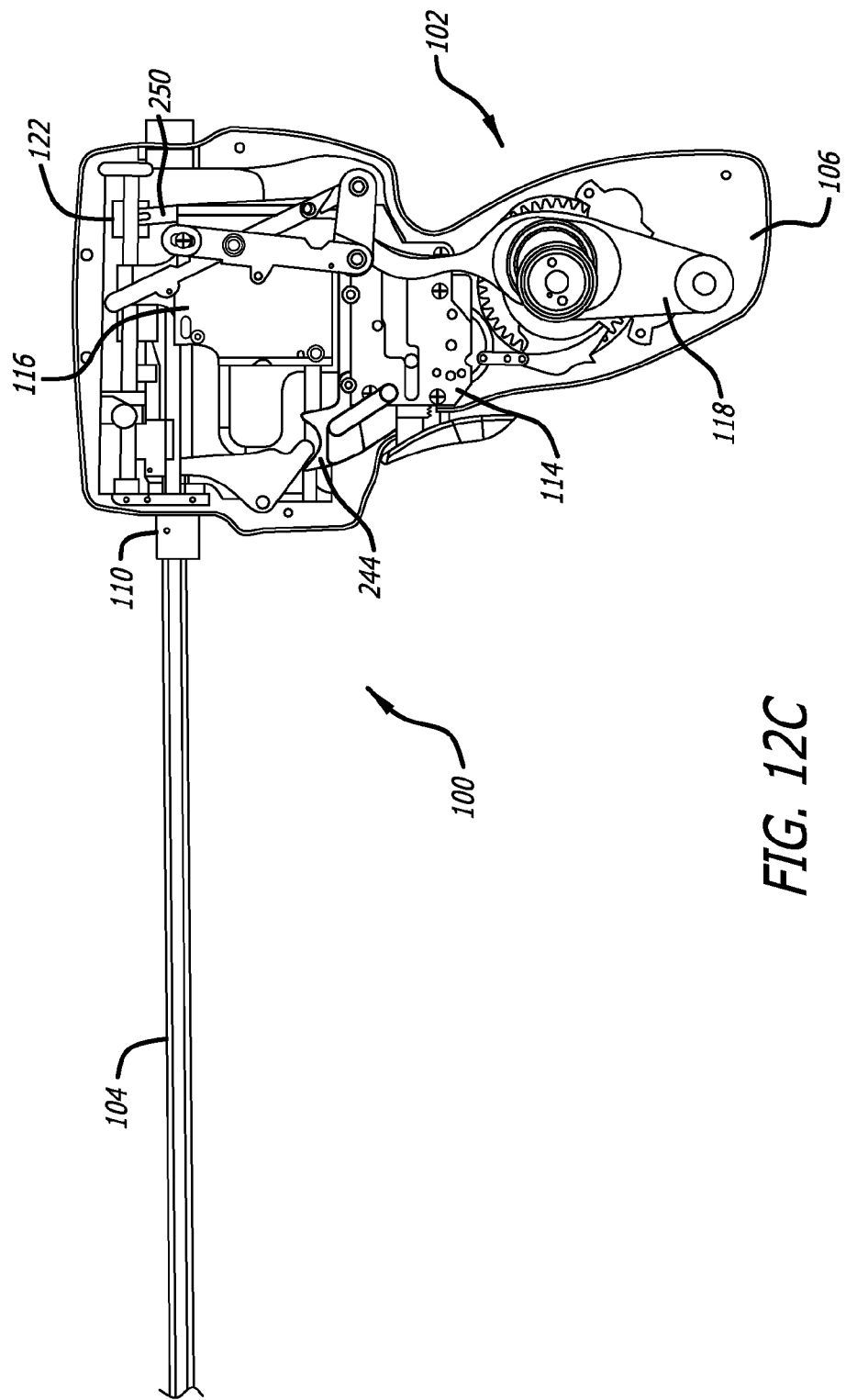
FIG. 12C is a left side view, depicting the complete depression of the trigger of the assembly of FIG. 12B with partial rotation of the cam.

Again with the trigger 254 automatically returning to a ready position (See FIG. 12A), the next step of the implant procedure can be accomplished. That is, as the trigger 254 is depressed for the fourth time (FIG. 12B), the pawl assembly 249 of the trigger assembly 114 is released from a locking engagement with the lower cam assembly 244 of the trigger assembly 114 (See also FIG. 5A). The complete depression of the trigger 254 (FIG. 12C) then effects the horizontal driving of the shaft 264 by the lower cam plate 266 of the lower cam assembly 244 (See also FIG. 5C). Consequently, the pin drive rear link 250 is translated forwardly and through its connection to the ratchet block assembly 122 (see also FIG. 2A), a pusher assembly (not shown) placed in apposition with rearmost second part 388 of the second anchor component is also advanced forwardly.

Irrespective of the specific form of the anchor assembly, a next step in the context of prostate treatment involves positioning the proximal anchor assembly, for example, within a desired section of the urethra of the patient. Prior to doing so, the patient can be monitored to determine whether there has been any evidence of improvement through the placement of the anchor. One such symptom is whether there has been any urination. After so checking, the proximal anchor assembly can be implanted.

Figure 12D:
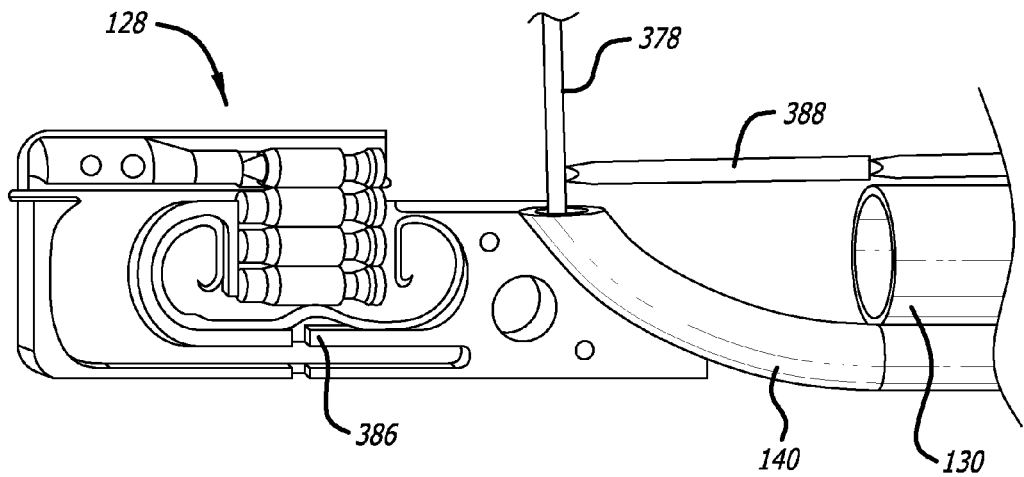
FIG. 12D is a partial cross-sectional view, depicting the assembly of FIG. 9D with the cover removed.
Figure 12E:
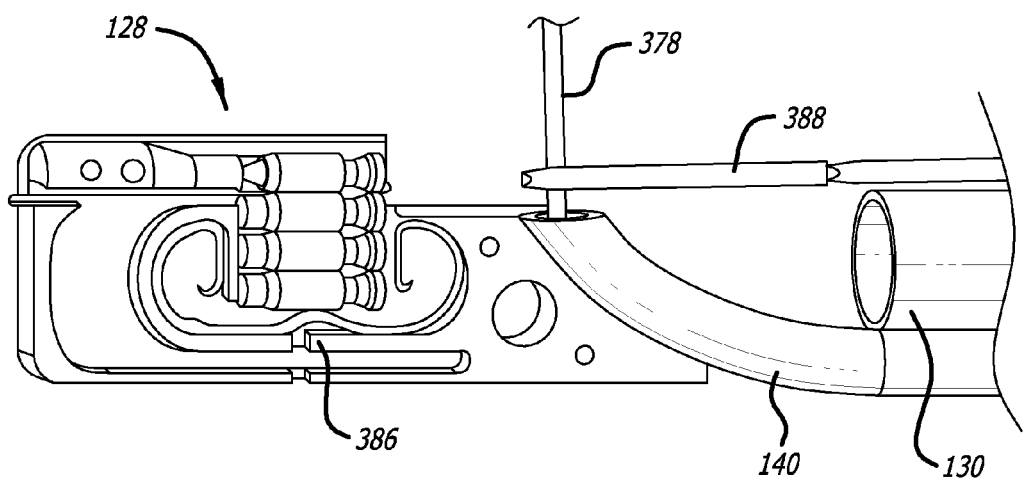
FIG. 12E is a partial cross-sectional view, depicting the deployment device of FIG. 12D with a second component of the second anchor member being advanced toward a first component of the second anchor member.
Figure 12F:
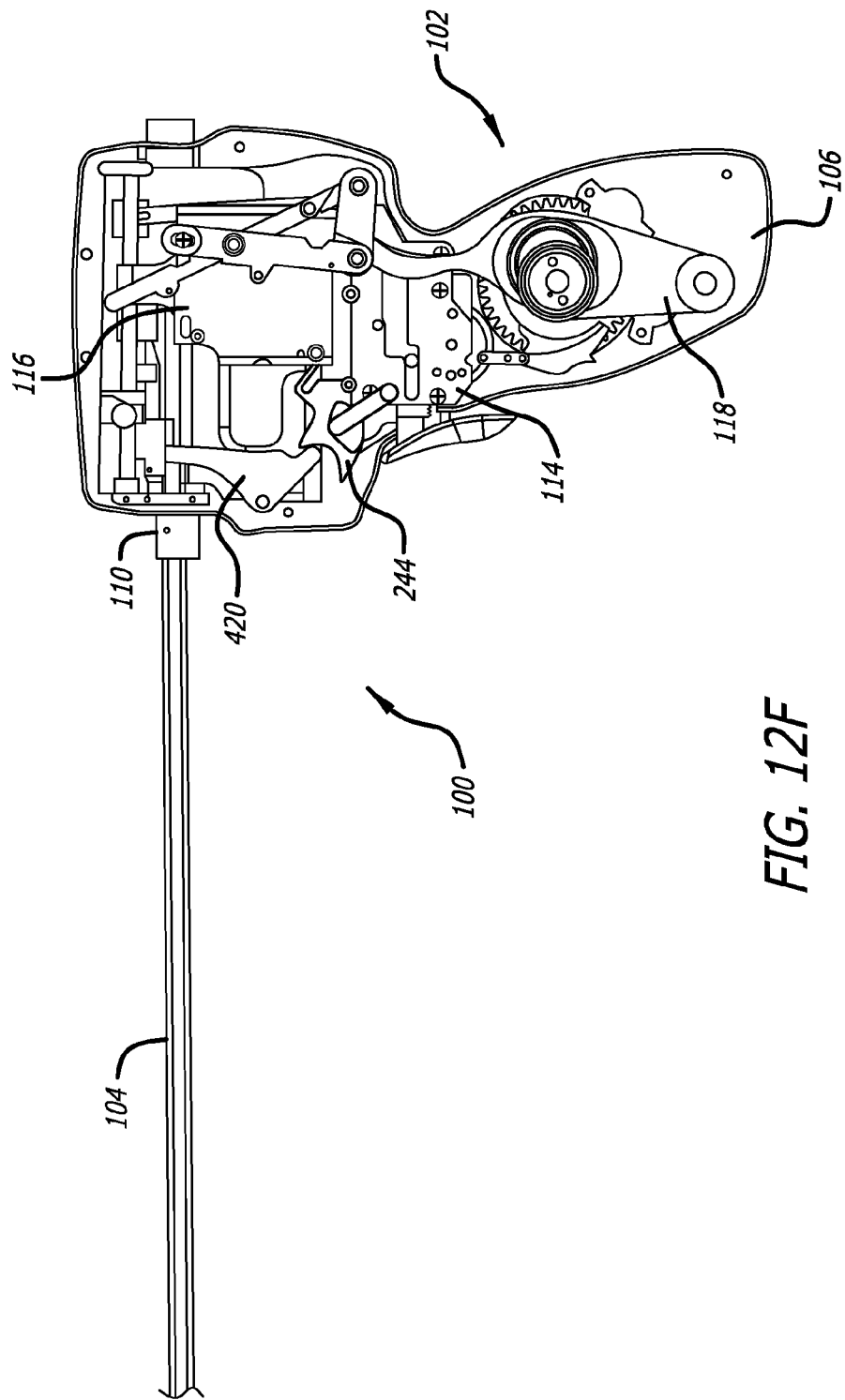
FIG. 12F is a left side view, depicting the assembly of FIG. 12C with full rotation of the cam and the outer tube assembly pulled proximally.
Figure 12G:
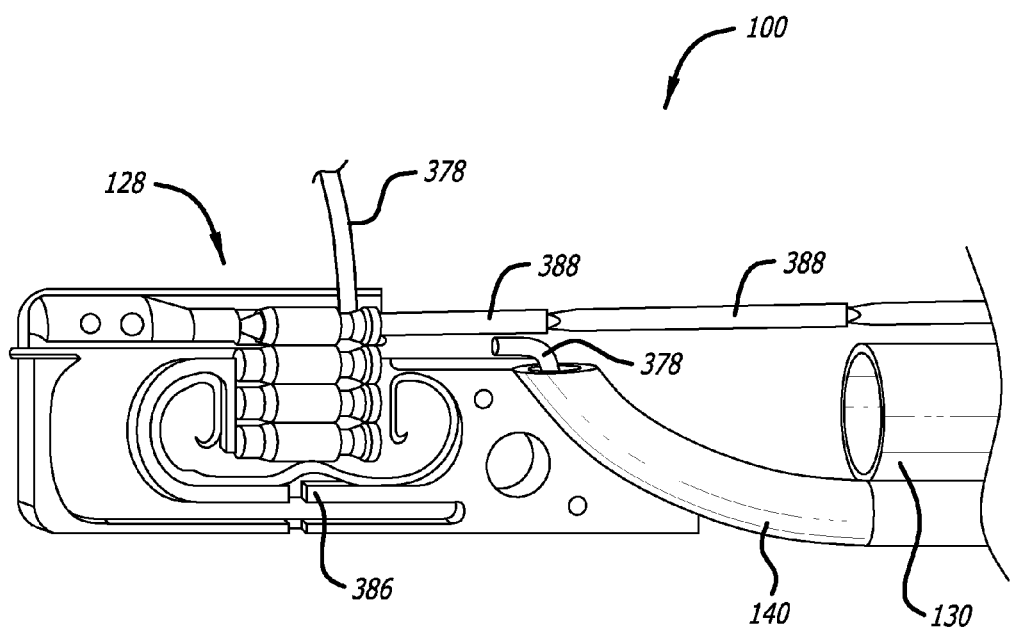
FIG. 12G is a perspective view, depicting the assembly of FIG. 9D of the delivery device with the second component completely advanced into locking engagement with the first component and the connector member cut.

Therefore, as shown in FIGS. 12D and 12E, by way of the pusher assembly, a second part 388 of the second anchor component is advanced into engagement with the connector 378 of the anchor assembly. The second part 388 is then further advanced into engagement with the first part 386 of the second anchor (FIG. 12G). At this juncture, the outer tube assembly (not shown) is pulled proximally to cut the connector 378 (See FIG. 12G) and release the assembled second anchor assembly from the distal end 128 of the multi-actuator trigger anchor delivery system 100. The proximal motion of the outer tube assembly is accomplished through the cooperation of an outer tube link 420 and the lower cam assembly 244. That is, as the lower cam assembly 244 rotates forwardly, its camming surface engages and rotates the outer tube link 420 in an opposite direction. By way of its connection to the outer tube assembly, the outer tube link 420 drives the outer tube assembly rearwardly.

Figure 12H:
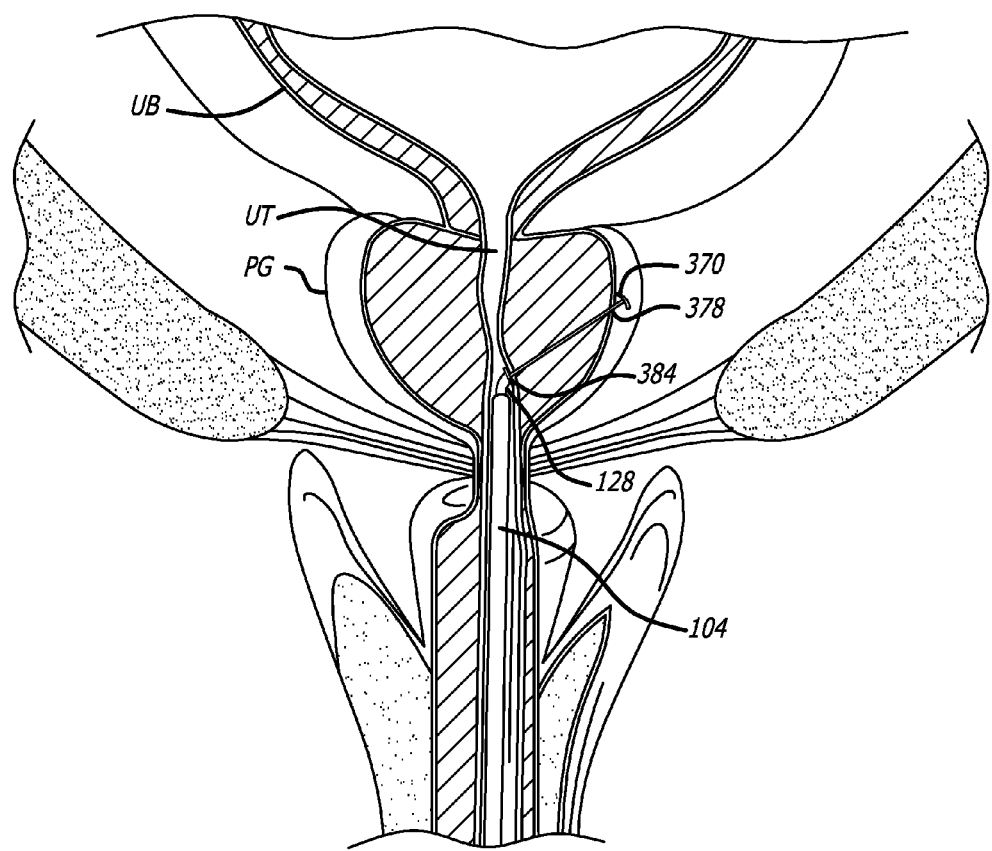
FIG. 12H is a cross-sectional view, depicting yet a further step involved in treating a prostate gland using the present invention.
Figure 13:
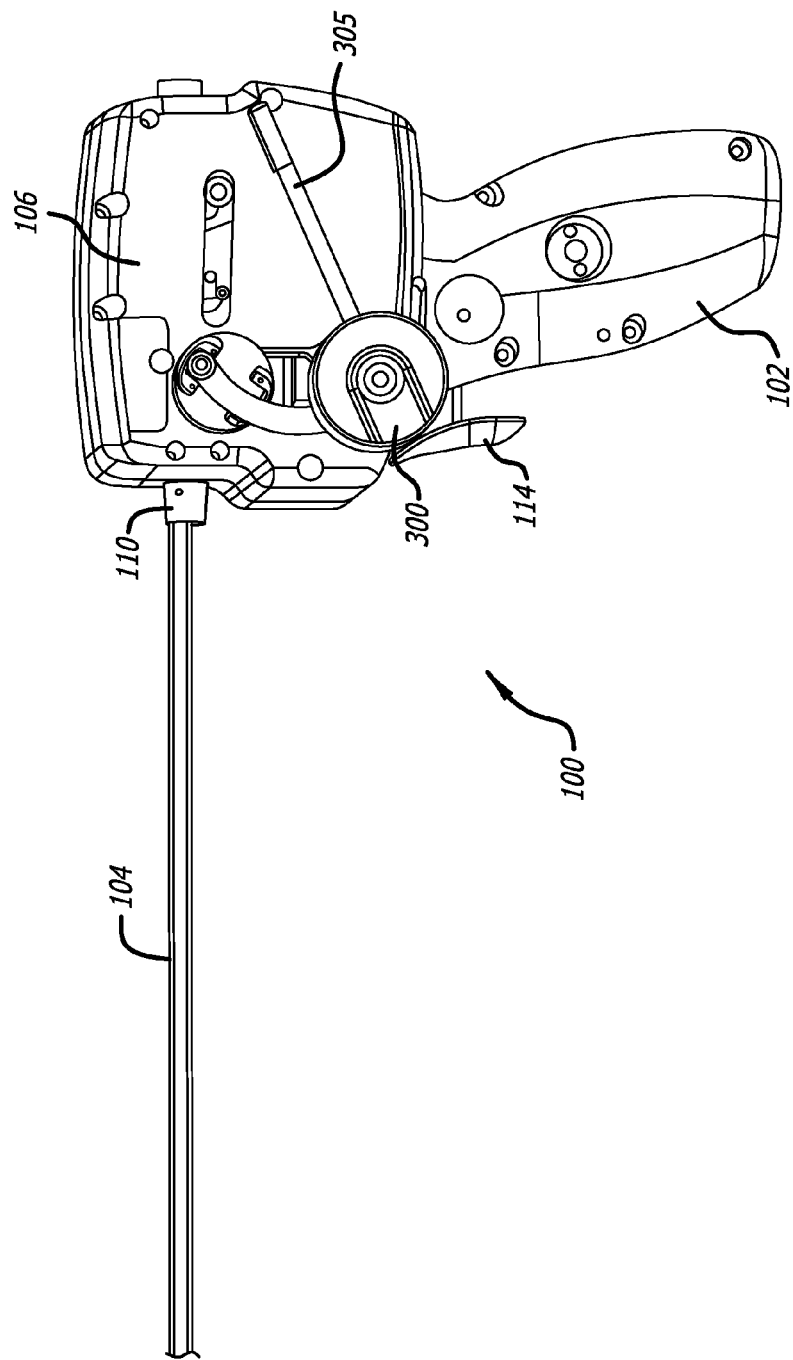
FIG. 13 is a left side view, depicting the multi-actuator trigger anchor delivery assembly of the present invention with the reset mechanism configured to recharge the system.

As shown in FIG. 12H, the assembled anchor assembly is placed across the prostate gland (PG) with the first anchor component 370 configured against an outer surface of the prostate gland (PG) and the second anchor component 384 implanted with the urethra (UT). Again, it is to be recognized that the anchor assembly can be placed in other orientations throughout a patient's anatomy.

Finally, the lever 305 of the reset assembly 300 is actuated to reset the system for assembling and implanting another second anchor component 384. That is, the lever 300 is pulled back to recharge the spring 304 of the reset assembly 300 to thereby return all of the assemblies to the correct position for accomplishing the assembly and release of the second anchor component 384. Moreover, it is to be recognized that the steps and mechanisms involved in delivering other components of the anchor assembly are effected with pre-loaded energy so that a desired number (e.g. four) of such components can be implanted.

Accordingly, the present invention contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed through a generally tubular portion of the anchor deployment device. Further, both a single anchor assembly or multiple anchor assemblies can be delivered and deployed at an intervention site by the deployment device. Consequently, in the context of prostate treatment, the present invention accomplishes both the compression of the prostate gland and the opening of the prostatic urethra, the delivering of an implant at the interventional site, and applying tension between ends of the implant. Moreover, drug delivery is both contemplated and described as a further remedy in BPH and over active bladder treatment.

Figure 14A:
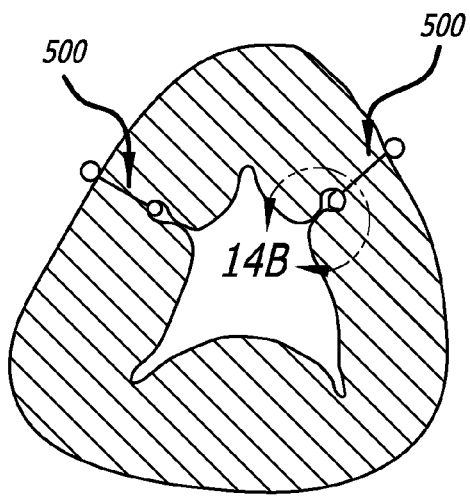
FIG. 14A is a cross-sectional view, depicting the implantation of anchor assemblies at an interventional site.
Figure 14B:
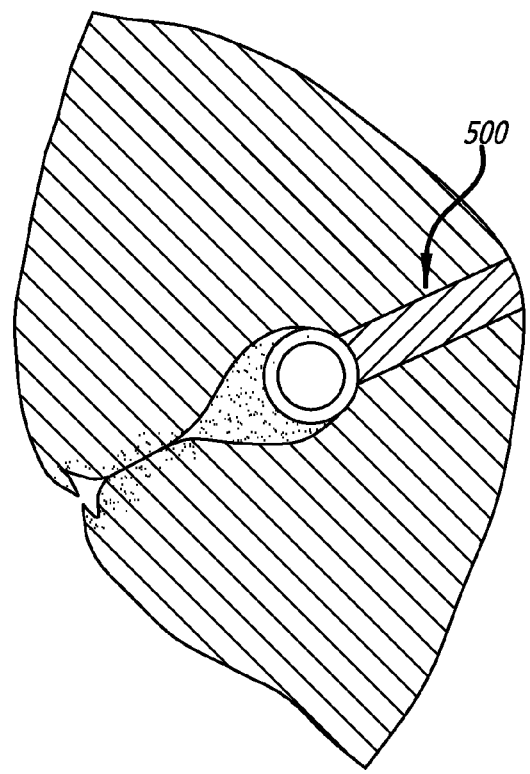
FIG. 14B is an enlarged view, depicting one anchor component of the assemblies shown in FIG. 14A.

Once implanted, the anchor assembly (See FIGS. 14A and 14B) of the present invention accomplishes desired tissue manipulation, compression or retraction as well as cooperates with the target anatomy to provide an atraumatic support structure. In particular, the shape and contour of the anchor assembly 500 can be configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly 500 and new cell growth occurs over time. Such cooperation with target tissue facilitates healing and avoids unwanted side effects such as calcification or infection at the interventional site.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

It has been observed that placing the anchors at various desired positions within anatomy can extract the best results. For example, when treating a prostate, one portion of an anchor can be placed within an urethra. It has been found that configuring such anchors so that ten o'clock and two o'clock positions (when looking along the axis of the urethra) are supported or retained, effectively holds the anatomy open and also can facilitate invagination of the anchor portion within natural tissue. This is particularly true in the regions of anatomy near the bladder and the juncture at which the ejaculatory duct connects to the urethra.

Additionally, it is contemplated that all components of the anchor assembly or selected portions thereof (of any of the anchor assemblies described or contemplated), may be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector 95 can for example, be coated with a polymer matrix or gel coating which retains the therapeutic or diagnostic substance and facilitates accomplishing the timed release thereof. Additionally, it is contemplated that bacteriostatic coatings can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is contemplated. In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is extended beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra.

An aspect that the various embodiments of the present invention provide is the ability to deliver multiple, preferably four, anchor assemblies having a customizable length and distal anchor components, each anchor assembly being implanted at a different location without having to remove the device from the patient. The various embodiments provide for variable needle depth and variable connector length for each of the multiple anchor assemblies delivered. Other aspects of the various embodiments of the present invention are load-based delivery, preferably 1 pound, of an anchor assembly, anchor assembly delivery with a device having integrated connector, (e.g. suture), cutting, and anchor assembly delivery with an endoscope in the device. The delivery device is uniquely configured to place such a load (half pound to five pounds) between spaced first anchor members as well as between or on an implanted first anchor and the delivery device. In this aspect, the needle assembly acting as a penetrating member can be cooperatively connected to a mechanism which produces a desired tension between the various anchor members while the needle assembly is retracted. Moreover, this load can be accomplished between first and second implanted anchor members.

It is to be recognized that various materials are contemplated for manufacturing the disclosed devices. Moreover, one or more components such as distal anchor, proximal anchor, connector, of the one or more anchor devices disclosed herein may be designed to be completely or partially biodegradable or biofragmentable.

Further, as stated, the devices and methods disclosed herein may be used to treat a variety of pathologies in a variety of tubular organs or organs comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alteration are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A system including an anchor assembly for assembly within a patient's body, comprising:
   a first anchor member;
   a second anchor member including a first part and a second part;
   a connector joining the first and second anchor members;
   wherein one or both of the first and second parts are configured to be initially detached and then assembled by joining with the connector and each other via a locking engagement between the first and second parts within a patient's body;
   wherein the system is configured with a single trigger which accomplishes the assembly of the anchor assembly within a patient's body and accomplishes the implantation of an assembled anchor assembly;
   wherein the system is configured to deploy a plurality of anchor assemblies.

2. The system of claim 1, further comprising a needle assembly, wherein the system includes structure to extend the needle assembly to varying depths.

3. The system of claim 1, further comprising a mechanism to prevent incomplete activation of the trigger.

4. The system of claim 1, further comprising a scope wherein the scope extends substantially toward a terminal end of the anchor delivery device and provides a complete or partial view of deployment and assembly of same or all of the anchor assemblies.

5. The system of claim 1, further comprising a needle assembly, the needle assembly configured to house the first anchor member and connector, the needle assembly being operatively associated with the trigger.

6. The system of claim 5, further comprising a first pusher assembly, the first pusher assembly being operatively associated with the trigger and being placed into engagement with the first anchor member and connector.

7. The system of claim 6, further comprising a relative movement assembly operatively associated with the trigger, wherein actuation of a first actuator accomplishes the relative movement between the pusher assembly and the needle assembly.

8. The system of claim 7, further comprising a second pusher assembly, the second pusher assembly being operatively associated with the trigger and being placed into engagement with one part of the second anchor assembly.

9. The system of claim 8, further comprising a tension mechanism that is configured to apply approximately one pound of force on the connector.

10. The system of claim 8, wherein the tension mechanism is configured to apply approximately one half to five pounds force on the connector.

11. The system of claim 8, wherein the tension mechanism is configured to apply a selectable tension between approximately a half pound to five pounds of force on the connector.

12. The system of claim 1, wherein the anchor delivery device includes a penetrating member which is extendable from the system.

13. The system of claim 12, wherein the first anchor member is delivered through the penetrating member.

14. The system of claim 13, wherein the first anchor member and connector are pushed through the penetrating member by a rotary drive mechanism.

15. The system of claim 13, wherein the second anchor member is not delivered through the penetrating member.

16. The system of claim 13, wherein the penetrating member is operatively associated with a tensile load system to thereby produce a load on the first anchor member when the penetrating member is retracted.

17. The system of claim 16, wherein the tensile load system is a rotary mechanism.

18. The system of claim 1, wherein the system houses a plurality of anchor assemblies.

* * * * *